US007504104B2

(12) United States Patent
Shitara et al.

(10) Patent No.: US 7,504,104 B2
(45) Date of Patent: Mar. 17, 2009

(54) HUMAN CDR-GRAFTED ANTIBODY AND ANTIBODY FRAGMENT THEREOF

(75) Inventors: Kenya Shitara, Machida (JP); Kazuyasu Nakamura, Machida (JP); Emi Hosaka, Machida (JP); Akiko Tanaka, Machida (JP); Masamichi Koike, Machida (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 134 days.

(21) Appl. No.: 10/231,452

(22) Filed: Aug. 30, 2002

(65) Prior Publication Data

US 2003/0175273 A1 Sep. 18, 2003

(30) Foreign Application Priority Data

Aug. 31, 2001 (JP) ............................ 2001-265144

(51) Int. Cl.
*A61K 39/395* (2006.01)
*C12P 21/08* (2006.01)

(52) U.S. Cl. ............. 424/139.1; 530/387.3; 530/387.9; 424/130.1; 424/133.1

(58) Field of Classification Search ...................... None
See application file for complete search history.

(56) References Cited

U.S. PATENT DOCUMENTS

| | | | | |
|---|---|---|---|---|
| 6,488,930 | B1 | 12/2002 | Wu et al. | |
| 6,989,145 | B2 * | 1/2006 | Shitara et al. | 424/144.1 |
| 2002/0098527 | A1 | 7/2002 | Shitara et al. | 33/567 |

FOREIGN PATENT DOCUMENTS

| | | |
|---|---|---|
| WO | WO 97/10354 | 3/1997 |
| WO | WO 99/25380 | 5/1999 |
| WO | WO 00/00219 | 1/2000 |
| WO | WO 00/42074 | 7/2000 |
| WO | WO0042074 A1 * | 7/2000 |
| WO | WO 00/67791 | 11/2000 |

OTHER PUBLICATIONS

Lederman, et al. Mol. Immunol.28: 1171-1181, 1991 'A single amino acid substitution in a ommon African allele of the CD4 molecule ablates binding of the monoclonal antibody, OKT4'.*

Gerard, et al. Nature Immunol. 2:108-115, 2001'Chemokines and Disease'.*

Power, et al. J. Biol. Chem. 270: 19495-19500, 1995 'Molecular Cloning and functional expression of a novel CC chemokine Receptor cDNA froma Human Basophilic Cell line'.*

Co, et al. Cancer Res. 56: 1118-1125, 1996'Humanized anti-Lewis Y antibodies: In vitro properties and pharmacokinetics in Rhesus Monkeys'.*

Clemetson, et al., "Functional expression of CCR1, CCR3, CCR4, and CXCR4 chemokine receptors on human platelets", Blood, vol. 96, No. 13 (2000), pp. 4046-4054.

Andrew et al, . J. Immunol. Jan. 1, 2001, vol. 166, No. 1, p. 103-111.

Imai et al, Int. Immunol. 1999, vol. 11, No. 1, p. 81-88.

Landolfi et al, J. Immunol. Feb. 1, 2001, vol. 166, No. 3, p. 1748-1754.

He et al, J. Immunol. Jan. 15, 1998, vol. 160, No. 2 p. 1029-1035.

Brown et al Proc. Natl. Acad. Sci. USA Apr. 1, 1991, vol. 88, No. 7, 2663-2667.

Co et al Proc. Natl. Acad. Sci. USA Apr. 1, 1991, vol. 88, No. 7, p. 2869-2873.

Junghans et al Cancer Res. 199, vol. 50, No. 5, p. 1495-1502.

Queen et al Proc. Natl. Acad. Sci. USA 1989 vol. 86, No. 24, p. 10029-10033.

Power, et al., "Molecular Cloning and Functional Expression of a Novel CC Chemokine Receptor cDNA from a Human Basophilic Cell Line", The Journal of Biological Chemistry, vol. 270, No. 33 (1995), pp. 19495-19500.

Jones, et al., "Expression pattern to T-cell-associated chemokine receptors and their chemokines correlates with specific subtypes of T-cell non-Hodgkin lymphoma", Blood, vol. 96, No. 2 (2000), pp. 685-690.

Mueller, et al., "Enhancement of Antibody Dependent Cytotoxicity with a Chimeric Anti-GD2 1 Antibody", J. of Immunology, vol. 144, No. 4 (1990), pp. 1382-1386.

Riechmann, et al., "Reshaping human antibodies for therapy", Nature, vol. 332 (1988), pp. 323-327.

Van Den Berg, et al., "High Expression of the CC Chemokine T ARC in Reed-Stember Cells", Am. J. of Pathology, vol. 154, No. 6 (1999), pp. 1685-1691.

D'Ambrosio, et al., "Cutting Edge: Selective Up-Regulation of Chemokine Receptors CCR4 and CCR8 upon Activation of Polarized . . . ", J. Immunology, Cutting Edge, 0022-1767 (1998), pp. 5111-5115.

Bonecchi, et al., "Differential Expression of Chemokine Receptors and Chemotactic Responsiveness of Type 1 T Helper Cells (Th1s) and Th2s", J. Exp. Med., vol. 87, No. 1 (1998), pp. 129-134.

Youn et al., "Molecular Cloning and Characterization of a cDNA, CHEMR1, Encoding a Chemokine Receptor with a Homology to the Human C-C Chemokine Receptor, CCR-4", Blood, vol. 89, No. 12 (1997), pp. 4448-4460.

Frade et al., "The amino-terminal Domain of the CCR2 Chemokine Receptor Acts as Coreceptor for HIV-1 Infection", J. Clin. Invest., vol. 100, No. 3 (1997), pp. 497-502.

Kashmiri, et al., "SDR Grafting- A New Approach to Antibody Humanization", Methods, vol. 36 (2005), pp. 25-34.

* cited by examiner

*Primary Examiner*—Marianne P Allen
(74) *Attorney, Agent, or Firm*—Sughrue Mion, PLLC

(57) ABSTRACT

A human CDR-grafted antibody or the antibody fragment thereof which specifically reacts with the extracellular region of human CC chemokine receptor 4 (CCR4) but does not react with a human blood platelet; a human CDR-grafted antibody or the antibody fragment thereof which specifically reacts with the extracellular region of CCR4 and has a cytotoxic activity against a CCR4-expressing cell; and a medicament, a therapeutic agent or a diagnostic agent comprising at least one of the antibodies and the antibody fragments thereof as an active ingredient.

19 Claims, 17 Drawing Sheets

SEQUENCE LISTING

```
<160> NUMBER OF SEQ ID NOS: 78

<210> SEQ ID NO 1
<211> LENGTH: 5
<212> TYPE: PRT
<213> ORGANISM: Mus musculus

<400> SEQUENCE: 1

Asn Tyr Gly Met Ser
  1             5


<210> SEQ ID NO 2
<211> LENGTH: 17
<212> TYPE: PRT
<213> ORGANISM: Mus musculus

<400> SEQUENCE: 2

Thr Ile Ser Ser Ala Ser Thr Tyr Ser Tyr Tyr Pro Asp Ser Val Lys
  1             5                  10                  15

Gly


<210> SEQ ID NO 3
<211> LENGTH: 10
<212> TYPE: PRT
<213> ORGANISM: Mus musculus

<400> SEQUENCE: 3

His Ser Asp Gly Asn Phe Ala Phe Gly Tyr
  1             5                  10


<210> SEQ ID NO 4
<211> LENGTH: 119
<212> TYPE: PRT
<213> ORGANISM: Artificial Sequence
<220> FEATURE:
```

-continued

<223> OTHER INFORMATION: Synthetic peptide

<400> SEQUENCE: 4

Glu Val Gln Leu Val Glu Ser Gly Gly Asp Leu Val Gln Pro Gly Arg
1 5 10 15

Ser Leu Arg Leu Ser Cys Ala Ala Ser Gly Phe Ile Phe Ser Asn Tyr
20 25 30

Gly Met Ser Trp Val Arg Gln Ala Pro Gly Lys Gly Leu Glu Trp Val
35 40 45

Ala Thr Ile Ser Ser Ala Ser Thr Tyr Ser Tyr Tyr Pro Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Val Glu Asp Thr Ala Leu Tyr Tyr Cys
85 90 95

Ala Arg His Ser Asp Gly Asn Phe Ala Phe Gly Tyr Trp Gly Gln Gly
100 105 110

Thr Leu Val Thr Val Ser Ser
115

<210> SEQ ID NO 5
<211> LENGTH: 16
<212> TYPE: PRT
<213> ORGANISM: Mus musculus

<400> SEQUENCE: 5

Arg Ser Ser Arg Asn Ile Val His Ile Asn Gly Asp Thr Tyr Leu Glu
1 5 10 15

<210> SEQ ID NO 6
<211> LENGTH: 7
<212> TYPE: PRT
<213> ORGANISM: Mus musculus

<400> SEQUENCE: 6

Lys Val Ser Asn Arg Phe Ser
1 5

<210> SEQ ID NO 7
<211> LENGTH: 9
<212> TYPE: PRT
<213> ORGANISM: Mus musculus

<400> SEQUENCE: 7

Phe Gln Gly Ser Leu Leu Phe Trp Thr
1 5

<210> SEQ ID NO 8
<211> LENGTH: 112
<212> TYPE: PRT
<213> ORGANISM: Artificial Sequence
<220> FEATURE:
<223> OTHER INFORMATION: Synthetic peptide

<400> SEQUENCE: 8

Asp Ile Val Met Thr Gln Ser Pro Leu Ser Leu Pro Val Thr Pro Gly
1 5 10 15

Glu Pro Ala Ser Ile Ser Cys Arg Ser Ser Arg Asn Ile Val His Ile
20 25 30

Asn Gly Asp Thr Tyr Leu Glu Trp Tyr Leu Gln Lys Pro Gly Gln Ser
35 40 45

-continued

```
Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser Leu Leu Pro Trp Thr Phe Gly Gln Gly Thr Lys Val Glu Ile Lys
            100                 105                 110
```

<210> SEQ ID NO 9
<211> LENGTH: 119
<212> TYPE: PRT
<213> ORGANISM: Artificial Sequence
<220> FEATURE:
<223> OTHER INFORMATION: Synthetic peptide

<400> SEQUENCE: 9

```
Glu Val Gln Leu Val Glu Ser Gly Gly Asp Leu Val Gln Pro Gly Arg
  1               5                  10                  15

Ser Leu Arg Leu Ser Cys Ala Ala Ser Gly Phe Ile Phe Ser Asn Tyr
             20                  25                  30

Gly Met Ser Trp Val Arg Gln Ala Pro Gly Lys Gly Leu Glu Trp Val
         35                  40                  45

Ala Thr Ile Ser Ser Ala Ser Thr Tyr Ser Tyr Tyr Pro Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Leu Tyr Tyr Cys
                 85                  90                  95

Gly Arg His Ser Asp Gly Asn Phe Ala Phe Gly Tyr Trp Gly Gln Gly
            100                 105                 110

Thr Leu Val Thr Val Ser Ser
        115
```

<210> SEQ ID NO 10
<211> LENGTH: 119
<212> TYPE: PRT
<213> ORGANISM: Artificial Sequence
<220> FEATURE:
<223> OTHER INFORMATION: Synthetic peptide

<400> SEQUENCE: 10

```
Glu Val Gln Leu Val Glu Ser Gly Gly Asp Leu Val Gln Pro Gly Arg
  1               5                  10                  15

Ser Leu Arg Leu Ser Cys Ala Ala Ser Gly Phe Ile Phe Ser Asn Tyr
             20                  25                  30

Gly Met Ser Trp Val Arg Gln Ala Pro Asp Lys Arg Leu Glu Trp Val
         35                  40                  45

Ala Thr Ile Ser Ser Ala Ser Thr Tyr Ser Tyr Tyr Pro Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Leu Tyr Tyr Cys
                 85                  90                  95

Ala Arg His Ser Asp Gly Asn Phe Ala Phe Gly Tyr Trp Gly Gln Gly
            100                 105                 110

Thr Leu Val Thr Val Ser Ser
```

-continued

115

<210> SEQ ID NO 11
<211> LENGTH: 119
<212> TYPE: PRT
<213> ORGANISM: Artificial Sequence
<220> FEATURE:
<223> OTHER INFORMATION: Synthetic peptide

<400> SEQUENCE: 11

```
Glu Val Gln Leu Val Glu Ser Gly Gly Asp Leu Val Gln Pro Gly Arg
  1               5                  10                  15

Ser Leu Arg Leu Ser Cys Ala Ala Ser Gly Phe Ile Phe Ser Asn Tyr
             20                  25                  30

Gly Met Ser Trp Val Arg Gln Ala Pro Asp Lys Arg Leu Glu Trp Val
         35                  40                  45

Ala Thr Ile Ser Ser Ala Ser Thr Tyr Ser Tyr Tyr Pro Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Val Glu Asp Thr Ala Leu Tyr Tyr Cys
                 85                  90                  95

Gly Arg His Ser Asp Gly Asn Phe Ala Phe Gly Tyr Trp Gly Gln Gly
            100                 105                 110

Thr Leu Val Thr Val Ser Ser
        115
```

<210> SEQ ID NO 12
<211> LENGTH: 112
<212> TYPE: PRT
<213> ORGANISM: Artificial Sequence
<220> FEATURE:
<223> OTHER INFORMATION: Synthetic peptide

<400> SEQUENCE: 12

```
Asp Val Val Met Thr Gln Ser Pro Leu Ser Leu Pro Val Thr Pro Gly
  1               5                  10                  15

Glu Pro Ala Ser Ile Ser Cys Arg Ser Ser Arg Asn Ile Val His Ile
             20                  25                  30

Asn Gly Asp Thr Tyr Leu Glu Trp Tyr Leu Gln Lys Pro Gly Gln Ser
         35                  40                  45

Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser Leu Leu Pro Trp Thr Phe Gly Gln Gly Thr Lys Val Glu Ile Lys
            100                 105                 110
```

<210> SEQ ID NO 13
<211> LENGTH: 112
<212> TYPE: PRT
<213> ORGANISM: Artificial Sequence
<220> FEATURE:
<223> OTHER INFORMATION: Synthetic peptide

<400> SEQUENCE: 13

```
Asp Ile Leu Met Thr Gln Ser Pro Leu Ser Leu Pro Val Thr Pro Gly
  1               5                  10                  15
```

-continued

```
Glu Pro Ala Ser Ile Ser Cys Arg Ser Ser Arg Asn Ile Val His Ile
             20                  25                  30

Asn Gly Asp Thr Tyr Leu Glu Trp Tyr Leu Gln Lys Pro Gly Gln Ser
         35                  40                  45

Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser Leu Leu Pro Trp Thr Phe Gly Gln Gly Thr Lys Val Glu Ile Lys
            100                 105                 110


<210> SEQ ID NO 14
<211> LENGTH: 112
<212> TYPE: PRT
<213> ORGANISM: Artificial Sequence
<220> FEATURE:
<223> OTHER INFORMATION: Synthetic peptide

<400> SEQUENCE: 14

Asp Val Leu Met Thr Gln Ser Pro Leu Ser Leu Pro Val Thr Pro Gly
  1               5                  10                  15

Glu Pro Ala Ser Ile Ser Cys Arg Ser Ser Arg Asn Ile Val His Ile
             20                  25                  30

Asn Gly Asp Thr Tyr Leu Glu Trp Tyr Leu Gln Lys Pro Gly Gln Ser
         35                  40                  45

Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser Leu Leu Pro Trp Thr Phe Gly Gln Gly Thr Lys Val Glu Ile Lys
            100                 105                 110


<210> SEQ ID NO 15
<211> LENGTH: 19
<212> TYPE: PRT
<213> ORGANISM: Mus musculus

<400> SEQUENCE: 15

Met Asn Leu Gly Leu Ser Leu Ile Phe Leu Ala Leu Ile Leu Lys Gly
  1               5                  10                  15

Val Gln Cys


<210> SEQ ID NO 16
<211> LENGTH: 98
<212> TYPE: DNA
<213> ORGANISM: Artificial Sequence
<220> FEATURE:
<223> OTHER INFORMATION: Synthetic DNA

<400> SEQUENCE: 16

aacagctatg accatggcgg ccgcgacccc tcaccatgaa cctcgggctc agtttgattt     60

tccttgccct cattttaaaa ggtgtccagt gtgaggtg                             98


<210> SEQ ID NO 17
```

-continued

<211> LENGTH: 97
<212> TYPE: DNA
<213> ORGANISM: Artificial Sequence
<220> FEATURE:
<223> OTHER INFORMATION: Synthetic DNA

<400> SEQUENCE: 17
atgaatccag aggctgcaca ggagagtctc agggacctcc caggctgtac caagtctccc 60
ccagactcca ccagctgcac ctcacactgg acacctt 97

<210> SEQ ID NO 18
<211> LENGTH: 98
<212> TYPE: DNA
<213> ORGANISM: Artificial Sequence
<220> FEATURE:
<223> OTHER INFORMATION: Synthetic DNA

<400> SEQUENCE: 18
tgtgcagcct ctggattcat tttcagtaat tatggcatgt cttgggtccg ccaggctcca 60
gggaaggggc tggagtgggt cgcaaccatt agtagtgc 98

<210> SEQ ID NO 19
<211> LENGTH: 98
<212> TYPE: DNA
<213> ORGANISM: Artificial Sequence
<220> FEATURE:
<223> OTHER INFORMATION: Synthetic DNA

<400> SEQUENCE: 19
acagggagtt cttggcattg tctctggaga tggtgaatcg tcccttcaca ctgtctggat 60
aataggaata agtgctagca ctactaatgg ttgcgacc 98

<210> SEQ ID NO 20
<211> LENGTH: 98
<212> TYPE: DNA
<213> ORGANISM: Artificial Sequence
<220> FEATURE:
<223> OTHER INFORMATION: Synthetic DNA

<400> SEQUENCE: 20
acaatgccaa gaactccctg tatctgcaga tgaacagcct gagagtcgag gacacggccc 60
tgtattactg tgcgagacat agcgatggaa acttcgcg 98

<210> SEQ ID NO 21
<211> LENGTH: 96
<212> TYPE: DNA
<213> ORGANISM: Artificial Sequence
<220> FEATURE:
<223> OTHER INFORMATION: Synthetic DNA

<400> SEQUENCE: 21
gtaaaacgac ggccagtggg cccttggtgg aggctgagga gacggtgacc agggttccct 60
ggccccaata accaaacgcg aagtttccat cgctat 96

<210> SEQ ID NO 22
<211> LENGTH: 17
<212> TYPE: DNA
<213> ORGANISM: Artificial Sequence
<220> FEATURE:
<223> OTHER INFORMATION: Synthetic DNA

<400> SEQUENCE: 22
gatggttcac gtagtgg 17

-continued

<210> SEQ ID NO 23
<211> LENGTH: 61
<212> TYPE: DNA
<213> ORGANISM: Artificial Sequence
<220> FEATURE:
<223> OTHER INFORMATION: Synthetic DNA

<400> SEQUENCE: 23
ctgtatctgc agatgaacag cctgagagtc gaggacacgg ccctgtatta ctgtggaaga 60
c 61

<210> SEQ ID NO 24
<211> LENGTH: 56
<212> TYPE: DNA
<213> ORGANISM: Artificial Sequence
<220> FEATURE:
<223> OTHER INFORMATION: Synthetic DNA

<400> SEQUENCE: 24
gaataagtgc tagcactact aatggttgcg acccactcca gcctcttgtc tggagc 56

<210> SEQ ID NO 25
<211> LENGTH: 19
<212> TYPE: PRT
<213> ORGANISM: Mus musculus

<400> SEQUENCE: 25

Met Lys Leu Pro Val Arg Leu Leu Val Leu Met Phe Trp Ile Pro Ala
1 5 10 15

Ser Ser Ser

<210> SEQ ID NO 26
<211> LENGTH: 92
<212> TYPE: DNA
<213> ORGANISM: Artificial Sequence
<220> FEATURE:
<223> OTHER INFORMATION: Synthetic DNA

<400> SEQUENCE: 26
aacagctatg accatggaat tcgcctcttc aaaatgaagt tgcctgttag gctgttggtg 60
ctgatgttct ggattcctgc ttccagcagt ga 92

<210> SEQ ID NO 27
<211> LENGTH: 94
<212> TYPE: DNA
<213> ORGANISM: Artificial Sequence
<220> FEATURE:
<223> OTHER INFORMATION: Synthetic DNA

<400> SEQUENCE: 27
tagatctgca ggagatggag gccggctctc caggggtgac gggcagggag agtggagact 60
gagtcatcac gatatcactg ctggaagcag gaat 94

<210> SEQ ID NO 28
<211> LENGTH: 92
<212> TYPE: DNA
<213> ORGANISM: Artificial Sequence
<220> FEATURE:
<223> OTHER INFORMATION: Synthetic DNA

<400> SEQUENCE: 28
ctccatctcc tgcagatcta gtcggaacat tgttcatatt aatggtgaca catatttaga 60

-continued atggtacctg cagaagccag gccagtctcc ac 92

<210> SEQ ID NO 29
<211> LENGTH: 93
<212> TYPE: DNA
<213> ORGANISM: Artificial Sequence
<220> FEATURE:
<223> OTHER INFORMATION: Synthetic DNA

<400> SEQUENCE: 29
tgtgcctgac ccactgccac tgaacctgtc tgggacccca gaaaatcggt tggaaacttt 60
atagatcagg agctgtggag actggcctgg ctt 93

<210> SEQ ID NO 30
<211> LENGTH: 92
<212> TYPE: DNA
<213> ORGANISM: Artificial Sequence
<220> FEATURE:
<223> OTHER INFORMATION: Synthetic DNA

<400> SEQUENCE: 30
tggcagtggg tcaggcacag atttcacact gaaaatcagc agagtggagg ctgaggatgt 60
tggggtttat tactgctttc aaggttcact tc 92

<210> SEQ ID NO 31
<211> LENGTH: 91
<212> TYPE: DNA
<213> ORGANISM: Artificial Sequence
<220> FEATURE:
<223> OTHER INFORMATION: Synthetic DNA

<400> SEQUENCE: 31
gtaaaacgac ggccagtctc gagcgtacgt ttgatttcca ccttggtccc ttggccgaac 60
gtccacggaa gaagtgaacc ttgaaagcag t 91

<210> SEQ ID NO 32
<211> LENGTH: 17
<212> TYPE: DNA
<213> ORGANISM: Artificial Sequence
<220> FEATURE:
<223> OTHER INFORMATION: Synthetic DNA

<400> SEQUENCE: 32
gtaaaacgac ggccagt 17

<210> SEQ ID NO 33
<211> LENGTH: 94
<212> TYPE: DNA
<213> ORGANISM: Artificial Sequence
<220> FEATURE:
<223> OTHER INFORMATION: Synthetic DNA

<400> SEQUENCE: 33
tagatctgca ggagatggag gccggctctc caggggtgac gggcagggag agtggagact 60
gagtcatcac aacatcactg ctggaagcag gaat 94

<210> SEQ ID NO 34
<211> LENGTH: 94
<212> TYPE: DNA
<213> ORGANISM: Artificial Sequence
<220> FEATURE:
<223> OTHER INFORMATION: Synthetic DNA -continued

<400> SEQUENCE: 34
tagatctgca ggagatggag gccggctctc caggggtgac gggcagggag agtggagact 60
gagtcatcaa gatatcactg ctggaagcag gaat 94

<210> SEQ ID NO 35
<211> LENGTH: 94
<212> TYPE: DNA
<213> ORGANISM: Artificial Sequence
<220> FEATURE:
<223> OTHER INFORMATION: Synthetic DNA

<400> SEQUENCE: 35
tagatctgca ggagatggag gccggctctc caggggtgac gggcagggag agtggagact 60
gagtcatcaa aacatcactg ctggaagcag gaat 94

<210> SEQ ID NO 36
<211> LENGTH: 28
<212> TYPE: PRT
<213> ORGANISM: Homo sapiens

<400> SEQUENCE: 36

Asn Pro Thr Asp Ile Ala Asp Thr Thr Leu Asp Glu Ser Ile Tyr Ser
1 5 10 15

Asn Tyr Tyr Leu Tyr Glu Ser Ile Pro Lys Pro Cys
20 25

<210> SEQ ID NO 37
<211> LENGTH: 18
<212> TYPE: PRT
<213> ORGANISM: Homo sapiens

<400> SEQUENCE: 37

Asp Glu Ser Ile Tyr Ser Asn Tyr Tyr Leu Tyr Glu Ser Ile Pro Lys
1 5 10 15

Pro Cys

<210> SEQ ID NO 38
<211> LENGTH: 119
<212> TYPE: PRT
<213> ORGANISM: Artificial Sequence
<220> FEATURE:
<223> OTHER INFORMATION: Synthetic peptide

<400> SEQUENCE: 38

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Gly Met Ser Trp Val Arg Gln Ala Pro Gly Lys Gly Leu Glu Trp Val
35 40 45

Ser Thr Ile Ser Ser Ala Ser Thr Tyr Ser Tyr Tyr Pro Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg His Ser Asp Gly Asn Phe Ala Phe Gly Tyr Trp Gly Gln Gly
100 105 110

Thr Leu Val Thr Val Ser Ser

-continued

115

<210> SEQ ID NO 39
<211> LENGTH: 119
<212> TYPE: PRT
<213> ORGANISM: Artificial Sequence
<220> FEATURE:
<223> OTHER INFORMATION: Synthetic peptide

<400> SEQUENCE: 39

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Ile Phe Ser Asn Tyr
             20                  25                  30

Gly Met Ser Trp Val Arg Gln Ala Pro Gly Lys Gly Leu Glu Trp Val
         35                  40                  45

Ser Thr Ile Ser Ser Ala Ser Thr Tyr Ser Tyr Tyr Pro Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Ser Asp Gly Asn Phe Ala Phe Gly Tyr Trp Gly Gln Gly
            100                 105                 110

Thr Leu Val Thr Val Ser Ser
        115
```

<210> SEQ ID NO 40
<211> LENGTH: 119
<212> TYPE: PRT
<213> ORGANISM: Artificial Sequence
<220> FEATURE:
<223> OTHER INFORMATION: Synthetic peptide

<400> SEQUENCE: 40

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
             20                  25                  30

Gly Met Ser Trp Val Arg Gln Ala Pro Gly Lys Gly Leu Glu Trp Val
         35                  40                  45

Ser Thr Ile Ser Ser Ala Ser Thr Tyr Ser Tyr Tyr Pro Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Gly Arg His Ser Asp Gly Asn Phe Ala Phe Gly Tyr Trp Gly Gln Gly
            100                 105                 110

Thr Leu Val Thr Val Ser Ser
        115
```

<210> SEQ ID NO 41
<211> LENGTH: 119
<212> TYPE: PRT
<213> ORGANISM: Artificial Sequence
<220> FEATURE:
<223> OTHER INFORMATION: Synthetic peptide

<400> SEQUENCE: 41

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Ile Phe Ser Asn Tyr
            20                  25                  30

Gly Met Ser Trp Val Arg Gln Ala Pro Gly Lys Gly Leu Glu Trp Val
        35                  40                  45

Ser Thr Ile Ser Ser Ala Ser Thr Tyr Ser Tyr Tyr Pro Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Gly Arg His Ser Asp Gly Asn Phe Ala Phe Gly Tyr Trp Gly Gln Gly
            100                 105                 110

Thr Leu Val Thr Val Ser Ser
        115
```

<210> SEQ ID NO 42
<211> LENGTH: 97
<212> TYPE: DNA
<213> ORGANISM: Artificial Sequence
<220> FEATURE:
<223> OTHER INFORMATION: Synthetic DNA

<400> SEQUENCE: 42

```
gtgaatccag aggctgcaca ggagagtctc agggaccccc caggctgtac caagcctccc     60

ccagactcca ccagctgcac ctcacactgg acacctt                              97
```

<210> SEQ ID NO 43
<211> LENGTH: 98
<212> TYPE: DNA
<213> ORGANISM: Artificial Sequence
<220> FEATURE:
<223> OTHER INFORMATION: Synthetic DNA

<400> SEQUENCE: 43

```
tgtgcagcct ctggattcac cttcagtaat tatggcatgt cttgggtccg ccaggctcca     60

gggaaggggc tggagtgggt ctcaaccatt agtagtgc                             98
```

<210> SEQ ID NO 44
<211> LENGTH: 98
<212> TYPE: DNA
<213> ORGANISM: Artificial Sequence
<220> FEATURE:
<223> OTHER INFORMATION: Synthetic DNA

<400> SEQUENCE: 44

```
acagcgtgtt cttggaattg tctctggaga tggtgaatcg tcccttcaca ctgtctggat     60

aataggaata agtgctagca ctactaatgg ttgagacc                             98
```

<210> SEQ ID NO 45
<211> LENGTH: 98
<212> TYPE: DNA
<213> ORGANISM: Artificial Sequence
<220> FEATURE:
<223> OTHER INFORMATION: Synthetic DNA

<400> SEQUENCE: 45

```
acaattccaa gaacacgctg tatctgcaga tgaacagcct gagagccgag gacacggccg     60
```

-continued

```
tgtattactg tgcgagacat agcgatggaa acttcgcg                          98


<210> SEQ ID NO 46
<211> LENGTH: 98
<212> TYPE: DNA
<213> ORGANISM: Artificial Sequence
<220> FEATURE:
<223> OTHER INFORMATION: Synthetic DNA

<400> SEQUENCE: 46

tgtgcagcct ctggattcat tttcagtaat tatggcatgt cttgggtccg ccaggctcca     60

gggaaggggc tggagtgggt ctcaaccatt agtagtgc                          98


<210> SEQ ID NO 47
<211> LENGTH: 98
<212> TYPE: DNA
<213> ORGANISM: Artificial Sequence
<220> FEATURE:
<223> OTHER INFORMATION: Synthetic DNA

<400> SEQUENCE: 47

acaattccaa gaacacgctg tatctgcaga tgaacagcct gagagccgag gacacggccg     60

tgtattactg tggaagacat agcgatggaa acttcgcg                          98


<210> SEQ ID NO 48
<211> LENGTH: 360
<212> TYPE: PRT
<213> ORGANISM: Homo sapiens

<400> SEQUENCE: 48

Met Asn Pro Thr Asp Ile Ala Asp Thr Thr Leu Asp Glu Ser Ile Tyr
  1               5                  10                  15

Ser Asn Tyr Tyr Leu Tyr Glu Ser Ile Pro Lys Pro Cys Thr Lys Glu
             20                  25                  30

Gly Ile Lys Ala Phe Gly Glu Leu Phe Leu Pro Pro Leu Tyr Ser Leu
         35                  40                  45

Val Phe Val Phe Gly Leu Leu Gly Asn Ser Val Val Val Leu Val Leu
     50                  55                  60

Phe Lys Tyr Lys Arg Leu Arg Ser Met Thr Asp Val Tyr Leu Leu Asn
 65                  70                  75                  80

Leu Ala Ile Ser Asp Leu Leu Phe Val Phe Ser Leu Pro Phe Trp Gly
                 85                  90                  95

Tyr Tyr Ala Ala Asp Gln Trp Val Phe Gly Leu Gly Leu Cys Lys Met
            100                 105                 110

Ile Ser Trp Met Tyr Leu Val Gly Phe Tyr Ser Gly Ile Phe Phe Val
        115                 120                 125

Met Leu Met Ser Ile Asp Arg Tyr Leu Ala Ile Val His Ala Val Phe
    130                 135                 140

Ser Leu Arg Ala Arg Thr Leu Thr Tyr Gly Val Ile Thr Ser Leu Ala
145                 150                 155                 160

Thr Trp Ser Val Ala Val Phe Ala Ser Leu Pro Gly Phe Leu Phe Ser
                165                 170                 175

Thr Cys Tyr Thr Glu Arg Asn His Thr Tyr Cys Lys Thr Lys Tyr Ser
            180                 185                 190

Leu Asn Ser Thr Thr Trp Lys Val Leu Ser Ser Leu Glu Ile Asn Ile
        195                 200                 205

Leu Gly Leu Val Ile Pro Leu Gly Ile Met Leu Phe Cys Tyr Ser Met
    210                 215                 220
```

-continued

```
Ile Ile Arg Thr Leu Gln His Cys Lys Asn Glu Lys Lys Asn Lys Ala
225                 230                 235                 240

Val Lys Met Ile Phe Ala Val Val Val Leu Phe Leu Gly Phe Trp Thr
                245                 250                 255

Pro Tyr Asn Ile Val Leu Phe Leu Glu Thr Leu Val Glu Leu Glu Val
            260                 265                 270

Leu Gln Asp Cys Thr Phe Glu Arg Tyr Leu Asp Tyr Ala Ile Gln Ala
        275                 280                 285

Thr Glu Thr Leu Ala Phe Val His Cys Cys Leu Asn Pro Ile Ile Tyr
    290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
                325                 330                 335

Ile Tyr Ser Ala Asp Thr Pro Ser Ser Ser Tyr Thr Gln Ser Thr Met
            340                 345                 350

Asp His Asp Leu His Asp Ala Leu
        355                 360


<210> SEQ ID NO 49
<211> LENGTH: 357
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(357)

<400> SEQUENCE: 49

gag gtg cag ctg gtg gag tct ggg gga gac ttg gta cag cct ggg agg       48
Glu Val Gln Leu Val Glu Ser Gly Gly Asp Leu Val Gln Pro Gly Arg
  1               5                  10                  15

tcc ctg aga ctc tcc tgt gca gcc tct gga ttc att ttc agt aat tat       96
Ser Leu Arg Leu Ser Cys Ala Ala Ser Gly Phe Ile Phe Ser Asn Tyr
             20                  25                  30

ggc atg tct tgg gtc cgc cag gct cca ggg aag ggg ctg gag tgg gtc      144
Gly Met Ser Trp Val Arg Gln Ala Pro Gly Lys Gly Leu Glu Trp Val
         35                  40                  45

gca acc att agt agt gct agc act tat tcc tat tat cca gac agt gtg      192
Ala Thr Ile Ser Ser Ala Ser Thr Tyr Ser Tyr Tyr Pro Asp Ser Val
     50                  55                  60

aag gga cga ttc acc atc tcc aga gac aat gcc aag aac tcc ctg tat      240
Lys Gly Arg Phe Thr Ile Ser Arg Asp Asn Ala Lys Asn Ser Leu Tyr
 65                  70                  75                  80

ctg cag atg aac agc ctg aga gtc gag gac acg gcc ctg tat tac tgt      288
Leu Gln Met Asn Ser Leu Arg Val Glu Asp Thr Ala Leu Tyr Tyr Cys
                 85                  90                  95

gcg aga cat agc gat gga aac ttc gcg ttt ggt tat tgg ggc cag gga      336
Ala Arg His Ser Asp Gly Asn Phe Ala Phe Gly Tyr Trp Gly Gln Gly
            100                 105                 110

acc ctg gtc acc gtc tcc tca                                          357
Thr Leu Val Thr Val Ser Ser
        115


<210> SEQ ID NO 50
<211> LENGTH: 357
<212> TYPE: DNA
<213> ORGANISM: Artificial Sequence
<220> FEATURE:
```

-continued

```
<223> OTHER INFORMATION: Synthetic DNA
<220> FEATURE:
<221> NAME/KEY: CDS
<222> LOCATION: (1)..(357)

<400> SEQUENCE: 50

gag gtg cag ctg gtg gag tct ggg gga gac ttg gta cag cct ggg agg       48
Glu Val Gln Leu Val Glu Ser Gly Gly Asp Leu Val Gln Pro Gly Arg
  1               5                  10                  15

tcc ctg aga ctc tcc tgt gca gcc tct gga ttc att ttc agt aat tat       96
Ser Leu Arg Leu Ser Cys Ala Ala Ser Gly Phe Ile Phe Ser Asn Tyr
             20                  25                  30

ggc atg tct tgg gtc cgc cag gct cca ggg aag ggg ctg gag tgg gtc      144
Gly Met Ser Trp Val Arg Gln Ala Pro Gly Lys Gly Leu Glu Trp Val
         35                  40                  45

gca acc att agt agt gct agc act tat tcc tat tat cca gac agt gtg      192
Ala Thr Ile Ser Ser Ala Ser Thr Tyr Ser Tyr Tyr Pro Asp Ser Val
     50                  55                  60

aag gga cga ttc acc atc tcc aga gac aat gcc aag aac tcc ctg tat      240
Lys Gly Arg Phe Thr Ile Ser Arg Asp Asn Ala Lys Asn Ser Leu Tyr
 65                  70                  75                  80

ctg cag atg aac agc ctg aga gtc gag gac acg gcc ctg tat tac tgt      288
Leu Gln Met Asn Ser Leu Arg Val Glu Asp Thr Ala Leu Tyr Tyr Cys
                 85                  90                  95

gga aga cat agc gat gga aac ttc gcg ttt ggt tat tgg ggc cag gga      336
Gly Arg His Ser Asp Gly Asn Phe Ala Phe Gly Tyr Trp Gly Gln Gly
            100                 105                 110

acc ctg gtc acc gtc tcc tca                                          357
Thr Leu Val Thr Val Ser Ser
        115


<210> SEQ ID NO 51
<211> LENGTH: 357
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(357)

<400> SEQUENCE: 51

gag gtg cag ctg gtg gag tct ggg gga gac ttg gta cag cct ggg agg       48
Glu Val Gln Leu Val Glu Ser Gly Gly Asp Leu Val Gln Pro Gly Arg
  1               5                  10                  15

tcc ctg aga ctc tcc tgt gca gcc tct gga ttc att ttc agt aat tat       96
Ser Leu Arg Leu Ser Cys Ala Ala Ser Gly Phe Ile Phe Ser Asn Tyr
             20                  25                  30

ggc atg tct tgg gtc cgc cag gct cca gac aag agg ctg gag tgg gtc      144
Gly Met Ser Trp Val Arg Gln Ala Pro Asp Lys Arg Leu Glu Trp Val
         35                  40                  45

gca acc att agt agt gct agc act tat tcc tat tat cca gac agt gtg      192
Ala Thr Ile Ser Ser Ala Ser Thr Tyr Ser Tyr Tyr Pro Asp Ser Val
     50                  55                  60

aag gga cga ttc acc atc tcc aga gac aat gcc aag aac tcc ctg tat      240
Lys Gly Arg Phe Thr Ile Ser Arg Asp Asn Ala Lys Asn Ser Leu Tyr
 65                  70                  75                  80

ctg cag atg aac agc ctg aga gtc gag gac acg gcc ctg tat tac tgt      288
Leu Gln Met Asn Ser Leu Arg Val Glu Asp Thr Ala Leu Tyr Tyr Cys
                 85                  90                  95

gcg aga cat agc gat gga aac ttc gcg ttt ggt tat tgg ggc cag gga      336
Ala Arg His Ser Asp Gly Asn Phe Ala Phe Gly Tyr Trp Gly Gln Gly
            100                 105                 110
```

-continued

```
acc ctg gtc acc gtc tcc tca                                      357
Thr Leu Val Thr Val Ser Ser
        115


<210> SEQ ID NO 52
<211> LENGTH: 357
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(357)

<400> SEQUENCE: 52

gag gtg cag ctg gtg gag tct ggg gga gac ttg gta cag cct ggg agg       48
Glu Val Gln Leu Val Glu Ser Gly Gly Asp Leu Val Gln Pro Gly Arg
  1               5                  10                  15

tcc ctg aga ctc tcc tgt gca gcc tct gga ttc att ttc agt aat tat       96
Ser Leu Arg Leu Ser Cys Ala Ala Ser Gly Phe Ile Phe Ser Asn Tyr
             20                  25                  30

ggc atg tct tgg gtc cgc cag gct cca gac aag agg ctg gag tgg gtc      144
Gly Met Ser Trp Val Arg Gln Ala Pro Asp Lys Arg Leu Glu Trp Val
         35                  40                  45

gca acc att agt agt gct agc act tat tcc tat tat cca gac agt gtg      192
Ala Thr Ile Ser Ser Ala Ser Thr Tyr Ser Tyr Tyr Pro Asp Ser Val
     50                  55                  60

aag gga cga ttc acc atc tcc aga gac aat gcc aag aac tcc ctg tat      240
Lys Gly Arg Phe Thr Ile Ser Arg Asp Asn Ala Lys Asn Ser Leu Tyr
 65                  70                  75                  80

ctg cag atg aac agc ctg aga gtc gag gac acg gcc ctg tat tac tgt      288
Leu Gln Met Asn Ser Leu Arg Val Glu Asp Thr Ala Leu Tyr Tyr Cys
                 85                  90                  95

gga aga cat agc gat gga aac ttc gcg ttt ggt tat tgg ggc cag gga      336
Gly Arg His Ser Asp Gly Asn Phe Ala Phe Gly Tyr Trp Gly Gln Gly
            100                 105                 110

acc ctg gtc acc gtc tcc tca                                          357
Thr Leu Val Thr Val Ser Ser
        115


<210> SEQ ID NO 53
<211> LENGTH: 336
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(336)

<400> SEQUENCE: 53

gat atc gtg atg act cag tct cca ctc tcc ctg ccc gtc acc cct gga       48
Asp Ile Val Met Thr Gln Ser Pro Leu Ser Leu Pro Val Thr Pro Gly
  1               5                  10                  15

gag ccg gcc tcc atc tcc tgc aga tct agt cgg aac att gtt cat att       96
Glu Pro Ala Ser Ile Ser Cys Arg Ser Ser Arg Asn Ile Val His Ile
             20                  25                  30

aat ggt gac aca tat tta gaa tgg tac ctg cag aag cca ggc cag tct      144
Asn Gly Asp Thr Tyr Leu Glu Trp Tyr Leu Gln Lys Pro Gly Gln Ser
         35                  40                  45

cca cag ctc ctg atc tat aaa gtt tcc aac cga ttt tct ggg gtc cca      192
Pro Gln Leu Leu Ile Tyr Lys Val Ser Asn Arg Phe Ser Gly Val Pro
     50                  55                  60
```

-continued

```
gac agg ttc agt ggc agt ggg tca ggc aca gat ttc aca ctg aaa atc      240
Asp Arg Phe Ser Gly Ser Gly Ser Gly Thr Asp Phe Thr Leu Lys Ile
 65                  70                  75                  80

agc aga gtg gag gct gag gat gtt ggg gtt tat tac tgc ttt caa ggt      288
Ser Arg Val Glu Ala Glu Asp Val Gly Val Tyr Tyr Cys Phe Gln Gly
                 85                  90                  95

tca ctt ctt ccg tgg acg ttc ggc caa ggg acc aag gtg gaa atc aaa      336
Ser Leu Leu Pro Trp Thr Phe Gly Gln Gly Thr Lys Val Glu Ile Lys
            100                 105                 110


<210> SEQ ID NO 54
<211> LENGTH: 336
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(336)

<400> SEQUENCE: 54

gat gtt gtg atg act cag tct cca ctc tcc ctg ccc gtc acc cct gga       48
Asp Val Val Met Thr Gln Ser Pro Leu Ser Leu Pro Val Thr Pro Gly
  1               5                  10                  15

gag ccg gcc tcc atc tcc tgc aga tct agt cgg aac att gtt cat att       96
Glu Pro Ala Ser Ile Ser Cys Arg Ser Ser Arg Asn Ile Val His Ile
             20                  25                  30

aat ggt gac aca tat tta gaa tgg tac ctg cag aag cca ggc cag tct      144
Asn Gly Asp Thr Tyr Leu Glu Trp Tyr Leu Gln Lys Pro Gly Gln Ser
         35                  40                  45

cca cag ctc ctg atc tat aaa gtt tcc aac cga ttt tct ggg gtc cca      192
Pro Gln Leu Leu Ile Tyr Lys Val Ser Asn Arg Phe Ser Gly Val Pro
     50                  55                  60

gac agg ttc agt ggc agt ggg tca ggc aca gat ttc aca ctg aaa atc      240
Asp Arg Phe Ser Gly Ser Gly Ser Gly Thr Asp Phe Thr Leu Lys Ile
 65                  70                  75                  80

agc aga gtg gag gct gag gat gtt ggg gtt tat tac tgc ttt caa ggt      288
Ser Arg Val Glu Ala Glu Asp Val Gly Val Tyr Tyr Cys Phe Gln Gly
                 85                  90                  95

tca ctt ctt ccg tgg acg ttc ggc caa ggg acc aag gtg gaa atc aaa      336
Ser Leu Leu Pro Trp Thr Phe Gly Gln Gly Thr Lys Val Glu Ile Lys
            100                 105                 110


<210> SEQ ID NO 55
<211> LENGTH: 336
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(336)

<400> SEQUENCE: 55

gat atc ttg atg act cag tct cca ctc tcc ctg ccc gtc acc cct gga       48
Asp Ile Leu Met Thr Gln Ser Pro Leu Ser Leu Pro Val Thr Pro Gly
  1               5                  10                  15

gag ccg gcc tcc atc tcc tgc aga tct agt cgg aac att gtt cat att       96
Glu Pro Ala Ser Ile Ser Cys Arg Ser Ser Arg Asn Ile Val His Ile
             20                  25                  30

aat ggt gac aca tat tta gaa tgg tac ctg cag aag cca ggc cag tct      144
Asn Gly Asp Thr Tyr Leu Glu Trp Tyr Leu Gln Lys Pro Gly Gln Ser
         35                  40                  45

cca cag ctc ctg atc tat aaa gtt tcc aac cga ttt tct ggg gtc cca      192
```

-continued

```
Pro Gln Leu Leu Ile Tyr Lys Val Ser Asn Arg Phe Ser Gly Val Pro
     50                  55                  60

gac agg ttc agt ggc agt ggg tca ggc aca gat ttc aca ctg aaa atc      240
Asp Arg Phe Ser Gly Ser Gly Ser Gly Thr Asp Phe Thr Leu Lys Ile
 65                  70                  75                  80

agc aga gtg gag gct gag gat gtt ggg gtt tat tac tgc ttt caa ggt      288
Ser Arg Val Glu Ala Glu Asp Val Gly Val Tyr Tyr Cys Phe Gln Gly
                 85                  90                  95

tca ctt ctt ccg tgg acg ttc ggc caa ggg acc aag gtg gaa atc aaa      336
Ser Leu Leu Pro Trp Thr Phe Gly Gln Gly Thr Lys Val Glu Ile Lys
            100                 105                 110


<210> SEQ ID NO 56
<211> LENGTH: 336
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(336)

<400> SEQUENCE: 56

gat gtt ttg atg act cag tct cca ctc tcc ctg ccc gtc acc cct gga       48
Asp Val Leu Met Thr Gln Ser Pro Leu Ser Leu Pro Val Thr Pro Gly
  1               5                  10                  15

gag ccg gcc tcc atc tcc tgc aga tct agt cgg aac att gtt cat att       96
Glu Pro Ala Ser Ile Ser Cys Arg Ser Ser Arg Asn Ile Val His Ile
             20                  25                  30

aat ggt gac aca tat tta gaa tgg tac ctg cag aag cca ggc cag tct      144
Asn Gly Asp Thr Tyr Leu Glu Trp Tyr Leu Gln Lys Pro Gly Gln Ser
         35                  40                  45

cca cag ctc ctg atc tat aaa gtt tcc aac cga ttt tct ggg gtc cca      192
Pro Gln Leu Leu Ile Tyr Lys Val Ser Asn Arg Phe Ser Gly Val Pro
     50                  55                  60

gac agg ttc agt ggc agt ggg tca ggc aca gat ttc aca ctg aaa atc      240
Asp Arg Phe Ser Gly Ser Gly Ser Gly Thr Asp Phe Thr Leu Lys Ile
 65                  70                  75                  80

agc aga gtg gag gct gag gat gtt ggg gtt tat tac tgc ttt caa ggt      288
Ser Arg Val Glu Ala Glu Asp Val Gly Val Tyr Tyr Cys Phe Gln Gly
                 85                  90                  95

tca ctt ctt ccg tgg acg ttc ggc caa ggg acc aag gtg gaa atc aaa      336
Ser Leu Leu Pro Trp Thr Phe Gly Gln Gly Thr Lys Val Glu Ile Lys
            100                 105                 110


<210> SEQ ID NO 57
<211> LENGTH: 357
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(357)

<400> SEQUENCE: 57

gag gtg cag ctg gtg gag tct ggg gga ggc ttg gta cag cct ggg ggg       48
Glu Val Gln Leu Val Glu Ser Gly Gly Gly Leu Val Gln Pro Gly Gly
  1               5                  10                  15

tcc ctg aga ctc tcc tgt gca gcc tct gga ttc acc ttc agt aat tat       96
Ser Leu Arg Leu Ser Cys Ala Ala Ser Gly Phe Thr Phe Ser Asn Tyr
             20                  25                  30

ggc atg tct tgg gtc cgc cag gct cca ggg aag ggg ctg gag tgg gtc      144
Gly Met Ser Trp Val Arg Gln Ala Pro Gly Lys Gly Leu Glu Trp Val
```

-continued

```
         35                  40                  45

tca acc att agt agt gct agc act tat tcc tat tat cca gac agt gtg      192
Ser Thr Ile Ser Ser Ala Ser Thr Tyr Ser Tyr Tyr Pro Asp Ser Val
     50                  55                  60

aag gga cga ttc acc atc tcc aga gac aat tcc aag aac acg ctg tat      240
Lys Gly Arg Phe Thr Ile Ser Arg Asp Asn Ser Lys Asn Thr Leu Tyr
 65                  70                  75                  80

ctg cag atg aac agc ctg aga gcc gag gac acg gcc gtg tat tac tgt      288
Leu Gln Met Asn Ser Leu Arg Ala Glu Asp Thr Ala Val Tyr Tyr Cys
                 85                  90                  95

gcg aga cat agc gat gga aac ttc gcg ttt ggt tat tgg ggc cag gga      336
Ala Arg His Ser Asp Gly Asn Phe Ala Phe Gly Tyr Trp Gly Gln Gly
            100                 105                 110

acc ctg gtc acc gtc tcc tca                                          357
Thr Leu Val Thr Val Ser Ser
        115
```

<210> SEQ ID NO 58
<211> LENGTH: 357
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(357)

<400> SEQUENCE: 58

```
gag gtg cag ctg gtg gag tct ggg gga ggc ttg gta cag cct ggg ggg       48
Glu Val Gln Leu Val Glu Ser Gly Gly Gly Leu Val Gln Pro Gly Gly
  1               5                  10                  15

tcc ctg aga ctc tcc tgt gca gcc tct gga ttc att ttc agt aat tat       96
Ser Leu Arg Leu Ser Cys Ala Ala Ser Gly Phe Ile Phe Ser Asn Tyr
             20                  25                  30

ggc atg tct tgg gtc cgc cag gct cca ggg aag ggg ctg gag tgg gtc      144
Gly Met Ser Trp Val Arg Gln Ala Pro Gly Lys Gly Leu Glu Trp Val
         35                  40                  45

tca acc att agt agt gct agc act tat tcc tat tat cca gac agt gtg      192
Ser Thr Ile Ser Ser Ala Ser Thr Tyr Ser Tyr Tyr Pro Asp Ser Val
     50                  55                  60

aag gga cga ttc acc atc tcc aga gac aat tcc aag aac acg ctg tat      240
Lys Gly Arg Phe Thr Ile Ser Arg Asp Asn Ser Lys Asn Thr Leu Tyr
 65                  70                  75                  80

ctg cag atg aac agc ctg aga gcc gag gac acg gcc gtg tat tac tgt      288
Leu Gln Met Asn Ser Leu Arg Ala Glu Asp Thr Ala Val Tyr Tyr Cys
                 85                  90                  95

gcg aga cat agc gat gga aac ttc gcg ttt ggt tat tgg ggc cag gga      336
Ala Arg His Ser Asp Gly Asn Phe Ala Phe Gly Tyr Trp Gly Gln Gly
            100                 105                 110

acc ctg gtc acc gtc tcc tca                                          357
Thr Leu Val Thr Val Ser Ser
        115
```

<210> SEQ ID NO 59
<211> LENGTH: 357
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(357)

<400> SEQUENCE: 59

-continued

```
gag gtg cag ctg gtg gag tct ggg gga ggc ttg gta cag cct ggg ggg       48
Glu Val Gln Leu Val Glu Ser Gly Gly Gly Leu Val Gln Pro Gly Gly
  1               5                  10                  15

tcc ctg aga ctc tcc tgt gca gcc tct gga ttc acc ttc agt aat tat       96
Ser Leu Arg Leu Ser Cys Ala Ala Ser Gly Phe Thr Phe Ser Asn Tyr
             20                  25                  30

ggc atg tct tgg gtc cgc cag gct cca ggg aag ggg ctg gag tgg gtc      144
Gly Met Ser Trp Val Arg Gln Ala Pro Gly Lys Gly Leu Glu Trp Val
         35                  40                  45

tca acc att agt agt gct agc act tat tcc tat tat cca gac agt gtg      192
Ser Thr Ile Ser Ser Ala Ser Thr Tyr Ser Tyr Tyr Pro Asp Ser Val
     50                  55                  60

aag gga cga ttc acc atc tcc aga gac aat tcc aag aac acg ctg tat      240
Lys Gly Arg Phe Thr Ile Ser Arg Asp Asn Ser Lys Asn Thr Leu Tyr
 65                  70                  75                  80

ctg cag atg aac agc ctg aga gcc gag gac acg gcc gtg tat tac tgt      288
Leu Gln Met Asn Ser Leu Arg Ala Glu Asp Thr Ala Val Tyr Tyr Cys
                 85                  90                  95

gga aga cat agc gat gga aac ttc gcg ttt ggt tat tgg ggc cag gga      336
Gly Arg His Ser Asp Gly Asn Phe Ala Phe Gly Tyr Trp Gly Gln Gly
            100                 105                 110

acc ctg gtc acc gtc tcc tca                                          357
Thr Leu Val Thr Val Ser Ser
        115
```

<210> SEQ ID NO 60
<211> LENGTH: 357
<212> TYPE: DNA
<213> ORGANISM: Artificial Sequence
<220> FEATURE:
<223> OTHER INFORMATION: Synthetic DNA
<220> FEATURE:
<221> NAME/KEY: CDS
<222> LOCATION: (1)..(357)

<400> SEQUENCE: 60

```
gag gtg cag ctg gtg gag tct ggg gga ggc ttg gta cag cct ggg ggg       48
Glu Val Gln Leu Val Glu Ser Gly Gly Gly Leu Val Gln Pro Gly Gly
  1               5                  10                  15

tcc ctg aga ctc tcc tgt gca gcc tct gga ttc att ttc agt aat tat       96
Ser Leu Arg Leu Ser Cys Ala Ala Ser Gly Phe Ile Phe Ser Asn Tyr
             20                  25                  30

ggc atg tct tgg gtc cgc cag gct cca ggg aag ggg ctg gag tgg gtc      144
Gly Met Ser Trp Val Arg Gln Ala Pro Gly Lys Gly Leu Glu Trp Val
         35                  40                  45

tca acc att agt agt gct agc act tat tcc tat tat cca gac agt gtg      192
Ser Thr Ile Ser Ser Ala Ser Thr Tyr Ser Tyr Tyr Pro Asp Ser Val
     50                  55                  60

aag gga cga ttc acc atc tcc aga gac aat tcc aag aac acg ctg tat      240
Lys Gly Arg Phe Thr Ile Ser Arg Asp Asn Ser Lys Asn Thr Leu Tyr
 65                  70                  75                  80

ctg cag atg aac agc ctg aga gcc gag gac acg gcc gtg tat tac tgt      288
Leu Gln Met Asn Ser Leu Arg Ala Glu Asp Thr Ala Val Tyr Tyr Cys
                 85                  90                  95

gga aga cat agc gat gga aac ttc gcg ttt ggt tat tgg ggc cag gga      336
Gly Arg His Ser Asp Gly Asn Phe Ala Phe Gly Tyr Trp Gly Gln Gly
            100                 105                 110

acc ctg gtc acc gtc tcc tca                                          357
Thr Leu Val Thr Val Ser Ser
        115
```

-continued

<210> SEQ ID NO 61
<211> LENGTH: 414
<212> TYPE: DNA
<213> ORGANISM: Mus musculus
<220> FEATURE:
<221> NAME/KEY: CDS
<222> LOCATION: (1)..(414)

<400> SEQUENCE: 61

```
atg aac ctc ggg ctc agt ttg att ttc ctt gcc ctc att tta aaa ggt       48
Met Asn Leu Gly Leu Ser Leu Ile Phe Leu Ala Leu Ile Leu Lys Gly
  1               5                  10                  15

gtc cag tgt gag gtg cag ctg gtg gag tct ggg gga gac tta atg aag       96
Val Gln Cys Glu Val Gln Leu Val Glu Ser Gly Gly Asp Leu Met Lys
             20                  25                  30

cct gga ggg tcc ctg aaa atc tcc tgt gca gcc tct gga ttc att ttc      144
Pro Gly Gly Ser Leu Lys Ile Ser Cys Ala Ala Ser Gly Phe Ile Phe
         35                  40                  45

agt aat tat ggc atg tct tgg gtt cgc cag act cca gac atg agg ctg      192
Ser Asn Tyr Gly Met Ser Trp Val Arg Gln Thr Pro Asp Met Arg Leu
     50                  55                  60

gaa tgg gtc gca acc att agt agt gct agt act tat tcc tat tat cca      240
Glu Trp Val Ala Thr Ile Ser Ser Ala Ser Thr Tyr Ser Tyr Tyr Pro
 65                  70                  75                  80

gac agt gtg aag gga cga ttc acc ata tcc agg gac aac gcc gag aac      288
Asp Ser Val Lys Gly Arg Phe Thr Ile Ser Arg Asp Asn Ala Glu Asn
                 85                  90                  95

tcc cta tat ctg caa atg aat agt ctg agg tct gag gac aca ggc ata      336
Ser Leu Tyr Leu Gln Met Asn Ser Leu Arg Ser Glu Asp Thr Gly Ile
            100                 105                 110

tat tac tgt gga aga cat agc gat gga aac ttc gcg ttt ggt tat tgg      384
Tyr Tyr Cys Gly Arg His Ser Asp Gly Asn Phe Ala Phe Gly Tyr Trp
        115                 120                 125

ggc cga ggg act ctg gtc act gtc tct gca                              414
Gly Arg Gly Thr Leu Val Thr Val Ser Ala
    130                 135
```

<210> SEQ ID NO 62
<211> LENGTH: 138
<212> TYPE: PRT
<213> ORGANISM: Mus musculus

<400> SEQUENCE: 62

```
Met Asn Leu Gly Leu Ser Leu Ile Phe Leu Ala Leu Ile Leu Lys Gly
  1               5                  10                  15

Val Gln Cys Glu Val Gln Leu Val Glu Ser Gly Gly Asp Leu Met Lys
             20                  25                  30

Pro Gly Gly Ser Leu Lys Ile Ser Cys Ala Ala Ser Gly Phe Ile Phe
         35                  40                  45

Ser Asn Tyr Gly Met Ser Trp Val Arg Gln Thr Pro Asp Met Arg Leu
     50                  55                  60

Glu Trp Val Ala Thr Ile Ser Ser Ala Ser Thr Tyr Ser Tyr Tyr Pro
 65                  70                  75                  80

Asp Ser Val Lys Gly Arg Phe Thr Ile Ser Arg Asp Asn Ala Glu Asn
                 85                  90                  95

Ser Leu Tyr Leu Gln Met Asn Ser Leu Arg Ser Glu Asp Thr Gly Ile
            100                 105                 110

Tyr Tyr Cys Gly Arg His Ser Asp Gly Asn Phe Ala Phe Gly Tyr Trp
        115                 120                 125

Gly Arg Gly Thr Leu Val Thr Val Ser Ala
```

-continued

```
    130                 135


<210> SEQ ID NO 63
<211> LENGTH: 396
<212> TYPE: DNA
<213> ORGANISM: Mus musculus
<220> FEATURE:
<221> NAME/KEY: CDS
<222> LOCATION: (1)..(396)

<400> SEQUENCE: 63

atg aag ttg cct gtt agg ctg ttg gtg ctg atg ttc tgg att cct gct        48
Met Lys Leu Pro Val Arg Leu Leu Val Leu Met Phe Trp Ile Pro Ala
  1               5                  10                  15

tcc agc agt gat gtt ttg atg acc caa act cca ctc tcc ctg cct gtc        96
Ser Ser Ser Asp Val Leu Met Thr Gln Thr Pro Leu Ser Leu Pro Val
             20                  25                  30

agt ctt gga gat caa gcc tcc atc tct tgc aga tct agt cgg aac att       144
Ser Leu Gly Asp Gln Ala Ser Ile Ser Cys Arg Ser Ser Arg Asn Ile
         35                  40                  45

gtt cat att aat ggt gac aca tat tta gaa tgg tac ctg cag aga ccg       192
Val His Ile Asn Gly Asp Thr Tyr Leu Glu Trp Tyr Leu Gln Arg Pro
     50                  55                  60

ggc cag tct cca aag ctc cta atc tac aaa gtt tcc aac cga ttt tct       240
Gly Gln Ser Pro Lys Leu Leu Ile Tyr Lys Val Ser Asn Arg Phe Ser
 65                  70                  75                  80

ggg gtc cca gac agg ttc agt ggc agt gga tca ggg aca gat ttc aca       288
Gly Val Pro Asp Arg Phe Ser Gly Ser Gly Ser Gly Thr Asp Phe Thr
                 85                  90                  95

ctc aag atc agc aga gtg gag gct gag gat ctg gga gtt tat tac tgc       336
Leu Lys Ile Ser Arg Val Glu Ala Glu Asp Leu Gly Val Tyr Tyr Cys
            100                 105                 110

ttt caa ggt tca ctt ctt ccg tgg acg ttc ggt gga ggc acc agg ctg       384
Phe Gln Gly Ser Leu Leu Pro Trp Thr Phe Gly Gly Gly Thr Arg Leu
        115                 120                 125

gaa atc aga cgg                                                       396
Glu Ile Arg Arg
    130


<210> SEQ ID NO 64
<211> LENGTH: 132
<212> TYPE: PRT
<213> ORGANISM: Mus musculus

<400> SEQUENCE: 64

Met Lys Leu Pro Val Arg Leu Leu Val Leu Met Phe Trp Ile Pro Ala
  1               5                  10                  15

Ser Ser Ser Asp Val Leu Met Thr Gln Thr Pro Leu Ser Leu Pro Val
             20                  25                  30

Ser Leu Gly Asp Gln Ala Ser Ile Ser Cys Arg Ser Ser Arg Asn Ile
         35                  40                  45

Val His Ile Asn Gly Asp Thr Tyr Leu Glu Trp Tyr Leu Gln Arg Pro
     50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Tyr Cys
            100                 105                 110

Phe Gln Gly Ser Leu Leu Pro Trp Thr Phe Gly Gly Gly Thr Arg Leu
```

-continued 115 120 125

Glu Ile Arg Arg
130

<210> SEQ ID NO 65
<211> LENGTH: 39
<212> TYPE: DNA
<213> ORGANISM: Artificial Sequence
<220> FEATURE:
<223> OTHER INFORMATION: Synthetic DNA

<400> SEQUENCE: 65
aaggaaaaaa gcggccgcga cccctcacca tgaacctcg 39

<210> SEQ ID NO 66
<211> LENGTH: 39
<212> TYPE: DNA
<213> ORGANISM: Artificial Sequence
<220> FEATURE:
<223> OTHER INFORMATION: Synthetic DNA

<400> SEQUENCE: 66
cgatgggccc ttggtggagg ctgcagagac agtgaccag 39

<210> SEQ ID NO 67
<211> LENGTH: 31
<212> TYPE: DNA
<213> ORGANISM: Artificial Sequence
<220> FEATURE:
<223> OTHER INFORMATION: Synthetic DNA

<400> SEQUENCE: 67
ccggaattcg cctcctcaaa atgaagttgc c 31

<210> SEQ ID NO 68
<211> LENGTH: 31
<212> TYPE: DNA
<213> ORGANISM: Artificial Sequence
<220> FEATURE:
<223> OTHER INFORMATION: Synthetic DNA

<400> SEQUENCE: 68
agccaccgta cgtctgattt ccagcctggt g 31

<210> SEQ ID NO 69
<211> LENGTH: 97
<212> TYPE: DNA
<213> ORGANISM: Artificial Sequence
<220> FEATURE:
<223> OTHER INFORMATION: Synthetic DNA

<400> SEQUENCE: 69
atgaatccag aggctgcaca ggagagtctc agggaccccc caggctgtac caagcctccc 60
ccagactcca ccagctgcac ctcacactgg acacctt 97

<210> SEQ ID NO 70
<211> LENGTH: 28
<212> TYPE: PRT
<213> ORGANISM: Artificial sequence
<220> FEATURE:
<223> OTHER INFORMATION: Synthetic peptide

<400> SEQUENCE: 70

Asn Pro Thr Asp Ile Ala Asp Thr Thr Leu Asp Glu Ser Ile Tyr Ser
1 5 10 15

-continued

```
Asn Tyr Tyr Leu Tyr Glu Ser Ile Pro Lys Pro Cys
            20                  25


<210> SEQ ID NO 71
<211> LENGTH: 18
<212> TYPE: PRT
<213> ORGANISM: Artificial sequence
<220> FEATURE:
<223> OTHER INFORMATION: Synthetic peptide

<400> SEQUENCE: 71

Asp Glu Ser Ile Tyr Ser Asn Tyr Tyr Leu Tyr Glu Ser Ile Pro Lys
  1               5                  10                  15

Pro Cys


<210> SEQ ID NO 72
<211> LENGTH: 17
<212> TYPE: PRT
<213> ORGANISM: Artificial sequence
<220> FEATURE:
<223> OTHER INFORMATION: Synthetic peptide

<400> SEQUENCE: 72

Glu Ser Ile Tyr Ser Asn Tyr Tyr Leu Tyr Glu Ser Ile Pro Lys Pro
  1               5                  10                  15

Cys


<210> SEQ ID NO 73
<211> LENGTH: 16
<212> TYPE: PRT
<213> ORGANISM: Artificial sequence
<220> FEATURE:
<223> OTHER INFORMATION: Synthetic peptide

<400> SEQUENCE: 73

Ser Ile Tyr Ser Asn Tyr Tyr Leu Tyr Glu Ser Ile Pro Lys Pro Cys
  1               5                  10                  15


<210> SEQ ID NO 74
<211> LENGTH: 15
<212> TYPE: PRT
<213> ORGANISM: Artificial sequence
<220> FEATURE:
<223> OTHER INFORMATION: Synthetic peptide

<400> SEQUENCE: 74

Ile Tyr Ser Asn Tyr Tyr Leu Tyr Glu Ser Ile Pro Lys Pro Cys
  1               5                  10                  15


<210> SEQ ID NO 75
<211> LENGTH: 14
<212> TYPE: PRT
<213> ORGANISM: Artificial sequence
<220> FEATURE:
<223> OTHER INFORMATION: Synthetic peptide

<400> SEQUENCE: 75

Glu Ser Ile Tyr Ser Asn Tyr Tyr Leu Tyr Glu Ser Ile Cys
  1               5                  10


<210> SEQ ID NO 76
<211> LENGTH: 13
<212> TYPE: PRT
<213> ORGANISM: Artificial sequence
<220> FEATURE:
```

-continued

```
<223> OTHER INFORMATION: Synthetic peptide

<400> SEQUENCE: 76

Glu Ser Ile Tyr Ser Asn Tyr Tyr Leu Tyr Glu Ser Cys
  1               5                  10


<210> SEQ ID NO 77
<211> LENGTH: 12
<212> TYPE: PRT
<213> ORGANISM: Artificial sequence
<220> FEATURE:
<223> OTHER INFORMATION: Synthetic peptide

<400> SEQUENCE: 77

Glu Ser Ile Tyr Ser Asn Tyr Tyr Leu Tyr Glu Cys
  1               5                  10


<210> SEQ ID NO 78
<211> LENGTH: 11
<212> TYPE: PRT
<213> ORGANISM: Artificial sequence
<220> FEATURE:
<223> OTHER INFORMATION: Synthetic peptide

<400> SEQUENCE: 78

Glu Ser Ile Tyr Ser Asn Tyr Tyr Leu Tyr Cys
  1               5                  10
```

HUMAN CDR-GRAFTED ANTIBODY AND ANTIBODY FRAGMENT THEREOF

BACKGROUND OF THE INVENTION

1. Field of the Invention

The present invention relates to a human CDR-grafted antibody which specifically reacts with the extracellular region of human CC chemokine receptor 4 (hereinafter referred to as "CCR4") but does not react with a blood platelet and the antibody fragment thereof Furthermore, the present invention relates to a human CDR-grafted antibody which specifically reacts with the extracellular region of human CCR4 but does not have an inhibiting activity of a CCR4 ligand such as TARC or MDC binding to CCR4 and the antibody fragment thereof. Moreover, the present invention relates to a human CDR-grafted antibody which specifically reacts with the extracellular region of CCR4, has a cytotoxic activity and an inhibiting activity of cytokine production by Th2 cells, and comprises a specific complementarity determining region (hereinafter referred to as "CDR"), and the antibody fragment thereof Also, the present invention relates to a DNA encoding the antibody or the antibody fragment thereof Furthermore, the present invention relates to a vector comprising the DNA, and a transformant transformed with the vector. Moreover, the present invention relates to a method for producing the antibody or the antibody fragment thereof using the transformant, and a medicament such as a therapeutic agent, a diagnostic agent and the like, for Th2-mediated immune diseases such as allergic diseases and the like, which comprises using the antibody or the antibody fragment thereof Additionally, the present invention relates to a medicament such as a therapeutic agent, a diagnostic agent and the like, for cancers such as blood cancers, e.g., leukemia and lymphomatosis, which comprises using the antibody or the antibody fragment thereof 2. Brief Description of the Background Art Various factors such as eosinophils, mast cells, IgE and the like, play a role in allergic diseases such as bronchial asthma. Eosinophils infiltrate into an inflammatory site and release cytotoxic basic proteins such as MBP (major basic protein) or the like by degranulation and the surrounding tissues are damaged by such cytotoxic basic proteins. Mast cells are bound to an antigen immune complex with IgE which is produced by B cells and release histamine so that an immediate allergic reaction is induced. The allergic reaction is controlled by biologically functional molecules such as cytokines, chemokines, and the like, which take part in signal transduction between cells. IL-5 induces differentiation, survival and degranulation of eosinophils. IL-4 induces B cell activation and production of IgE. IgE produced forms an immune complex with the antigen and causes degranulation of mast cells. It has been found that IL-4, IL-13 and the like are also produced by mast cells and contribute to the production of IgE by B cells (*Am. J. Respir. Crit. Care Med.*, 152, 2059 (1995), *Immunol. Today*, 15, 19 (1994)). Thus, an elaborate cytokine-chemokine network is present among inflammatory cells and keeps complicated balances.

The cytokines and chemokines are produced by helper T cells which express CD4 on the cell surface (hereinafter referred to as "CD4+Th cells"). Actually, it has been found that infiltration of helper T cells is found in the airway inflammation site of bronchial asthma patients, wherein a considerably large number of the T cells are activated and that the severity and airway hypersensitivity of asthma patient correlates with the number of activated T cells, as well as the activated T cells are also increased in the peripheral blood (*Am. Rev. Respir. Dis.*, 145, S22 (1992)).

The helper T cells are classified into Th1 cells and Th2 cells, depending on the kind of cytokine to be produced thereby (*Annu. Rev. Immunol.*, 7, 145 (1989)). Th2 cells produce IL-4, IL-5, IL-13 and the like. The cytokines produced by Th2 cells are Th2 cytokines.

It has been found that an antigen-specific T cell clone isolated from an atopic disease patient releases Th2 cytokines when stimulated in vitro (*Proc. Natl. Acad Sci., U.S.A.*, 88, 4538 (1991)), and Th2 cells are present in bronchoalveolar lavage fluid (hereinafter referred to as "BAL") and airway mucosa of asthma patients (*N. Engl. J Med.*, 326, 298 (1992), *Eur. J. Immunol.*, 23, 1445 (1993)). Expression levels of IL-4 and IL-5 mRNAs of Th2 cytokines are increased when mRNA expressions of various cytokines in cells in BAL are examined using an allergic inflammation animal model (*Clin. Immunol. Immunopathol*, 75, 75 (1995)). Also, when Th2 cells are intravenously or intranasaly administered to mice, asthmatic inflammation is induced in the lungs in antigen specific manner (*J. Exp. Med.*, 186, 1737 (1997), *J. Immunol.*, 160, 1378 (1998)) and eosinophilia is observed (*J. Immunol.*, 16 3128 (1998)). Expression of IL-5 is observed in the airway mucous of asthma patients and the skin lesions of atopic dermatitis patients (*J. Clin. Invest.*, 87 1541 (1991), *J. Erp. Med.*, 173, 775 (1991)), and the expression level of IL-5 in the mucous of chronic allergic rhinitis correlates with the expression level of IL-13, and the amounts of serum total IgE and antigen-specific IgE (*Therapeutics*, 32, 19 (1998)).

Chemokine is a general term for basic heparin-binding proteins which induce chemotoxis and activation of leukocyte, and classified into subfamilies of CXC, CC, C and $CX_3C$ depending on the position of the cysteine residues in the primary structure. 16 of chemokine receptors have been identified so far (*Curr. Opi. Immunol.,* 11, 626 (1999)), and it has been shown that expression of each chemokine receptor is different among the leukocytes such as Th 1 cell, Th2 cell or the like (*Cell Engineering*, 7,1022 (1998)).

Human CCR4 is a G protein coupled seven transmembrane receptor cloned as K5-5 from a human immature basophilic cell line KU-812. The transmembrane regions of CCR4 are considered to be positions 40 to 67, positions 78 to 97, positions 113 to 133, positions 151 to 175, positions 207 to 226, positions 243 to 270 and positions 285 to 308 in the amino acid sequence, the extracellular regions are considered to be positions 1 to 39, positions 98 to 112, positions 176 to 206 and positions 271 to 284 in the amino acid sequence, and the intracellular regions are positions 68 to 77, positions 134 to 150, positions 227 to 242 and positions 309 to 360 in the amino acid sequence (*J. Biol. Chem.*, 270, 19495 (1995)) At first, it was reported that the ligand of CCR4 is MIP-1α (macrophage inflammatory protein-1α), RANTES (regulated on activation normal T-cell expressed and secreted) or MCP-1 (monocyte chemotactic protein) (*Biochem. Biophys. Res. Commun.*, 218, 337 (1996), WO 96/23068). However, it has been found that TARC (thymus and activation-regulated chernokine) produced from stimulated human peripheral blood mononuclear cells (hereinafter referred to as "PBMC") and thymus cells (*J. Biol. Chem*, 271, 21514 (1996)) specifically binds to CCR4 (*J. Biol. Chem.*, 272, 15036 (1997)). It has been also reported that MDC (macrophage-derived chemokine) isolated from macrophage (*J. Exp. Med.*, 185, 1595 (1997)), also known as STCP-1 (stimulated T cell chemotactic protein-1) (*J. Biol. Chem.*, 272, 25229 (1997)), binds to CCR4 more strongly than TARC (*J. Biol. Chem.*, 273, 1764 (1998)).

It has been shown that CCR4 is expressed on CD4+Th cells which produce cytokine and/or chemokine (*J. Biol. Chem.*, 272, 15036 (1997)), and it has been reported that CCR4 is expressed selectively on Th2 cells among CD4+Th cells (*J. Exp. Med.* 187, 129 (1998), *J. Immunol.*, 161, 5111 (1998)). In addition, CCR4+ cells have been found in effector/memory T cells (CD4+/CD45RO+), and when CCR4+ cells were stimulated, IL-4 and IL-5 were produced but IFN-γ was not produced (*Int. Immunol.*, 11, 81 (1999)). Also, it has been reported that CCR4+ cells belong to a CLA (cutaneous lymphocyte antigen)-positive and α4β8 integrin-negative group among memory T cells, and CCR4 is expressed on memory T cells related not to gut immunity but to systemic immunity of the skin and the like (*Nature*, 400, 776 (1999)) These results strongly suggest that when inflammation is induced, the memory T cells are activated to express CCR4 and ate migrated into the inflammatory site by MDC and TARC of ligands of CCR4, and accelerate activation of other inflammatory cells.

It has been recently found that CCR4 is also expressed in natural killer cells (*Journal of Immunology*, 164, 4048-4054 (200), *Blood*, 97, 367-375 (2001)) and platelets (*Thrombosis Research*, 101, 279-289 (2001), *Blood*, 96, 4046-4054 (2000), *Blood*, 97, 937-945 (2001)) in human.

It is known that an antagonist of TARC or MDC as a ligand of CCR4, namely a CCR4 antagonist, inhibits platelet aggregation (WO 99/15666). It is known that such an agent modulating the function of CCR4 also affects on platelet functions.

Expression of CCR4 is found in platelets. For example, Adrian et al. (*Blood*, 97, 937-945 (2001)) and Abi-Younes et al. (*Thrombosis Research*, 101, 279-289 (2001), WO 00/42074, WO 00/41724) have detected expression of CCR4 in human platelets using anti-CCR4 antibodies. An antibody having reactivity with CCR4 but not capable of binding to human platelets has not been known to date.

Also, it is known that when an autoantibody capable of binding to platelets is produced, autoimrnune thrombopenia is induced (*Blood*, 70, 428-431 (1987), *Transfusion Science*, 19, 245-251 (1998)). Agents having influences on thrombocytopenia and platelet functions are not generally desirable as medicaments because they often cause severe side effects such as bleeding and thrombus formation. Particularly, since antibodies have long blood half-life, an antibody which affects on platelet functions is difficult to be developed as a medicament. For example, development of anti-CD40 ligand antibodies which had been developed as agents for treating autoimrnune diseases has been suspended because of the generation of side effects which are considered to be due to recognition of antigen expressed on activated platelets (*Nature Medicine*, 6, 114 (2000), *BioCentury*, A8 of 18 (2002.06.20)).

It is known that proteins are subjected to various modification reactions after translation. One of the modification reactions known is a sulfated reaction of tyrosine residues. It has been reported that many proteins are sulfated at tyrosine residues (*Chemistry and Biology*, 7, R57-R61 (2000)). The tyrosine residue which is sulfated has characteristic that many acidic amino acid residues are present in its vicinity, and a protein having a possibility of being sulfated and its region have been suggested (*Cell*, 96, 667-676 (1999)). Regarding CCR4, 4 tyrosine residues are present close to the N-terminal, but there are no reports showing that the tyrosine residues are sulfated.

As the current method for treating Th2-rediated imnune diseases, the followings have been developed: (1) antagonists for cytokines and chemokines such as a humanized anti-IL-5 antibody (SB-240563: Smith Kline Beecharm, Sch-55700 (CDP-835): Shehling Plough/Celitech), a humanized IL-4 antibody (U.S. Pat. No. 5,914,110), a soluble chemokine receptor (*J. Immunol.*, 160, 624 (1998)), etc.; (2) cytokine/chemokine production inhibitors such as an IL-5 production inhibitor (Japanese Published Unexamined Patent Application No. 53355/96), a retinoid antagonist (WO 99/24024), splatast tosilate (IPD-1151 T, manufactured by Taiho Pharmaceutical), etc.; (3) agents acting on eosinophil, mast cell and the like as final inflammatory cells, such as a humanized IL-5 receptor antibody (WO 97/10354), a CC chemokine receptor 3 (CCR3) antagonist (Japanese Published Unexamined Patent Application No. 147872/99), etc.; (4) inflammatory molecule inhibitors such as a humanized anti-IgE antibody (*Am. J. Respir. Crit. Care Med.*, 157, 1429 (1998)), etc.; and the like. But they inhibit only a part of the elaborate network among cytokine, chemokine and inflammatory cells. Th2-mediated immune diseases should not be cured by these agents Anti-CD4 antibodies have an activity to control T cells, and have effects on steroid-dependent severe asthma. However, since the CD4 molecule is broadly expressed in various immune cells, they lack in specificity and have a drawback of accompanying strong immunosuppressive effect (*Int. Arch. Aller. Immunol.*, 118, 133 (1999)).

Thus, in order to inhibit all of them, it is required to control specifically upstream of the problematic allergic reaction, namely Th2 cells.

The currently used common method for treating patients of severe Th2-mediated immune diseases is steroid administration, but side effects by steroids cannot be avoided. Also, there are drawbacks that the conditions of each patient return to the former state when the steroid administration is suspended, and that drug resistance is acquired when the steroid is administered for a long time.

To date, no human CDR-grafted antibody and the antibody fragment thereof which can detect CCR4-expressing cells and also has cytotoxicity against CCR4-expressing cells has been established. In addition, no therapeutic agent which can inhibit production of Th2 cytokine has been known so far.

Although it has been reported that CCR4 is also expressed on the cancer cells of leukemia patients (*Blood*, 96, 685 (2000)), no therapeutic agent which depletes leukemia cells has been known.

It is known in general that when an antibody derived from a non-human animal, e.g., a mouse antibody, is administered to human, it is recognized as an foreign substance and induces a human antibody against the mouse antibody (human anti-mouse antibody: hereinafter referred to as "HAMA") in the human body It is known that the HAMA reacts with the administered mouse antibody to cause side effects (*J. Clin. Oncol.*, 2, 881 (1984), *Blood*, 65, 1349 (1985), *J. Natl. Cancer Inst.*, 80, 932 (1988), *Proc. Natl. Acad. Sci. U.S.A.*, 82, 1242 (1985)), to accelerate disappearance of the administered mouse antibody from the body (*J. Nucl Med.*, 26, 1011 (1985), *Blood,* 65, 1349 (1985), *J. Natl. Cancer Inst.*, 80, 937 (1988)), and to reduce therapeutic effects of the mouse antibody (*J. Immunol.*, 135, 1530 (1985), *Cancer Res.*, 46, 6489 (1986)).

In order to solve these problems, attempts have been made to convert an antibody derived from a non-human animal into a human CDR-grafted antibody using genetic engineering technique.

The human CDR-grafted antibody is an antibody in which the amino acid sequence of CDR in the variable region (hereinafter referred to as "V region") derived from a non-human animal antibody is grafted into an appropriate position of a human antibody (*Nature*, 321, 522 (1986)). In comparison with antibodies derived from non-human animals such as mouse antibodies and the like, these human CDR-grafted antibodies have various advantages for clinical applications to human. For example, it has been reported that its immmunogenecity was reduced and its blood half-life became long compared with a mouse antibody using a monkey (*Cancer Res*., 56, 1118 (1996), *Immunol*., 85, 668 (1995)). Thus, it is expected that the human CDR-grafted antibodies have less side effects in human and their therapeutic effects continue for a longer time than antibodies derived from non-human animals.

Furthermore, since the human CDR-grafted antibody is prepared by using genetic engineering technique, molecules in various forms can be prepared For example, when γl subclass is used as a heavy chain (hereinafter referred to as "H chain") constant region (hereinafter referred to as "C region") (H chain C region is referred to as "CH") of a human antibody, a humanized antibody having a high effector function such as antibody-dependent cell-mediated cytotoxic (hereinafter referred to as "ADCC") activity can be prepared (*Cancer Res*., 56, 1118 (1996)) and a prolonged blood half-life compared with a mouse antibody is expected (*Immunol*., 85, 668 (1995)). Also, in treatment particularly for reducing the number of CCR4-expressing cells, higher cytotoxic activities such as complement-dependent cytotoxic activity (hereinafter referred to as "CDC activity") and ADCC activity via the Fc region (the region in and after the hinge region of an antibody heavy chain) of an antibody are important for the therapeutic effects. Therefore, these results clearly show that human CDR-grafted antibodies are preferred to antibodies derived from non-human animals such as mouse antibodies.

Furthermore, according to the recent advances in protein engineering and genetic engineering, antibody fragments having a smaller molecular weight such as Fab, Fab', $F(ab')_2$, a single chain antibody (hereinafter referred to as "scFv") (*Science*, 242, 423 (1988)), a dimerized V region fragment (hereinafter referred to as "Diabody") (*Nature Biotechnol*., 15, 629 (1997)), a disulfide stabilized V region fragment (hereinafter referred to as "dsFv") (*Molecular Immunol*, 32, 249 (1995)), a peptide containing CDR (*J. Biol Chem*., 271, 2966 (1996)) and the like, can be prepared as human CDR-grafted antibodies. The antibody fragments are excellent in transitional activity into target tissues compared to complete antibody molecules (*Cancer Res*., 52, 3402 (1992)).

It is considered that these fragments derived from human CDR-grafted antibodies and antibody fragments thereof are more desirable than those derived from antibodies derived from non-human animals such as mouse antibodies, when used in clinical applications to human.

As described above, diagnostic and therapeutic effects can be expected from human CDR-grafted antibodies and antibody fragments thereof when used alone, but attempts have been made to further improve the effects by using other molecules in combination. For example, cytokine can be used as one of such molecules. Cytokine is a general term for various soluble factors which control intercellular mutual functions in immune reactions. CDC activity and ADCC activity, for example, are known as the cytotoxic activities of antibodies, and ADCC activity is controlled by effector cells having Fc receptors on the cell surface such as monocytes, macrophages, NK cells and the like (*J. Immunol*., 138, 1992 (1987)). Since various cytokines activate these effector cells, they can be administered in combination with an antibody in order to improve ADCC activity of the antibody and the like.

SUMMARY OF THE INVENTION

An object of the present invention is to provide a novel human CDR-grafted antibody which specifically reacts with an extracellular region of CCR4 or the antibody fragment thereof.

The present invention relates to the following (1) to (59).

(1) A human CDR-grafted antibody which specifically reacts with an extracellular region of human CC chernokine receptor 4 (CCR4) but does not react with a human platelet, or the antibody fragment thereof.

(2) A human CDR-grafted antibody which specifically reacts with an extracellular region of human CC chemokine receptor 4 (CCR4) and has a cytotoxic activity against a CCP4-expressing cell, or the antibody fragment thereof.

(3) The human CDR-grafted antibody or the antibody fragment thereof according to (1), which has a cytotoxic activity against a CCR4-expressing cell.

(4) The human CDR-grafted antibody or the antibody fragment thereof according to any one of (1) to (3), wherein the extracellular region is an extracellular region selected from the group consisting of position 1 to 39, 98 to 112, 176 to 206 and 271 to 284 in the amino acid sequence represented by SEQ ID NO:48.

(5) The human CDR-grafted antibody or the antibody fragment thereof according to any one of (1) to (4), wherein the extracellular region is an epitope present in positions 2 to 29 in the amino acid sequence represented by SEQ ID NO:48.

(6) The human CDR-grafted antibody or the antibody fragment thereof according to any one of (1) to (5), wherein the extcellular region is an epitope present in positions 13 to 29 in the amino acid sequence represented by SEQ ID NO:48.

(7) The human CDR-grafted antibody or the antibody fragment thereof according to any one of (1) to (6), wherein the extracellular region is an epitope present in positions 13 to 25 in the amino acid sequence represented by SEQ ID NO:48.

(8) The human CDR-grafted antibody or the antibody fragment thereof according to any one of (1) to (7), which specifically reacts with a CCR4-expressing cell.

(9) The human CDR-grafled antibody or the antibody fragment thereof according to any one of (1) to (8), which has a higher cytotoxic activity against a CCR4-expressing cell than a monoclonal antibody produced by a non-human animal hybridorna.

(10) The human CDR-grafted antibody or the antibody fragment thereof according to any one of (2) to (9), wherein the cytotoxic activity is an antibody-dependent cell-mediated cytotoxic (ADCC) activity.

(11) The human CDR-grafted antibody or the antibody fragment thereof according to (10), wherein the ADCC activity is an activity of inducing apoptosis of a CCR4-expressing cell.

(12) The human CDR-grafted antibody or the antibody fragment thereof according to any one of (1) to (11), which has an activity of depleting a CCR4-expressing cell.

(13) The human CDR-grafted antibody or the antibody fragment thereof according to any one of (8) to (12), wherein the CCR4-expressing cell is a Th2 cell.

(14) The human CDR-grafted antibody or the antibody fragment thereof according to any one of (1) to (13), which has an activity of inhibiting cytokine-production of a Th2 cell.

(15) The human CDR-graed antibody or the antibody fragment thereof according to (14), wherein the cytokine is 1IL-4, IL-5 or IL-13.

(16) The human CDR-grafted antibody or the antibody fragment thereof according to any one of (1) to (15), which belongs to a human IgG antibody.

(17) The human CDR-grafted antibody or the antibody fragment thereof according to any one of (1) to (16), which comprises complementarity determining regions (CDRs) of a heavy chain (H chain) variable region (V region) and a light chain (L chain) V region of a monoclonal antibody against CCR4.

(18) The human CDR-grafted antibody or the antibody fragment thereof according to any one of (1) to (17), which comprises complementarity determining regions (CDR) of a heavy chain (H chain) variable region (V region) and a light chain (L chain) V region of a monoclonal antibody against CCR4, and framework regions (FRs) H chain V region and L chain V region of a human antibody.

(19) The human CDR-grafted antibody or the antibody fragment thereof according to any one of (1) to (18), which comprises complementarity determining regions (CDRs) of a heavy chain (H chain) variable region (V region) and light chain (L chain) V region of a monoclonal antibody against CCR4, framework regions (FRs) of H chain V region and L chain V region of a human antibody, and H chain constant region (C region) and L chain C region of a human antibody.

(20) The human CDR-grafted antibody or the antibody fragment thereof according to any one of (1) to (19), which comprises complementarity determining region (CDR) 1, CDR2 and CDR3 of an antibody heavy chain (H chain) variable region (V region) having the amino acid sequences represented by SEQ ID NOs:1, 2 and 3, respectively.

(21) The human CDR-grafted antibody or the antibody fragment thereof according to any one of (1) to (20), which comprises complementarity determining region (CDR) 1, CDR2 and CDR3 of an antibody light chain (L chain) variable region (V region) having the amino acid sequences represented by SEQ ID NOs:5, 6 and 7, respectively.

(22) The human CDR-grafted antibody or the antibody fragment thereof according to any one of (1) to (21), which comprises complementarity determining region (CDR) 1, CDR2 and CDR3 of an antibody heavy chain (H chain) variable region (V region) having the amino acid sequences represented by SEQ ID NOs:1, 2 and 3, respectively, and complementarity determining region (CDR) 1, CDR2 and CDR3 of an antibody light chain (L chain) V region having the amino acid sequences represented by SEQ ID NOs:5, 6 and 7, respectively.

(23) The human CDR-grafted antibody or the antibody fragment thereof according to any one of (1) to (22), which comprises an antibody heavy chain (H chain) variable region (V region) comprising an amino acid sequence in which at least one amino acid residue selected from Ala at position 40, Gly at position 42, Lys at position 43, Gly at position 44, Lys at position 76 and Ala at position 97 in the amino acid sequence represented by SEQ ID NO:4 is substituted with an other amino acid

(24) The human CDR-grafted antibody or the antibody fragment thereof according to any one of (1) to (22), which comprises an antibody heavy chain (H chain) variable region (V region) comprises an amino acid sequence in which at least one amino acid residue selected from Thr at position 28 and Ala at position 97 in the amino acid sequence represented by SEQ ID NO:38 is substituted with an other amino acid.

(25) The human CDR-grafted antibody or the antibody fragment thereof according to any one of (1) to (24), which comprises an antibody light chain (L chain) variable region (V region) comprising an amino acid sequence in which at least one amino acid residue selected from Ile at position 2, Val at position 3, Gin at position 50 and Val at position 88 in the amino acid sequence represented by SEQ ID NO:8 is substituted with an other amino acid.

(26) The human CDR-grafted antibody or the antibody fragment thereof according to any one of (1) to (23) and (25), which comprises an antibody heavy chain (H chain) variable region (V region) comprising an amino acid sequence in which at least one amino acid residue selected from Ala at position 40, Gly at position 42, Lys at position 43, Gly at position 44, Lys at position 76 and Ala at position 97 in the amino acid sequence represented by SEQ ID NO:4 is substituted with an other amino acid residue; and an antibody light chain (L chain) V region comprising an amino acid sequence in which at least one amino acid residue selected from Ile at position 2, Val at position 3, Gln at position 50 and Val at position 88 in the amino acid sequence represented by SEQ ID NO:8 is substituted with an other amino acid residue.

(27) The human CDR-grafted antibody or the antibody fragment thereof according to any one of (1) to (22), (24) and (25), which comprises an antibody heavy chain (H chain) variable region (V region) comprising an amino acid sequence in which at least one amino acid residue selected from Thr at position 28 and Ala at position 97 in the amino acid sequence represented by SEQ ID NO:38 is substituted with an other amino acid residue; and an antibody light chain (L chain) V region comprising an amino acid sequence in which at least one amino acid residue selected from Ile at position 2, Val at position 3, Gln at position 50 and Val at position 88 in the amino acid sequence represented by SEQ ID NO:8 is substituted with an other amino acid residue.

(28) The human CDR-grafted antibody or the antibody fragment thereof according to any one of (1) to (22) and (25), which comprises an antibody heavy chain (H chain) variable region (V region) comprising the amino acid sequence represented by SEQ ID NO:4, 9, 10, 11, 38, 39, 40 or 41.

(29) The human CDR-grafted antibody or the antibody fragment thereof according to any one of (1) to (24) and (28), which comprises an antibody light chain (L chain) variable region (V region) comprising the amino acid sequence represented by SEQ ID NO:8, 12, 13 or 14.

(30) The human CDR-grafted antibody or the antibody fragment thereof according to any one of (1) to (22), which comprises an antibody heavy chain (H chain) variable region (V region) comprising the amino acid sequence represented by SEQ ID NO:4, 9, 10, 11, 38, 39, 40 or 41; and an antibody light chain (L chain) V region comprising the amino acid sequence represented by SEQ ID NO:8, 12, 13 or 14.

(31) The human CDR-grafted antibody or the antibody fragment thereof according to any one of (1) to (22), which comprises an antibody heavy chain (H chain) variable region (V region) comprising the amino acid sequence represented by SEQ ID NO:9 or 10; and an antibody light chain (L chain) V region comprising the amino acid sequence represented by SEQ ID NO:14.

(32) The antibody fragment according to any one of (1) to (31), wherein the antibody fragment is an antibody fragment selected from Fab, Fab', $F(ab')_2$, a single chain antibody (scFv), a dimerized variable region (V region) fragment (Diabody), a disulfide-stabilized V region fragment (dsFv) and a peptide comprising a complementarity determining region (CDR).

(33) A human CDR-grafted antibody, which is produced by a transformant KM8759 (FERM BP-8129) or KM8760 (FERM BP-8130), or the antibody fragment thereof.

(34) A transformant which produces the human CDR-grafted antibody or the antibody fragment thereof according to any one of (1) to (33)

(35) The transformant according to (34), wherein the transformant is KM8759 (FERM BP-8129) or KM8760 (FERM BP-8130).

(36) A process for producing a transformant capable of producing the human CDR-grafted antibody or the antibody fragment thereof according to any one of (1) to (33), which comprises culturing the transformant according to (34) or (35) in a medium to form and accumulate the human CDR-grafted antibody or the antibody fragment thereof in the culture; and recovering the antibody or the antibody fragment from the culture.

(37) A human CDR-grafted antibody or the antibody fragment thereof in which the human CDR-grafted antibody or the antibody fragment thereof according to any one of (1) to (33) is chemically or genetically conjugated with a radioisotope, a protein or an agent.

(38) A DNA which encodes the human CDR-grafted antibody or the antibody fragment thereof according to any one of (1) to (33).

(39) A recombinant vector which comprises the DNA according to (38).

(40) A transformant which is obtainable by introducing the recombinant vector according to (39) into a host cell.

(41) A medicament which comprises at least one selected from the human CDR-grafted antibody and the antibody fragment thereof according to any one of (1) to (33) and (37) as an active ingredient.

(42) A therapeutic agent for treating CCR4-related diseases, which comprises at least one selected from the human CDR-grafted antibody and the antibody fragment thereof according to any one of (1) to (33) and (37) as an active ingredient.

(43) The therapeutic agent according to (42), wherein the CCR4-related disease is a cancer or inflammatory diseases.

(44) The therapeutic agent according to (43), wherein the cancer is a blood cancer.

(45) The therapeutic agent according to (44), wherein the blood cancer is leukemia or lymphomatosis.

(46) The therapeutic agent according to (43), wherein the inflammatory disease is acute or chronic airway oversensitivity or bronchial asthma, atopic skin disease, allergic rhinitis or pollinosis.

(47) A diagnostic agent for CCR4-related diseases, which comprises at least one selected from the human CDR-grafted antibody and the antibody fragment thereof according to any one of (1) to (33) and (37) as an active ingredient.

(48) The diagnostic agent according to (47), wherein the CCR4-related disease is a cancer or an inflammatory disease.

(49) The diagnostic agent according to (48), wherein the cancer is a blood cancer.

(50) The diagnostic agent according to (48), wherein the blood cancer is leukemia or lymphomatosis.

(51) The diagnostic agent according to (48), wherein the inflammatory disease is chronic airway oversensitivity asthma, bronchial asthma, atopic skin disease, allergic rhinitis or pollinosis.

(52) A therapeutic agent for treating Th2-mediated immune diseases, which comprises at least one selected from the human CDR-grafted antibody and the antibody fragment thereof according to any one of (1) to (33) and (37) as an active ingredient.

(53) The therapeutic agent according to (52), wherein the Th2-mediated immune disease is chronic airway oversensitivity asthma, bronchial asthma, atopic skin disease, allergic rhinitis or pollinosis.

(54) A diagnostic agent for Th2-mediated immune diseases, which comprises at least one selected from the human CDR-grafted antibody and the antibody fragment thereof according to any one of (1) to (33) and (37) as an active ingredient.

(55) The diagnostic agent according to (54), wherein the Th2-mediated immune disease is chronic airway oversensitivity asthma, bronchial asthma, atopic skin disease, allergic rhinitis or pollinosis.

(56) A method for immunologically detecting CCR4, which uses the human CDR-grafted antibody and the antibody fragment thereof according to any one of (1) to (33) and (37).

(57) A method for immunologically detecting a cell which expressed CCR4 on the cell surface, which comprises using the human CDR-grafted antibody or the antibody fragment thereof according to any one of (1) to (33) and (37).

(58) A method for reducing or depleting a cell which expressed CCR4 on the cell surface, which comprises using the human CDR-grafted antibody or the antibody fragment thereof according to any one of (1) to (33) and (37).

(59) A method for inhibiting cytokine-production of a Th2 cell, which comprises using the human CDR-grafted antibody or the antibody fragment thereof according to any one of (1) to (33) and (37).

DETAILED DESCRIPTION OF THE INVENTION

Figure 1:
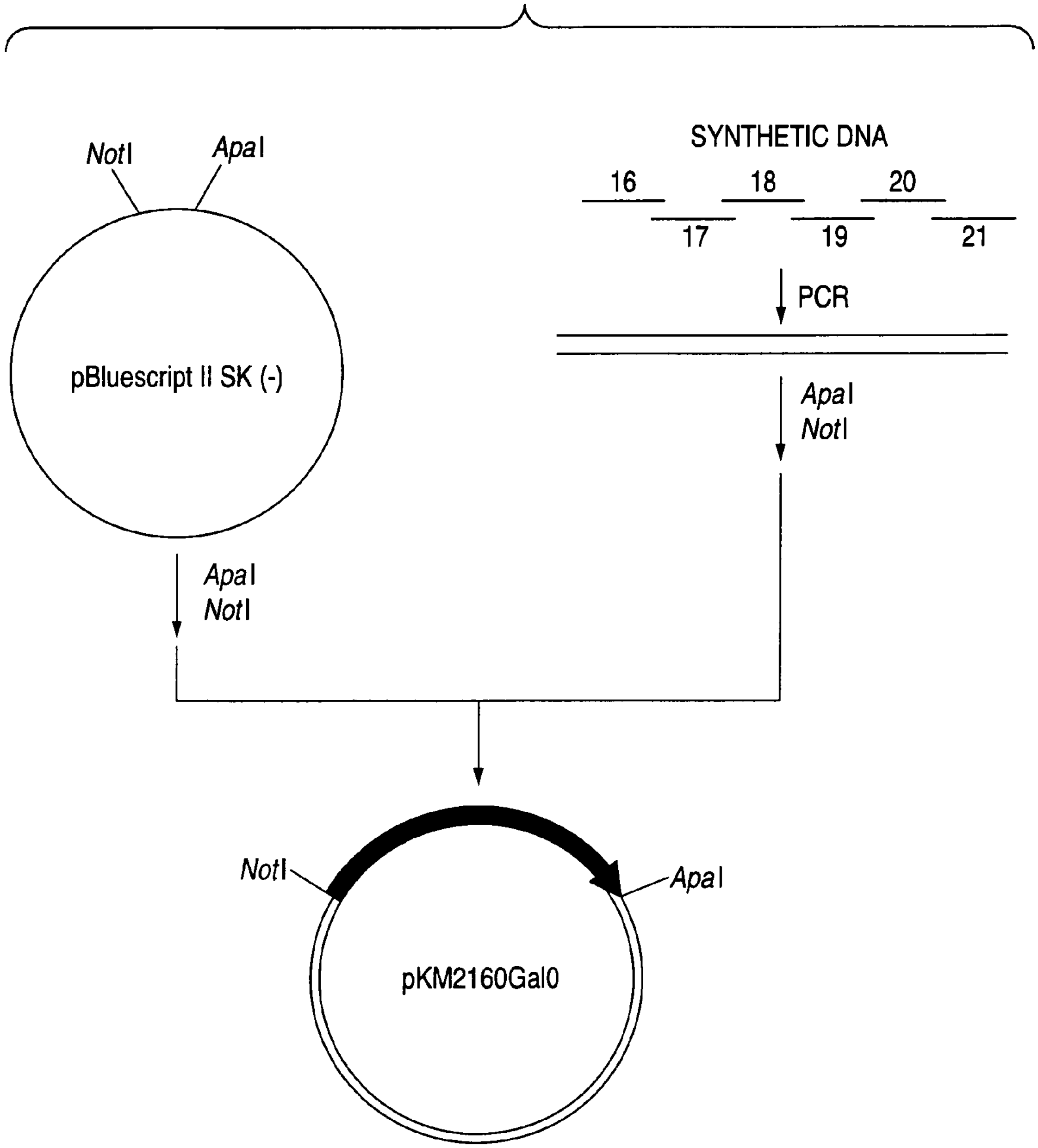
FIG. 1 shows construction steps of a plasmid pKM2160Gal0.

In the present invention, the CCR4-related diseases include cancers, inflammatory diseases and the like.

In the present invention, the cancers include blood cancers, particularly leukemia, lymphomatosis and the like.

In the present invention, the inflammatory diseases include acute or chronic airway oversensitivity or bronchial asthma; atopic skin diseases such as atopic dermatitis; allergic rhinitis; pollinosis; and the like.

In the present invention, the Th2-mediated immune diseases can be any immune diseases to which Th2 cell is related, and include acute or chronic airway oversensitivity or bronchial asthma; atopic skin diseases such as atopic dermatitis; allergic rhinitis; pollinosis; interstitial pneumonia, pulmonary fibrosis; autoimmnune diseases such as systemic lupus erythematosus; and the like.

The human CDR-grafted antibody which specifically reacts with CCR4 (anti-CCR4 CDR-grafted antibody) and an antibody fragment thereof of the present invention (hereinafter, both will be generally referred to as the antibody of the present invention in some cases) are not limited, so long as it is a human CDR-grafted antibody which specifically reacts with the extracellular region of human CCR4 but does not react with a human platelet or an antibody fragment thereof The term "does not react with a human platelet" means that the antibody shows substantially no binding activity to a human platelet. Specifically, it means that the binding activity is not shown when measured by a flow cytometer.

Also, the antibody of the present invention is an antibody which specifically reacts with the extracellular region of human CCR4 and has a cytotoxic activity for CCR4-expressing cells.

The cytotoxic activity includes CDC activity and ADCC activity.

Also, the antibody of the present invention includes antibodies which specifically react with preferably a region comprising positions 1 to 39, 98 to 112, 176 to 206 or 271 to 284 in the amino acid sequence represented by SEQ ID NO:48, more preferably a region comprising positions 2 to 29 in the amino acid sequence represented by SEQ ID NO:48 (SEQ ID NO:36), still more preferably a region comprising positions 12 to 29 in the amino acid sequence represented by SEQ ID NO:48 (SEQ ID NO:37), and most preferably a region comprising positions 12 to 25 in the amino acid sequence represented by SEQ ID NO:48.

The human CDR-grafted antibody represents an antibody in which amino acid sequences of CDR of VH and VL in an antibody derived from a non-human animal are grafted to appropriate positions of VH and VL of a human antibody.

The human CDR-grafted antibody of the present invention can be produced by constructing cDNAs encoding V regions in which amino acid sequences of CDR of VH and VL in an antibody derived from a non-human animal, which specifically reacts with CCR4, are grafted to FR of VIH and VL in a human antibody, inserting them respectively into an expression vector for animal cell having DNA encoding CH and H chain C region (hereinafter referred to as "CL") of a human antibody to construct a human CDR-grafted antibody expression vector, and then introducing it into an animal cell to express the human CDR-grafted antibody.

As the method for selecting FR amino acid sequences of VH and VL of a human antibody, any method can be used, so long as they are derived from human antibodies. Examples include FR amino acid sequences of VH and VL in human antibodies registered in data bases such as Protein Data Bank and the like, or amino acid sequences common in each subgroup of FR of VH and VL in human antibodies (*Sequences of Proteins of lmmunological Interest*, US Dep. Health and Human Services, 1991).

Any CH in the antibody of the present invention can be used, so long as it belongs to human immunoglobulin (hereinafter referred to as "hIg"). Preferably, an hIgG class, and any one of γ1, γ2, γ3 and γ4 subclasses belonging to the hIgG class can be used. Also, any CL in the human CDR-grafted antibody can be used, so long as it belongs to the hIg, and those of κ class or λ class can be used.

The antibody of the present invention includes human CDR-grafted antibodies or the antibody fragments thereof which comprise antibody HV CDR1, CDR2 and CDR3 comprising the amino acid sequences represented by SEQ ID NOs:1, 2 and 3, respectively, and/or VL CDR1, CDR2 and CDR3 comprising the amino acid sequences represented by SEQ ID NOs:5, 6 and 7, respectively.

Preferred examples include human CDR-grafted antibodies in which VH in the antibody comprises the amino acid sequence represented by SEQ ID NO:4 or 38 and/or VL comprises the amino acid sequence represented by SEQ ID NO:8.

More preferable examples include:

a human CDR-grafted antibody which comprises VH of the antibody comprising an amino acid sequence in which at least one amino acid residue selected from Ala at position 40, Gly at position 42, Lys at position 43, Gly at position 44, Lys at position 76 and Ala at position 97 in the amino acid sequence represented by SEQ ID NO:4 is substituted with an other amino acid residue, a human CDR-grafted antibody which comprises VH in the antibody comprising an amino acid sequence in which at least one amino acid residue selected from Thr at position 28 and Ala at position 97 in the amino acid sequence represented by SEQ ID NO:38 is substituted with an other amino acid residue, a human CDR-grafted antibody which comprises VL in the antibody comprising an amino acid sequence in which at least one amino acid residue selected from Ile at position 2, Val at position 3, Gln at position 50 and Val at position 88 in the amino acid sequence represented by SEQ ID NO:8 is substituted with an amino acid residue, a human CDR-grafted antibody which comprises VH in the antibody comprising an amino acid sequence in which at least one amino acid residue selected from Ala at position 40, Gly at position 42, Lys at position 43, Gly at position 44, Lys at position 76 and Ala at position 97 in the amino acid sequence represented by SEQ ID NO:4 is substituted with an other amino acid residue; and VL in the antibody comprising an amino acid sequence in which at least one amino acid residue selected from Ile at position 2, Val at position 3, Gln at position 50 and Val at position 88 in the amino acid sequence represented by SEQ ID NO:8 is substituted with an other amino acid residue, a human CDR-grafted antibody which comprises VH in the antibody comprising an amino acid sequence in which at least one amino acid residue selected from Thr at position 28 and Ala at position 97 in the amino acid sequence represented by SEQ ID NO:38 is substituted with an other amino acid residue; and VL in the antibody VL comprising an amino acid sequence in which at least one amino acid residue selected from Ile at position 2, Val at position 3, Gln at position 50 and Val at position 88 in the amino acid sequence represented by SEQ ID NO:8 is substituted with an other amino acid residue, and the like.

The present invention includes antibodies which comprise the amino acid sequence in which one or more amino acid is deleted, substituted, inserted or added and specifically react with CCR4 as described above, and the antibody fragments thereof.

In the present invention, one or more amino acid deletion, substitution, insertion or addition in the amino acid sequence means that one or more amino acids are deleted, substituted, inserted and/or added to at one or plural positions in the amino acid sequence. The deletion, substitution, insertion and/or addition can be caused in the same amino acid sequence simultaneously, Also, the amino acid residue substituted, inserted or added can be natural or non-natural. The natural amino acid residue includes L-alanine, L-asparagine, L-aspartic acid, L-glutamine, L-glutarnic acid, glycine, L-histidine, L-isoleucine, L-leucine, L-lysine, L-methionine, L-phenylalanine, L-proline, L-serine, L-threonine, L-tryptophan, L-tyrosine, L-valine, L-cysteine and the like.

Thereinafter, preferred examples of amino acid residues which are substituted with each other are shown. The amino acid residues in the same group can be substituted with each other.

Group A:

leucine, isoleucine, norleucine, valine, norvaline, alanine, 2-aminobutanoic acid, methionine, O-methylserine, t-butylglycine, t-butylalanine, cyclohexylalanine;

Group B:

aspartic acid, glutamic acid, isoaspartic acid, isoglutamic acid, 2-aminoadipic acid, 2-aminosuberic acid;

Group C:

asparagine, glutamine;

Group D:

lysine, arginine, omithine, 2,4-diaminobutanoic acid, 2,3-diaininopropionic acid;

Group E:

proline, 3-hydroxyproline, 4-hydroxyproline;

Group F;

serine, threonine, homoserine;

Group G:

phenylalanine, tyrosine

The antibody fragment of the present invention includes Fab, Fab', $F(ab')_2$, scFv, Diabody, dsFv, a peptide comprising CDR, and the like.

An Fab is an antibody fragment having a molecular weight of about 50,000 and antigen binding activity, in which about a half of the N-terminal side of H chain and the entire L chain, among fragments obtained by treating IgG with a protease, papain (cut at an amino acid residue at position 224 of the H chain), are bound together through a disulfide bond.

The Fab of the present invention can be obtained by treating a human CDR-grafted antibody of the present invention which specifically reacts with CCR4, with a protease, papain. Also, the Fab can be produced by inserting DNA encoding Fab of the antibody into an expression vector for prokaryote or an expression vector for eukaryote, and introducing the vector into a prokaryote or eukaryote to express the Fab.

An $F(ab')_2$ is an antibody fragment having a molecular weight of about 100,000 and antigen binding activity, which is slightly larger than the Fab bound via a disulfide bond of the hinge region, among fragments obtained by treating IgG with a protease, pepsin.

The F(ab')2 of the present invention can be obtained by treating a human CDR-grafted antibody which specifically reacts with CCR4, with a protease, pepsin. Also, the F(ab') can be produced by binding Fab' described below via a thioether bond or a disulfide bond. An Fab' is an antibody fragment having a molecular weight of about 50,000 and antigen binding activity, which is obtained by cutting a disulfide bond of the hinge region of the $F(ab')_2$.

The Fab' of the present invention can be obtained by treating the $F(ab')_2$ which specifically reacts with CCR4, with a reducing agent, dithiothreitol. Also, the Fab' of the present invention can be produced by inserting DNA encoding an Fab' of a human CDR-grafted antibody of the present invention which specifically reacts with CCR4 into an expression vector for prokaryote or an expression vector for eukaryote, and introducing the vector into a prokaryote or eukaryote to express the Fab'.

An scFv is a VH-P-VL or VL-P-VH polypeptide in which one chain VH and one chain VL are linked using an appropriate peptide linker (P) of 12 or more residues and which has an antigen-binding activity.

The scFv of the present invention can be produced by obtaining cDNAs encoding VH and VL of a human CDR-grafted antibody which specifically reacts with CCR4 of the present invention, constructing DNA encoding scFv, inserting the DNA into an expression vector for prokaryote or an expression vector for eukaryote, and then introducing the expression vector into a prokaryote or eukaryote to express the scFv.

A diabody is an antibody fragment in which scFv's having the same or different antigen binding specificity forms a dimer, and has an divalent antigen binding activity to the same antigen or two specific antigen binding activity to different antigens.

The diabody of the present invention, for example, a divalent diabody which specifically reacts with CCR4, can be produced by obtaining cDNAs encoding VH and VL of an antibody which specifically reacts with CCR4, constructing DNA encoding scFv having a polypeptide linker of 3 to 10 residues, inserting the DNA into an expression vector for prokaryote or an expression vector for eukaryote, and then introducing the expression vector into a prokaryote or eukaryote to express the diabody.

A dsFV is obtained by binding polypeptides in which one amino acid residue of each of VH and VL is substituted with a cysteine residue via a disulfide bond between the cysteine residues The amino acid residue which is substituted with a cysteine residue can be selected based on a three-dimensional structure estimation of the antibody in accordance with the method shown by Reiter et al. (*Protein Engineering*, 7, 697 (1994)).

The dsFv of the present invention can be produced by obtaining cDNAs encoding VH and VL of a human CDR-grafted antibody which specifically reacts with CCR4 of the present invention, constructing DNA encoding dsFv, inserting the DNA into an expression vector for prokaryote or an expression vector for eukaryote, and then introducing the expression vector into a prokaryote or eukaryote to express the dsFv.

A peptide comprising CDR is constituted by including at least one region of H chain and L chain CDRs. Plural CDRs can be bound directly or via an appropriate peptide linker.

The peptide comprising CDR of the present invention can be produced by obtaining CDNA encoding CDR of VH and VL of a human CDR-grafted antibody which specifically reacts with CCR4, constructing DNA encoding CDR, inserting the DNA into an expression vector for prokaryote or an expression vector for eukaryote, and then by introducing the expression vector into a prokaryote or eukaryote to express the peptide. Also, the peptide comprising CDR can also be produced by a chemical synthesis method such as an Fmoc method (fluorenylmethoxycarbonyl method), a tBoc method (t-butyloxycarbonyl method), or the like.

The antibody of the present invention includes antibody derivatives in which a radioisotope, a protein, an agent or the like is chemically or genetically conjugated to the antibody of the present invention.

The antibody derivatives of the present invention can be produced by chemically conjugating a radioisotope, a protein or a agent to the N-terminal side or C-terminal side of an H chain or an L chain of an antibody or antibody fragment which specifically reacts with CCR4, to an appropriate substituent group or side chain of the antibody or antibody fragment or to a sugar chain in the antibody or antibody fragment (*Antibody Engineering Handbook*, edited by Osamu Kanemitsu, published by Chijin Shokan (1994)).

Also, it can be genetically produced by linking a DNA encoding the antibody or the antibody fragment of the present invention which specifically reacts with CCR4 to other DNA encoding a protein to be bound, inserting the DNA into an expression vector, and introducing the expression vector into a host cell.

The radioisotope includes $^{131}I$, $^{125}I$ and the like, and it can be conjugated to the antibody by, e.g., a chloramine T method.

The agent is preferably a low molecular weight compound. Examples include anticancer agents such as alkylating agents (e.g., nitrogen mustard, cyclophosphamide), metabolic antagonists (e.g., 5-fluorouracil, methotrexate), antibiotics (e.g., daunomycin, bleomycin, mitomycin C, daunorubicin, doxorubicin), plant alkaloids (e.g., vincristine, vinblastine, vindesine), hormone drugs (e.g., tarnoxifen, dexamethasone), and the like (*Clinical Oncology*, edited by Japanese Society of Clinical Oncology, published by Cancer and Chemotherapy (1996)); anti-inflammatory agents such as steroid agents (e.g., hydrocortisone, prednisone), non-steroidal drugs (e.g., aspirin, indometacin), immunomodulators (e.g., aurothiomalate, penicillamine), immunosuppressing agents (e.g., cyclophosphamide, azathioprine) and antihistaminic agents (e.g., chlorpheniramine maleate, clemastine) (*Inflammation and Anti-inflammnatory Therapy*, Ishiyaku Shuppan (1982)); and the like. The method for conjugating daunomycin to an antibody includes a method in which daunomycin and an amino group of an antibody are conjugated via glutaraldehyde, a method in which an amino group of daunomycin and a carboxyl group of an antibody are conjugated via a water-soluble carbodimide, and the like.

The protein is preferably cytokine which activates immune cells. Examples include human interleukin 2 (hereinafter referred to as "hIL-2"), human granulocyte macrophage colony-stimulating factor (hereinafter referred to as "hGM-CSF"), human macrophage colony-stimulating factor (hereinafter referred to as "hM-CSF"), human interleukin 12 (hereinafter referred to as "hIL-12"), and the like. Also, in order to inhibit cancer cells directly, a toxin such as ricin, diphtheria toxin and the like, can be used. For example, a fusion antibody with a protein can be produced by linking a cDNA encoding an antibody or antibody fragment to other cDNA encoding the protein, constructing DNA encoding the fusion antibody, inserting the DNA into an expression vector for prokaryote or an expression vector for eukaryote, and then introducing it into a prokaryote or eukaryote to express the fusion antibody.

Methods for producing the human CDR-grafted antibody and the antibody fragment thereof which specifically react with CCR4, methods for evaluating the activity thereof and methods for using them are explained below.

1. Preparation of Human CDR-grafted Antibody (1) Construction of Humanized Antibody Expression Vector A humanized antibody expression vector is an expression vector for animal cell into which genes encoding CH and CL of a human antibody have been inserted, and is constructed by cloning each of CH and CL of a human antibody into an expression vector for animal cell.

The C region of a human antibody can be CH and CL of any human antibody. Examples include CH of γ subclass and CL of κ class of a human antibody, and the like Also, cDNA can be used As the expression vector for animal cell, any expression vector can be used, so long as a C region of a human antibody can be inserted and expressed. Examples include pAGE107 (*Cytotechnology*, 3, 133 (1990)), pAGE103 (*J. Biochem.*, 101, 1307 (1987)), pHSG274 (*Gene*, 27, 223 (1984)), pKCR (*Proc. Natl. Acad. Sci. USA*, 78, 1527 (1981)), pSGIβd2-4 (*Cytolechnology*, 4, 173 (1990)), pSE1UK1Sed1-3 (*Cytotechnol*, 13, 79 1993)) and the like. A promoter and enhancer used for an expression vector for animal cell includes an SV40 early promoter and enhancer (*J. Biochem.*, 101, 1307 (1987)), a Moloney mouse leukemia virus LTR promoter and enhancer (*Biochem. Biophys. Res. Comun.*, 149, 960 (1987)), an imnmunoglobulin H chain promoter (*Cell*, 41, 479 (1985)) and enhancer (*Cell*, 33, 717 (1983)), and the like.

The humanized antibody expression vector can be either of a type in which a gene encoding an antibody H chain and a gene encoding an antibody L chain exist on separate vectors or of a type in which both genes exist on the same vector (tandem type). In respect of easiness of construction of a humanized antibody expression vector, easiness of introduction into animal cells, and balance between the expression amounts of antibody H and L chains in animal cells, a tandem type of the humanized antibody expression vector is more preferred (*J. Immunol. Methods*, 167, 271 (1994)). The tandem type of the humanized antibody expression vector includes pKANTEX93 (WO 97/10354), pEE18 (HYBRIDOMA, 17, 559 (1998)) and the like.

The constructed humanized antibody expression vector can be used for expression of a human CDR-grafted antibody in animal cells.

(2) Construction of cDNA Encoding V Region of Human CDR-grafted Antibody cDNAs encoding VH and VL of a human CDR-grafted antibody can be obtained as follows. First, amino acid sequences of FRs in VH and VL of a human antibody to which amino acid sequences of CDRs in VH and VL of an antibody derived from a non-human animal antibody are grafted are selected. Any amino acid sequences of FRs in VH and VL of a human antibody can be used, so long as they are derived from human. Examples include amino acid sequences of FRs in VH and VL of human antibodies registered in database such as Protein Data Bank and the like, and amino acid sequences common to subgroups of FRs in VH and VL of human antibodies (*Sequences of Proteins of Immunological Interest*, US Dept. Health and Human Services (1991)), and the like. In order to produce a human CDR-grafted antibody having potent activity, amino acid sequences having high homology (at least 60% or more) with amino acid sequence of FRs in VH and VL of a target antibody derived from a non-human animal is preferably selected.

Then, amino acid sequences of CDRs in VH and VL of the antibody derived from a non-human animal are grafted to the selected amino acid sequences of FRs in VH and VL of a human antibody to design amino acid sequences of VH and VL of a human CDR-grafted antibody. The designed amino acid sequences are converted to DNA sequences by considering the frequency of codon usage found in nucleotide sequences of genes of antibodies (*Sequence of Proteins of Immunological Interest*, US Dept. Health and Human Services (1991)), and the DNA sequences encoding the amino acid sequences of VH and VL of a human CDR-grafted antibody are designed. Several synthetic DNAs having a length of about 100 to 200 nucleotides are synthesized, and PCR is carried out using them. In this case, it is preferred in each of VH and VL that 4 or 6 synthetic DNAs are designed in view of the reaction efficiency of PCR and the lengths of DNAs which can be synthesized. Furthermore, they can be easily cloned into the humanized antibody expression vector constructed in the item 1(1) by introducing the recognition sequence of an appropriate restriction enzyme to the 5' end of the synthetic DNAs present on the both ends. After the PCR, an amplified product is cloned into a plasmid such as pBluescript SK (−) (manufactured by Stratagene) or the like, and the nucleotide sequences arc determined to obtain a plasmid having DNA sequences encoding VH and VL of a designed human CDR-grafted antibody.

(3) Modification of Amino Acid Sequence of V Region of Human CDR-grafted Antibody It is known that when a human CDR-grafted antibody is produced by simply grafting only CDRs in VH and VL of an antibody derived from a non-human animal into FRs in VH and VL of a human antibody, its antigen-binding activity is lower than that of the original antibody derived from a non-human animal (*BIO/TECHNOLOGY*, 9, 266 (1991)). As the reason, it is considered that several amino acid residues in not only CDRs but also FRs directly or indirectly relate to antigen-binding activity in VH and VL of the original antibody derived from a non-human animal, and that they are changed to different amino acid residues of different FRs in VH and VL of a human antibody In order to solve the problem, in human CDR-grafted antibodies, among the amino acid sequences of FRs in VH and VL of a human antibody, an amino acid residue which directly relates to binding to an antigen, or an amino acid residue which indirectly relates to binding to an antigen by interacting with an amino acid residue in CDR or by maintaining the three-dimensional structure of an antibody is identified and modified to an amino acid residue which is found in the original non-human animal antibody to thereby increase the antigen binding activity which has been decreased (*BIO/TECHNOLOGY*, 9, 266 (1991)). In the production of a human CDR-grafted antibody, how to efficiently identify the amino acid residues relating to the antigen binding activity in FR is most important, so that the three-dimensional structure of an antibody is constructed and analyzed by X-ray crystallography (*J. Mol. Biol.*, 112, 535 (1977)), computer-modeling (*Protein Engineering*, 7, 1501 (1994)) or the like. Although the information of the three-dimensional structure of antibodies has been useful in the production of a human CDR-grafted antibody, no method for producing a human CDR-grafted antibody which can be applied to any antibodies has been established yet. Therefore, various attempts must be currently be necessary, for example, several modified antibodies of each antibody are produced and the relationship between each of the modified antibodies and its antibody binding activity is examined.

The modification of the selected amino acid sequence of FRs in VH and VL of a human antibody can be accomplished using various synthetic DNA for modification according to PCR. With regard to the amplified product obtained by the PCR, the nucleotide sequence is determined according to the method as described in the item 1(2) so that whether the objective modification has been carried out is confirmed.

(4) Construction of Human CDR-grafted Antibody Expression Vector

A human CDR-grafted antibody expression vector can be constructed by cloning cDNAs encoding VH and VL of the human CDR-grafted antibody constructed in the items 1(2) and 1(3) into upstream of the genes encoding VH and VL of the human antibody in the humanized antibody expression vector as described in the item 1(1) For example, when recognition sites for an appropriate restriction enzymes are introduced to the 5'-terminal of synthetic DNAs positioned at both ends among synthetic DNAs used in the construction of VH and VL of the human CDR-grafted antibody in the items 1(2) and (3), cloning can be carried out so that they are expressed in an appropriate form in upstream of genes encoding CH and CL of the human antibody in the humanized antibody expression vector as described in the item 1(1).

(5) Transient Expression of Human CDR-grafted Antibody

In order to efficiently evaluate the antigen binding activity of various human CDR-grafted antibodies produced, the human CDR-grafted antibodies can be expressed transiently using the human CDR-grafted antibody expression vector as described in the item 1(4) or the modified expression vector thereof. Any cell can be used as a host cell, so long as the host cell can express a human CDR-grafted antibody. Generally, COS-7 cell (ATCC CRL1651) is used in view of its high expression amount (*Methods in Nucleic Acids Res.*, CRC Press, p. 283 (1991)). The method for introducing the expression vector into COS-7 cell includes a DEAE-dextran method (*Methods in Nucleic Acids Res.*, CRC Press, p. 283 (1991)), a lipofection method (*Proc. Natl. Acad Sci. USA*, 84, 7413 (1987)), and the like.

After introduction of the expression vector, the expression amount and antigen binding activity of the human CDR-grafted antibody in the culture supernatant can be determined by the enzyme immunoassay (ELISA); *Antibodies: A Laboratory Manual*, Cold Spring Harbor Laboratory, Chapter 14 (1988), *Monoclonal Antibodies: Principles and Practice*, Academic Press Limited (1996)) and the like (6) Stable Expression of Human CDR-grafted Antibody A transformant which produces a human CDR-grafted antibody stably can be obtained by introducing into an appropriate host cell the human CDR-grafted antibody expression vector described in the item 1(4).

The method for introducing the expression vector into a host cell includes electroporation (*Cytotechnology*, 3, 133 (1990)) and the like.

Any cell can be used as the host cell into which the human CDR-grafted antibody expression vector is to be introduced, so long as it can express a human CDR-grafted antibody. Examples include mouse SP2/0-Ag14 cell (ATCC CRL1581), mouse P3X63-Ag8.653 cell (ATCC CRL1580), CHO cell in which a dihydrofolate reductase (defr) gene is detective (*Proc. Natl. Acad. Sci. U.S.A.*, 77, 4216 (1980)), rat YB2/3HL.P2.G11.16Ag.20 cell (YB2/0 cell; ATCC CRL1662) and the like.

After introduction of the expression vector, transfonnants which express a human CDR-grafted antibody stably are selected by culturing in a medium for animal cell culture containing an agent such as G418 sulfate (G418; manufactured by Sigma) or the like (*J. Immuol. Methods*, 167, 271 (1994)). The medium for animal cell culture includes PRMI1640 medium (manufactured by Nissul Pharmaceutical), GIT medium (manufactured by Nissui Pharmaceutical), EX-CELL302 medium (manufactured by JRH), IMDM medium (manufactured by GIBCO BRL), Hybridoma-SFM medium (manufactured by GIBCO BRL), media obtained by adding various additives such as FBS to these media, and the like. The human CDR-grafted antibody can be produced and accumulated in a culture medium by culturing the selected transformants in a medium. The expression amount and antigen binding activity of the humanized antibody in the culture supernatant can be measured by ELISA or the like. Also, in the transformant, the expression amount of the human CDR-grafted antibody can be increased by using dhfr amplification system or the like (*J. Immuol. Methods*, 167, 271 (1994)).

The human CDR-grafted antibody can be purified from the culture supernatant of the transformant by using a protein A column (*Antibodies: A Laboratory Manual*, Cold Spring Harbor Laboratory, Chapter 8 (1988), *Monoclonal Antibodies: Principles and Practice*, Academic Press Limited (1996)). Any other conventional methods for protein purification can be used. For example, the humanized antibody can be purified by a combination of gel filtration, ion-exchange chromatography, ultrafiltration and the like. The molecular weight of the H chain or the L chain of the purified humanized antibody or the antibody molecule as a whole is determined by polyacrylamide gel electrophoresis (SDS-PAGE; *Nature*, 227, 680 (1970)), Western blotting (*Antibodies: A Laboratory Manual*, Cold Spring Harbor Laboratory, Chapter 12 (1988), *Monoclonal Antibodies: Principles and Practice*, Academic Press Limited (1996)) and the like.

2. Preparation of Antibody Fragment

The antibody fragment can be prepared based on the humanized antibody described in the item 1 using genetic engineering or protein engineering. The antibody fragment includes Fab, $F(ab')_2$, Fab', sdFv, diabody, dsFv, a peptide comprising CDR, and the like.

(1) Preparation of Fab

Fab can be prepared by treating IgG with a proteolytic enzyme papain. After the papain treatment, when the original antibody is an IgG subclass having a protein A binding activity, uniform Fab can be recovered by separating it from lgG molecules and Fc fragments by passing through a protein A column (*Monoclonal Antibodies: Principles and practice*, third edition (1995)). When the original antibody is an antibody of IgG subclass having no protein A binding activity, Fab can be recovered by ion exchange chromatography in a fraction eluted at a low salt concentration (*Monoclonal Antibodies: Principles and Practice*, third edition (1995)). In addition, Fab can also be prepared by genetic engineering techniques using *Escherichia coli*. For example, an Fab expression vector can be prepared by cloning the DNA encoding the antibody V region described in the items 1(2) and 1(3) into a vector for Fab expression. As the vector for Fab expression, any vector can be used, so long as a DNA for Fab can be inserted and expressed Examples include pIT106 (*Science*, 240, 1041 (1988)) and the like. Fab can be formed and accumulated in an inclusion body or periplasmic space by introducing the Fab expression vector into an appropriate *Escherichia coli*. Active Fab can be obtained from the inclusion body by a refolding method generally used for protein, and when it is expressed in the periplasmic space, active Fab is leaked in the culture supernatant. Uniform Fab can be purified after the refolding or from the culture supernatant using an antibody-linked column (*Antibody Engineering A Practical Guide*, W. H. Freeman and Company (1992)).

(2) Preparation of $F(ab')_2$ $F(ab')_2$ can be prepared by treating IgG with a proteolytic enzyme papain. After the papain treatment, it can be recovered as uniform $F(ab')_2$ by a purification procedure similar to the case of Fab (*Monoclonal Antibodies: Principles and Practice*, third edition, Academic Press (1995)). In addition, it can also be prepared by the method described in the item 2(3) in which Fab' is treated with maleimide such as o-PDM, bismaleimide hexane or the like to form a thioether bond, or a method in which it is treated with DTNB to form an S—S bond (*Antibody Engineering, A Practical Approach*, IRL PRESS (1996)).

(3) Preparation of Fab'

Fab' can be prepared by genetic engineering techniques using *Escherichia coli*. For example, an Fab' expression vector can be constructed by cloning the DNA encoding the antibody V region described in the items 1(2) and (3) into a vector for Fab' expression. As the vector for Fab' expression, any vector can be used, so long as a DNA for Fab' can be inserted and expressed. Examples include pAK19 (*Bio/Technology*, 10, 163 (1992)) and the like. Fab' can be formed and accumulated in an inclusion body or periplasmic space by introducing the Fab' expression vector into an appropriate *Escherichia coli*. Active Fab' can be obtained from the inclusion body by a refolding method generally used for protein, and when it is expressed in the periplasmic space, it can be recovered into extracellular moiety by disrupting the cells with a treatment such as lysozyme partial digestion, osmotic pressure shock, sonication or the like. Uniform Fab' can be purified after the refolding or from the disrupted cell suspension using a protein G column or the like (*Antibody Engineering, A Practical Approach*, IRL PRESS (1996)).

(4) Preparation of ScFv scFv can be prepared using a phage or *Escherichia coli* by genetic engineering techniques. For example, a DNA encoding scFv is produced by ligating DNAs encoding the antibody VH and VL described in the items 1(2) and (3) via a DNA encoding a polypeptide linker comprising an amino acid sequence of 12 residues or more. An scfv expression vector can be constructed by cloning the resulting DNA into a vector for scFv expression. As the vector for scFv expression, any vector can be used, so long as a DNA for scFv can be inserted and expressed. Examples include pCANTAB5E (manufactured by Pharmacia), Phfa (*Hum. Antibody Hybridoma*, 5, 48 (1994)) and the like. The scFv expression vector was introduced into an appropriate *Escherichia coli* and infected with a helper phage to thereby obtain a phage which expresses scFv on the phage surface in a fused form with the phage surface protein. Also, scFv can be formed and accumulated in the inclusion body or periplasmic space of *Escherichia coli* into which scFv expression vector is introduced Active scFv can be obtained from the inclusion body by a refolding method generally used for protein, and when it is expressed in the periplasmic space, it can be recovered extracellularly by disrupting the cells with a treatment such as lysozyme partial digestion, osmotic pressure shock, sonication or the like. Uniform scFv can be purified after the refolding or from the disrupted cell suspension by cation exchange chromatography or the like (*Antibody Engineering, A Practical Approach*, IRL PRESS (1 996)).

(5) Preparation of Diabody

Diabody can be prepared by changing the size of the polypeptide linker for preparing scFv to about 3 to 10 residues. A divalent diabody can be prepared when VH and VL of one antibody species is used, and a diabody having two different specificity when VH and VL of two antibody species are used (*FEBS Letters*, 453 164 (1999), *Int. J. Cancer*, 77, 763 (1998)).

(6) Preparation of DsFv dsFv can be prepared using *Escherichia coli* by genetic engineering techniques. First, DNAs in which an encoded amino acid residue is replaced with a cysteine residue are produced by introducing mutation into appropriate positions of the DNAs encoding the antibody VH and VL described in the items 1(2) and 1(3). VH and VL expression vectors can be produced by cloning each of the resulting DNAs into a vector for dsFv expression. As the vector for dsFv expression, any vector can be used, so long as a DNA for dsFv can be inserted and expressed. Examples include pUL19 (*Protein Engineering*, 7, 697 (1994)) and the like. The VH and VL expression vectors are introduced into an appropriate *Escherichia coli* to thereby form and accumulate the VH and VL in the inclusion body or periplasmic space. The VH and VL are obtained from the inclusion body or periplasmic space and mixed, and active dsFv can be obtained by a refolding method generally used for protein. After the refolding, it can be flrther purified by ion exchange chromatography and gel filtration or the like (*Protein Engineering*, 7, 697 (1994)).

(7) Preparation of Peptide Comprising CDR

A peptide comprising CDR can be prepared by a chemical synthesis method such as Fmoc, tBoc or the like. Also, a DNA encoding a peptide comprising CDR is prepared, and the resulting DNA is cloned into an appropriate vector for expression to thereby prepare the peptide comprising CDR. As the vector for expression, any vector can be used, so long as a DNA encoding a peptide comprising CDR is inserted and expressed. Examples include pLEX (manufactured by Invitrogen), pAX4a+ (manufactured by Invitrogen) and the like. The expression vector is introduced into an appropriate *Escherichia coli* so that the peptide comprising CDR can be formed and accumulated in the inclusion body or periplasmic space. The peptide comprising CDR can be obtained from the inclusion body or periplasmic space, and it can be purified by ion exchange chromatography and gel filtration or the like (*Protein Engineering*, 7, 697 (1994)).

3. Evaluation of Activity and Property of the Antibody of the Present Invention (1) Evaluation of Binding Activity for Antigen A binding activity of the antibody of the present invention for an antigen can be measured by enzyme-linked immunosorbent assay (ELISA), fluorescent antibody technique (*Cancer Immunol. Immunother.*, 36, 373 (1993), surface plasmon resonance using such as BIAcore™ and the like Specifically, a synthetic peptide comprising a CCR4 partial sequence is produced and a conjugate is prepared by chemically linking it to a carrier protein such as bovine serum albumin or the like. A CCR4 binding activity of the antibody of the present invention can be measured by immobilizing the conjugate on an ELISA plate, allowing it to react with the antibody of the present invention, further allowing it to react with a labeled antibody or binding fragment such as a peroxidase- or biotin-labeled antibody or binding fragment, and then measuring a coloring dye using an absorption photometer (2) Reactivity for CCR4-expressing Cells In order to examine the reactivity for CCR4-expressing cells, it is preferable to use a method for efficiently detecting CCR4 expressed on the cell surface. The method includes flow cytometry using fluorescent antibody technique and the like. In addition, when reactivity with living body cells such as platelet and the like are examined, it is preferable to carry out the examination under conditions as close as possible to the living body. Because of these reasons, when reactivity of the anti-CCR4 antibody of the present invention is examined, it is most desirable to carry out the examination by flow cytometry using fluorescent antibody technique.

The antibody used in the fluorescent antibody technique may be either an antibody labeled with a fluorescent material such as FITC, biotin or the like, or an unlabeled antibody. Depending on the presence or absence of a label of the used antibody and its kind, fluorescence-labeled avidin, a fluorescence-labeled anti-human immunoglobulin antibody and the like are used. The reactivity can be evaluated by carrying out the reaction by adding a sufficient amount of an anti-CCR4 antibody (generally from 0.1 to 10 μg/ml as the final concentration) to a tested sample and by comparing its reactivity with those of a negative control antibody and a positive control antibody.

(3) Cytotoxic Activity

The cytotoxic activity for CCR4-expressing cells can be evaluated by measuring CDC activity, ADCC activity and the like (*Cancer Immunol. Immunother.,* 36, 373 (1993)) Changes in the amount of produced cytokine can be measured by ELISA method, fluorescent antibody technique and the like using an antibody for cytokine.

(4) Activity of Inhibiting Ligand Binding

An activity of inhibiting ligand binding of the anti-CCR4 antibody of the present invention can be examined by using a label of TARC or MDC as a ligand having a binding activity to CCR4 and a CCR4-expressing cell or a cell membrane fraction thereof. TARC or MDC can be labeled by any technique which can be detected, and examples include fluorescence labeling, enzyme labeling, radiation labeling and the like. Specific examples include the method by measuring the binding inhibition activity using a radiation label described in WO 00/42074.

Also, an activity of inhibiting ligand binding of the anti-CCR4 antibody of the present invention can be examined by using a cell response induced by binding of a ligand to CCR4 as an index. The cell response may be any type, so long as it is induced by contacting a ligand with a CCR4expressing cell, and examples include changes in intracellular calcium concentration, cell migration and the like Specific examples include the method measuring migration inhibition of a CCR4-expressing cell induced by a CCR4 ligand described in WO 00/42074.

(5) Examination of Recognition Sequence

An amino acid sequence recognizable by the antibody of the present invention can be determined by using a synthetic peptide designed based on the primary sequence of its corresponding antigen protein.

A primary sequence of the synthetic peptide is designed based on the primary sequence of the antigen protein. In order to prepare a protein in which the synthetic peptide is crosslinked with a carrier protein, a cysteine residue can be added to the carboxyl terminal or amino terminal of the synthetic peptide. The resulting protein can be used in the ELISA which will be described later. Also, if necessary, the N-terminal and C-terminal of the synthetic peptide can be acetylated and amidated, respectively.

A peptide can be synthesized by a general liquid phase or solid phase peptide synthesizing method, an any combined method thereof or a modified method thereof (*International Journal of Peptide Protein Research*, 35, 161-214 (1990), "Solid-Phase Peptide Synthesis", *Methods in Enzymology*, vol. 289, edited by Gregg B. Fields, Academic Press (1997), "Peptide Synthesis Protocols", *Methods in Molecular Biology*, vol. 35, edited by Michael W. Pennington and Ben M. Dunn, Humana Press (1994)).

In addition, an automatic peptide synthesizer can also be used. Synthesis of a peptide by a peptide synthesizer can be carried out by a commercially available peptide synthesizer such as the peptide synthesizer manufactured by Shimadzu Corp., the peptide synthesizer manufactured by Advanced ChemTech Inc, USA (hereinafter referred to as "ACT") or the like, using $N^{\alpha}$-Fmoc-amino acids, $N^{60}$ -Boc-amino acids or the like whose side chains are appropriately protected and in accordance with respective synthesis programs. The protected amino acids used as the material and carrier resins can be purchased from ABI Inc., Shirnadzu Corp., Kokusan Kagaku K.K., NovaBiochem, Watanabe Kagaku K.K., ACT, AnaSpec Inc., Peptide Research Institute and the like.

As the method for determining an amino acid sequence recognizable by the antibody of the present invention using the synthetic peptide, any technique can be used, so long as it is a method which can detect binding of the synthetic peptide to the antibody. For example, the amino acid sequence recognizable by the antibody can be determined by labeling the synthetic peptide with a fluorescent material, a radioactive material or the like and examining the binding activity of the resulting labeled peptide to the antibody. Also, it can be carried out by crosslinking the synthetic peptide with a protein such as bovine serum alburnin (BSA) or the like and evaluating the reactivity of the resulting protein with the antibody by ELISA or the like. In addition, an amino acid sequence recognizable by the antibody of the present invention can also be determined by using a substance already confirmed that the antibody links thereto, such as an antibody protein, and examining a synthetic peptide which inhibits linking of the antibody to the substance.

4. Method for Detecting and Quantifying CCR4 using Anti-CCR4-antibody

The present invention relates to a method for immunologically detecting and determining CCR4 or a cell expressing CCR4 on the surface thereof using the antibody of the present invention.

The methods for immunologically detecting and determining CCR4 or a cell expressing CCR4 on the surface thereof using the antibody of the present invention include an immunofluorescent method, an enzyme-linked immunosorbent assay (ELISA), a radioactive material labeled immunoassay (RIA), an immunohitsochemical staining method such as an immunocyte staining method, an immunotissue staining method, or the like (ABC method, CSA method, etc.), the above enzyme immunoassay, a sandwich ELISA (*Monoclonal Antibody Experiment Manual* (published by Kodansha Scientific, 1987), *Second Series Biochemical Experiment Course*, Vol. 5, *Immunobiochemistry Research Method*, published by Tokyo Kagaku Dojin (1986)).

The immunofluorescent method comprises reacting a separated cell, tissue, or the like with the antibody of the present invention, reacting the reactant with an anti-immunoglobulin antibody or binding fragment labeled with a fluorescence substance such as fluorescein isothiocyanate (FITC) or the like, and then measuring the fluorescence substance with a flow cytometer.

The enzyme-linked immunosorbent assay (ELISA) comprises reacting a separated cell or cell lysate thereof, tissue or tissue lysate thereof, cell culture supernatant, serum, preural fluid, ascites fluid, ocular fluid or the like with the antibody of the present invention, reacting the reactant with an anti-immunoglobulin antibody or binding fragment labeled with an enzyme such as peroxydase, biotin, or the like, and then measuring the resultant developed dye with an absorption photometer.

The radioactive material labeled immunoassay (RIA) comprises reacting a separated cell or cell lysate, tissue or tissue lysate, cell culture supernatant, serum, preural fluid, ascites fluid, ocular fluid or the like with the antibody of the present invention, further reacting the reactant with an anti-immnunoglobulin antibody or binding fragment labeled with radioisotope, and then measuring the radioactivity with a scintillation counter or the like.

The immunocyte staining and immunotissue staining methods comprise reacting a separated cell, tissue or the like with the antibody of the present invention, reacting the reactant with an anti-immunoglobulin antibody or binding fragment labeled with a fluorescence substance such as fluorescein isothiocyanate (FITC) or the like, or an enzyme such as peroxydase, biotin or the like, and then observing the cell, tissue or the like with a microscope.

The sandwich ELISA is a method which comprises adsorbing, on a plate, one of two antibodies having a different epitope among the antibodies of the present invention; labeling another antibody with a fluorescence substance such as FITC or the like, or an enzyme such as peroxydase, biotin or the like; reacting a separated cell or cell lysate, tissue or tissue lysate, cell culture supernatant, serum, preural fluid, ascites fluid, ocular fluid, or the like with the antibody-adsorbing plate; and then reacting it with the labeled antibody for carrying out a reaction according to the labeled substance.

5. Method for using Human CDR-grafted Antibody or Antibody Fragment Thereof

Since the antibody of the present invention specifically binds to CCR4 which is expressed on a cultured cell line and shows cytotoxic activity such as CDC activity, ADCC activity and the like, it will be useful in diagnosing and treating diseases relating to CCR4 such as Th2-mediated diseases and the like Also, since the proportion of amino acid sequences derived from human antibody is higher than that in antibodies of a non-human animal, it is expected that it shows strong cytotoxic activity in the human body, it does not show immunogenicity, and its effects continue for a long time.

In addition, the production of Th2 cytokines which are produced by cells such as IL-4, IL-5, IL-13 and the like, can be inhibited by administering the antibody of the present invention to cells or tissues of an experimental subject.

As the cell expressing CCR4 relating to the present invention, Th2 cell and the like are exemplified. The Th2 cell used in the present invention is preferably activated Th2 cell or memory Th2 cell. Examples include cells having CD45RA− or CD45RO+ and CD4+ properties.

The cytotoxic activities of the antibody of the present invention are generated, e.g., when the antibody of the present invention binds to CCR4-expressing cells such as a Th2 cell to thereby induce apoptosis in the cell. Also, the cell can be obstructed and depleted by inducing apoptosis.

Also, the method for diagnosing Th2-mediated immune diseases or cancers includes a method in which a human CCR4 positive cell existing in cells or tissues of an experimental subject is immunologically detected as described above.

Furthermore, the antibody of the present invention can be used as a diagnostic agent for CCR4-related diseases such as Th2-mediated immune diseases or cancers, or diseases in which the morbid states advance due to abnormal increase or decrease of Th2 cells.

Moreover, since the antibody of the present invention can reduce or deplete CCR4-expressing cells by its cytotoxic activity, it can provide a diagnostic method or therapeutic method for CCR4-related diseases such as Th2-mediated immune diseases or cancers, which uses the antibody of the present invention, and therapeutic and preventive agents for CCR4-related diseases such as Th2-mediated imnune diseases or cancers which comprises the antibody of the present invention as an active ingredient.

The Th2-mediated if immune diseases include, irrespective of mild or severe, inflammatory diseases such as acute or chronic airway hypersensitivity or bronchial asthma, atopic skin diseases including atopic dermatitis, allergic rhinitis, pollinosis, and the like; diseases caused by inflammation competent cells such as eosinophil, mast cell and the like which can be propagated or activated by cytokine and chemokine released from Th2 cells, biologically functional molecules such as IgE and the like which are produced by cytokine and chemokine released from Th2 cells, and the like; and immune diseases in which the morbid states advance due to abnormal changes in Th2 cells.

The antibody of the present invention can be administered alone, but it is generally preferred to provide it in the form of a pharmaceutical formulation produced by mixing it with at least one pharmaceutically acceptable carrier in accordance with a method well known in the technical field of pharmaceutics.

It is preferred to select a route of administration which is the most effective in carrying out the intended treatment such as oral administration or parenteral administration, e.g., intraoral administration, tracheal administration, rectal administration, subcutaneous injection, intramuscular injection, intravenous injection, and the like. Intravenous injection is preferred in an antibody or peptide formulation.

The dosage form includes sprays, capsules, tablets, granules, syrups, emulsions, suppositories, injections, ointments, tapes, and the like.

Formulations suitable for oral administration include emulsions, syrups, capsules, tablets, powders, granules, and the like.

Liquid preparations such as emulsions and syrups, can be produced using additives such as water; saccharides, e.g., sucrose, sorbitol, fructose; glycols, e.g., polyethylene glycol, propylene glycol; oils, e.g., sesame oil, olive oil, soybean oil; antiseptics, e.g., p-hydroxybenzoate; and flavors, e.g., strawberry flavor, peppermint.

Capsules, tablets, powders, granules and the like can be produced using additives such as fillers, e.g., lactose, glucose, sucrose, mannitol; disintegrating agents, e.g., starch, sodium alginate; lubricants, e.g., magnesium stearate; talc; binders, e.g., polyvinyl alcohol, hydroxypropylcellulose, gelatin; surfactants, e.g., fatty acid esters; and plasticizers, e.g., glycerine.

Formulations suitable for parenteral administration include injections, suppositories, sprays, and the like.

Injections can be prepared using a carrier such as a salt solution, glucose solution or a mixture thereof, or the like.

Suppositories can be prepared using a carrier such as cacao butter, hydrogenated fat, a carboxylic acid, or the like.

Also, sprays can be prepared from the antibody itself or using a carrier or the like which does not stimulate oral and airway mucous membranes of patients and can facilitate absorption of the antibody or antibody fragment thereof by dispersing it as minute particles.

The carrier includes lactose, glycerine, and the like. Depending on the properties of the antibody or peptide and the carrier to be used, aerosols, dry powders and the like can be produced. The additives exemplified in the oral preparations can also be added to the parenteral preparations.

The dose and frequency of administration vary depending on intended therapeutic effect, administration method, treating period, age, body weight and the like, but the dose is generally from 0.01 mg/kg to 20 mg/kg per day per adult.

As discussed above, according to the present invention, a recombinant antibody and an antibody fragment thereof, which binds specifically to human CCR4 and contains novel CDRs for CCR4, are provided. The antibody of the present invention is useful for the diagnosis or treatment of CCR4-related diseases. Specifically, it is useful for the immunological detection of a human Th2 cell by immunocyte staining and for the diagnosis or treatment of all Th2-mediated immune diseases including bronchial asthma and atopic skin diseases, diseases in which the morbid states advance due to abnormal balance of Th2 cells and cancers including blood cancers such as leukemia.

The present invention are described below based on Examples, but the present invention is not limited thereto.

EXAMPLE 1

Production of Human CDR-grafted Antibody for CCR4:

1. Designing of cDNA Encoding VH and VL of Human CDR-grafted Antibody for CCR4

(1) Designing of Amino Acid Sequence of VH of Human CDR-grafted Antibody for CCR4

First, an amino acid sequence of the VH of a human CDR-grafted antibody for CCR4 (anti-CCR4 CDR-grafted antibody) was designed as follows. An amino acid sequence of FR of VH of a human antibody was selected for grafting amino acid sequences of CDR1, 2 and 3 of VH represented by SEQ ID NOs:1, 2 and 3 using the anti-CCR4 mouse antibody KM2160 (*Int. Immunol*, 11, 81 (1999)) established in Reference Example 1. Human antibodies having high homology with KM2160 were retrieved from amino acid sequence data bases of existing proteins by BLASTP method (*Nucleic Acid Res*., 25, 3389 (1997)) using GCG Package (manufactured by Genetics Computer Group) as a sequence analyzing system. When the homology of the actual amino acid sequence was compared with the homology scores, SWISSPROT data base accession number P01781, Ig Heavy chain V-III region Gal (*Hoppe. Seylers. Z. Physiol Chem*., 354, 1505-1509 (1973); hereinafter referred to as "Gal ") was a human antibody showing the highest homology of 82.5%, so that the FR amino acid sequence of the antibody was selected However, positions where the amino acid residues cannot be determined uniquely (positions 28 and 30 from the N-terminal of a secretory antibody) and an amino acid residue which has low generation frequency in sequences of human antibodies (Thr as the final residue of V region) were found in the FR amino acid sequence of Gal on the data base. Accordingly, Ile and Ser as residues found in the mouse KM2160 were selected as positions 28 and 30, and Thr as the final residue of V region was substituted with Ser. Since the amino acid residues are found at high frequencies in sequences of any human antibodies (*Sequences of Proteins of Immunological Interest*, U.S. Dep. Health and Human Services, 1991), they do not deviate from human antibody sequences.

The VH amino acid sequence Gal0 of anti-CCR4 CDR-grafted antibody represented by SEQ ID NO:4 was designed by grafting amino acid sequences of CDR1, 2 and 3 of VH of the anti-CCR4 mouse antibody KM2160 represented by SEQ ID NOs:1, 2 and 3, respectively, to appropriate positions in the determined human antibody FR amino acid sequence. A nucleotide sequence encoding the amino acid sequence of SEQ ID NO:4 is represented by SEQ ID NO:49.

Also, an amino acid sequence of VH of the anti-CCR4 CDR-grafted antibody was designed based on the common sequences classified by Kabat et al.

Kabat et al. have classified the VH of various already known human antibodies into three subgroups (HSG I to III ) based on the homology of their amino acid sequences and reported common sequences in each subgroup (*Sequences of Proteins of Immunological Interest*, US Dep. Health and Human Services, 1991). There is a possibility that immunogenicity of the common sequences will be reduced in human. Accordingly, in order to prepare an anti-CCR4 CDR-grafted antibody having high activity, among FR amino acid sequences of the common sequences of three subgroups of the human antibody VH, an FR amino acid sequence having the highest homology with the FR amino acid sequence of VH of KM2160 was selected in the designing. Table 1 shows a result of the retrieval of homology between the FR amino acid sequences of the common sequences of each subgroup of the human antibody VH and the FR amino acid sequence of VH of KM2160. As shown in Table 1, the FR amino acid sequence of the VH region of KM2160 showed the highest homology with the subgroup III.

TABLE 1

| HSG I | HSG II | HSG III |
|---|---|---|
| 57.47% | 50.58% | 77.01% |

Based on the above results, the VH amino acid sequence HV0 of anti-CCR4 CDR-grafted antibody represented by SEQ ID NO:38 was designed by grafting amino acid sequence of CDR of VH of the anti-CCR4 mouse antibody KM2160 to an appropriate position of the amino acid sequence of FR of the common sequence of subgroup III of the human antibody VH. A nucleotide sequence encoding the amino acid sequence of SEQ ID NO:38 is represented by SEQ ID NO:57.

(2) Designing of Amino Acid Sequence of VL of Human CDR-grafted Antibody for CCR4

Next, an amino acid sequence of VL of an anti-CCR4 CDR-grafted antibody was designed as follows. An amino acid sequence of FR of VL of a human antibody was selected for grafting amino acid sequences of CDR1, 2 and 3 of VL of anti-CCR4 mouse antibody KM2160 represented by SEQ ID NOs:5, 6 and 7, respectively Kabat et al. have classified the VL of various already known human antibodies into four subgroups (HSG I to IV) based on the homology of their amino acid sequences and reported common sequences in each subgroup (*Sequences of Proteins of Immunological Interest*, US Dep. Health and Human Services, 1991) Accordingly, among FR amino acid sequences of the common sequences of four subgroups of the human antibody VL, an FR amino acid sequence having the highest homology with the FR amino acid sequence of VL of KM2160 was selected. Table 2 shows a result of the retrieval of homology between the FR amino acid sequences of the common sequence of each subgroup of the human antibody VL and the FR amino acid sequence of VL of KM2160. As shown in Table 2, the FR amino acid sequence of VL of KM2160 showed the highest homology with the subgroup II.

TABLE 2

| HSG I | HSG II | HSG III | HSG IV |
|---|---|---|---|
| 65.00% | 82.50% | 65.00% | 72.50% |

Based on the above results, the VL amino acid sequence LV0 of anti-CCR4 CDR-grafted antibody represented by SEQ ID NO:8 was designed by grafting the amino acid sequences of CDR1, 2 and 3 of VL of anti-CCR4 mouse antibody KM2160 represented by SEQ ID NOs:5, 6 and 7, respectively, to appropriate positions in the amino acid sequence of FR of the common sequence of subgroup II of the human antibody VL. A nucleotide sequence encoding the amino acid sequence of SEQ ID NO:8 is represented by SEQ ID NO:53.

(3) Modification of VH and VL of Human CDR-grafted Antibody for CCR4

The VH amino acid sequences Gal0 and HV0, and VL amino acid sequence LV0 of anti-CCR4 CDR-grafted antibody designed in the above are antibodies in which the CDR amino acid sequence of the anti-CCR4 mouse antibody KM2160 alone is grafted to the selected FR amino acid sequences of human antibody. However, when grafting with only CDR amino acid sequence of a mouse antibody is carried out, the activity of a human CDR-grafted antibody is frequently decreased so that, in order to avoid the decrease, certain amino acid residues among the FR amino acid residues different between a human antibody and a mouse antibody, which are considered to have influences on the activity, are generally grafted together with the CDR amino acid sequence. Accordingly, in this Example, an examination was carried out to identify the FR amino acid residues considered to have influences on the activity.

First, three-dimensional structures of antibody V regions (Gal0LV0 and HV0LV0) comprising amino acid sequences Gal0 and HV0 of VH and amino acid sequence LV0 of VL in the anti-CCR4 CDR-grafted antibody designed in the above were constructed using a computer modeling technique The three-dimensional structure coordinates were prepared using a software AbM (manufactured by Oxford Molecular), and display of the three-dimensional structures using a software Pro-Explore (manufactured by Oxford Molecular) or RasMol (manufactured by Glaxo) according to the respective attached manufacture's instructions. Also, computer models of the three-dimensional structures of V regions of anti-CCR4 mouse antibody KM2160 were constructed in the same manner. In addition, three-dimensional structure models comprising modified amino acid sequences were constructed in the same manner, in which certain residues of the FR amino acid sequences of VH and VL of Gal0LV0 or HV0LV0, different from the anti-CCR4 mouse antibody KM2160, were substituted with other residues found at corresponding positions in the anti-CCR4 mouse antibody KM2160, and the three-dimensional structures of V regions of the anti-CCR4 mouse antibody KM2160, Gal0LV0 or HV0LV0 and the modified product were compared.

As a result, the three-dimensional structure of the antigen binding region was changed so that Ala at position 40, Gly at position 42, Lys at position 43, Gly at position 44 and Lys at position 76 and Ala at position 97 in Gal0, Thr at position 28 and Ala at position 97 for HV0 and Ile at position 2, Val at position 3, Gln at position 50 and Val at position 88 in LV0 were selected as residues considered to have influence on the activity of antibody among the FR amino acid residues of Gal0LV0 or HV0LV0. Among these selected amino acid residues, at least one amino acid is modified into an amino acid residue(s) found in the mouse antibody KM2160 so that VH and VL of human CDR-grafted antibody having various modifications were designed.

First, regarding the VH, for example, Gal1 represented by SEQ ID NO:9 in which Ala at position 97 of Gal0 was modified, Gal2 represented by SEQ ID NO:10 in which Gly at position 42 and Gly at position 44 of Gal0 were modified, Gal3 represented by SEQ ID NO:11 in which Ala at position 97, Gly at position 42 and Gly at position 44 of Gal0 were modified, HV1 represented by SEQ ID NO:39 in which Thr at position 28 of HV0 was modified, HV2 represented by SEQ ID NO:40 in which Ala at position 97 of HV0 was modified, and HV3 represented by SEQ ID NO:41 in which Thr at position 28 and Ala at position 97 of HV0 were modified were designed. Furthermore, regarding the VL, for example, LV1 represented by SEQ ID NO:12 in which Ile at position 2 was modified, LV2 represented by SEQ ID NO:13 in which Val at position 3 was modified, and LV3 represented by SEQ ID NO:14 in which Ile at position 2 and Val at position 3 were modified were designed. Nucleotide sequences encoding the amino acid sequences represented by SEQ ID NOs:9 to 11, 39 to 41 and 12 to 14 are represented by SEQ ID NOs:50 to 52, 58 to 60 and 54 to 56, respectively.

2. Construction of cDNA Encoding Anti-CCR4 CDR-grafted Antibody (1) Construction of cDNA Encoding VH of Anti-CCR4 CDR-grafted Antibody cDNA encoding the amino acid sequence Gal0 of VH of the anti-CCR4 CDR-grafted antibody designed in 1(1) of Example 1 was constructed using PCR as follows.

First, a complete antibody amino acid sequence by ligating the designed amino acid sequence with the H chain secretory signal sequence of anti-CCR4 mouse antibody KM2160 represented by SEQ ID NO:15, Next, the amino acid sequence was converted into genetic codons. When two or more genetic codons are present for one amino acid residue, a corresponding genetic codon was determined by taking into consideration the codon usage found in nucleotide sequences of antibody genes (*Sequences of Proteins of Immunological Interest*, US Dep. Health and Human Services, 1991). A nucleotide sequence of cDNA encoding the amino acid sequence of complete antibody V region was designed by ligating the determined genetic codons, and binding nucleotide sequences of primers for PCR amplification (including restriction enzyme recognition sequences for cloning into a vector for humanized antibody expression) were added to its 5'-terminal and 3'-terminal. The designed nucleotide sequence was divided into a total of 6 nucleotide sequences each having about 100 nucleotides counting from the 5'-terminal (adjoining nucleotide sequences are designed such that they have a complementary sequence of about 20 nucleotides on their terminal), and 6 synthetic oligonucleotides of SEQ ID NOs:16, 17, 18, 19, 20 and 21 were synthesized in reciprocal orders of a sense chain and an antisense chain (manufactured by GENSET).

PCR was carried out by adding each oligonucleotide to a reaction solution containing 0.2 mM dNTPs and 1 mM magnesium chloride to give a final concentration of 0.1 μM, and adjusting the total volume to 50 μl using 0.4 μM M13 primer RV (manufactured by Takara Shuzo), 0.4 μM M 13 primer M3 (manufactured by GENSET) and 2.5 units of KOD polymerase (manufactured by TOYOBO). The reaction was carried out by 30 cycles, each cycle consisting of 94° C. for 30 seconds, 55° C. for 30 seconds and 74° C. for 60 seconds, and then 1 cycle at 74° C. for 10 minutes. The reaction solution was purified using QIA quick PCR purification kit (manufactured by QIAGEN) and finally dissolved in sterile water. The reaction solution was allowed to react at 37° C. for 1 hour using 10 units of a restriction enzyme ApaI (manufactured by Takara Shuzo) and 10 units of a restriction enzyme NotI (manufactured by Takara Shuzo). The reaction solution was fractionated by agarose gel electrophoresis, and an ApaI-NotI fragment of about 0.47 kb was recovered.

Next, 3 μg of plasmid pBluescript II SK(−) (manufactured by Stratagene) was allowed to react with the fragment using 10 units of a restriction enzyme ApaI (manufactured by Takara Shuzo) and 10 units of a restriction enzyme NotI (manufactured by Takara Shuzo) at 37° C. for 1 hour. Said reaction solution was fractionated by agarose gel electrophoresis, and an ApaI-NotI fragment of about 2.95 kb was recovered.

Next, the resulting ApaI-NotI fragment of the PCR product of VH of the anti-CCR4 CDR-grafted antibody and the ApaI-NotI fragment of plasmid pBluescript II SK(−) were ligated using Solution I of DNA Ligation Kit Ver. 2 (manufactured by Takara Shuzo) according to the manufacture's instructions. *Escherichia coli* DH5α (manufactured by TOYOBO) was transformed using the recombinant plasmid DNA solution obtained in this manner, each plasmid DNA was prepared from the transformant clones and the nucleotide sequences were analyzed using Big Dye Terminator Kit ver. 2 (manufactured by Applied Biosystems). As a result of the nucleotide sequence analysis, a plasmid pKM2160Gal0 shown in FIG. 1 having the objective nucleotide sequence was obtained. *Escherichia coli* transformed with pKM2160Gal0, *Escherichia coli* DH5α/pKM2160Gal0, has been deposited on Aug. 22, 2001, as FERM BP-7709 in International Patent Organism Depositary, National Institute of Advanced Industrial Science and Technology (AIST Tsukuba Central 6, 1-1, Higashi 1-Chrome Tsukuba-shi, Ibaraki-ken 305-8566 Japan).

Next, the FR amino acid residues designed in 1(3) of Example1 was modified as follows. The genetic codons for amino acid residues after the modification were modified to have genetic codons found in the mouse antibody KM2160.

In modification of Ala at position 97 to Gly, the PCR was carried out using 25 ng of the plasmid pKM2160Gal0 prepared in this item as the template, first heating at 94° C. for 2 minutes and then carrying out 35 cycles of the reaction, each cycle consisting of 94° C. for 15 seconds, 55° C. for 30 seconds and 68° C. for 40 seconds, in 50 μl of a reaction system prepared by adding each of the synthetic DNAs for gene transfer comprising the nucleotide sequences represented by SEQ IDs:22 and 23 (manufactured by GENSET) as primers to give a final concentration of 0.4 μM and using 2.5 units of KOD plus polymerase (manufactured by TOYOBO) according to the manufacture's instructions The reaction solution was purified using QIA quick PCR purification kit (manufactured by QIAGEN) and finally dissolved in sterile water. The total volume was allowed to react for 1 hour at 37° C. using 10 units of a restriction enzyme PstI (manufactured by Takara Shuzo) and then allowed to react for 1 hour at 37° C. using 10 units of a restriction enzyme DraIII (manufactured by New England Biolabs). The reaction solution was fractionated by agarose gel electrophoresis, and a PstI-DraIII fragment of about 0.58 kb was recovered.

Next, 3 μg of the plasmid pKM2160Gal0 was allowed to react at 37° C. for 1 hour using 10 units of a restriction enzyme PstI (manufactured by Takara Shuzo) and then to undergo the reaction at $_{37}$° C. for 1 hour using 10 units of a restriction enzyme DraIII (manufactured by New England Biolabs). The reaction solution was fractionated by agarose gel electrophoresis, and a PstI-DraIII fragment of about2.7 kb was recovered.

Figure 2:
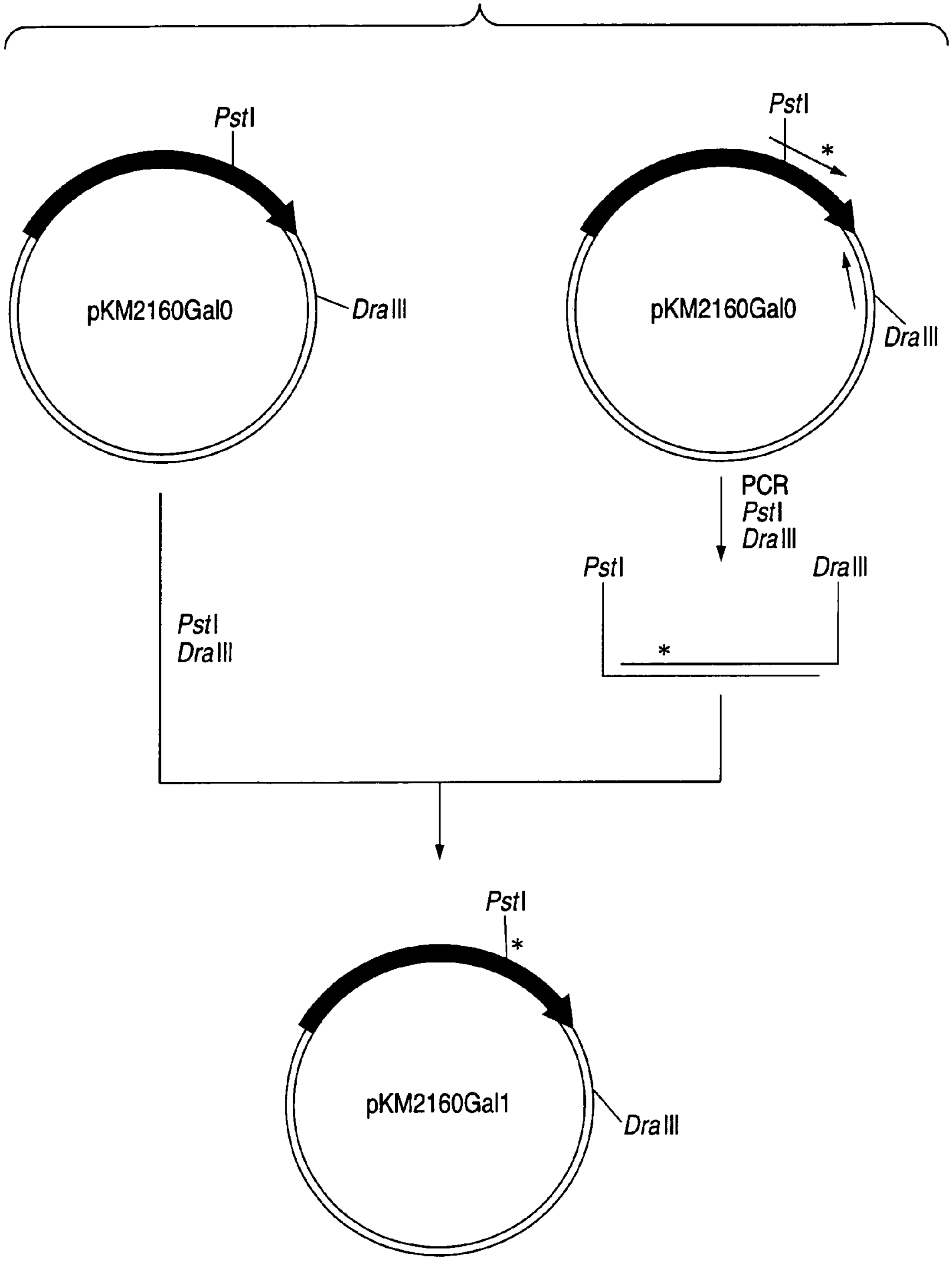
FIG. 2 shows construction steps of a plasmid pKM2160Gal1. The symbol * shows the position of mutation genetic codon modifying an amino acid residue

Next, the thus obtained PstI-DraIII fragment derived from the PCR product and the PstI-DraIII fragment derived from the plasmid pKM2160Gal0 were ligated using Solution I of DNA Ligation Kit Ver. 2 (manufactured by Takara Shuzo) according to the manufacture's instructions. *Escherichia coli* DH5α (manufactured by TOYOBO) was transformed using the recombinant plasmid DNA solution obtained in this manner, each plasmid DNA was prepared from the transformant clones and the nucleotide sequences were analyzed using Big Dye Terminator Kit ver. 2 (manufactured by Applied Biosystems). As a result of the nucleotide sequence analysis, a plasmid pKM2160Gal1 shown in FIG. 2 having the objective nucleotide sequence was obtained. *Escherichia coli* transformed with the plasmid pKM2160Gal1, *Escherichia coli* DH5α/pKM2160Gal1, has been deposited on Aug. 22, 2001, as FERM BP-7710 in International Patent Organism Depositary, National Institute of Advanced Industrial Science and Technology (AIST Tsukuba Central 6, 1-1, Higashi 1-Chrome Tsukuba-shi, Ibaraki-ken 305-8566 Japan).

In modifications of Gly at position 42 to Asp and Gly at position 44 into Arg, a plasmid pKM2160Gal2 was obtained by carrying out the method basically similar to the above, except that the synthetic DNA for gene transfer comprising the nucleotide sequence represented by SEQ ID NO:24 (manufactured by GENSET) and M13 primer RV (manufactured by Takara Shuzo) were used as the PCR primers *Escherichia coli* transformed with the plasmid pKM2160Gal2, *Escherichia coli* DH5α/pKM2160Gal2, has been deposited on Aug. 22, 2001, as FERM BP-7711 in International Patent Organism Depositary, National Institute of Advanced Industrial Science and Technology (AIST Tsukuba Central 6, 1-1, Higashi 1-Chrome Tsukuba-shi, Ibaraki-ken 305-8566 Japan).

Figure 3:
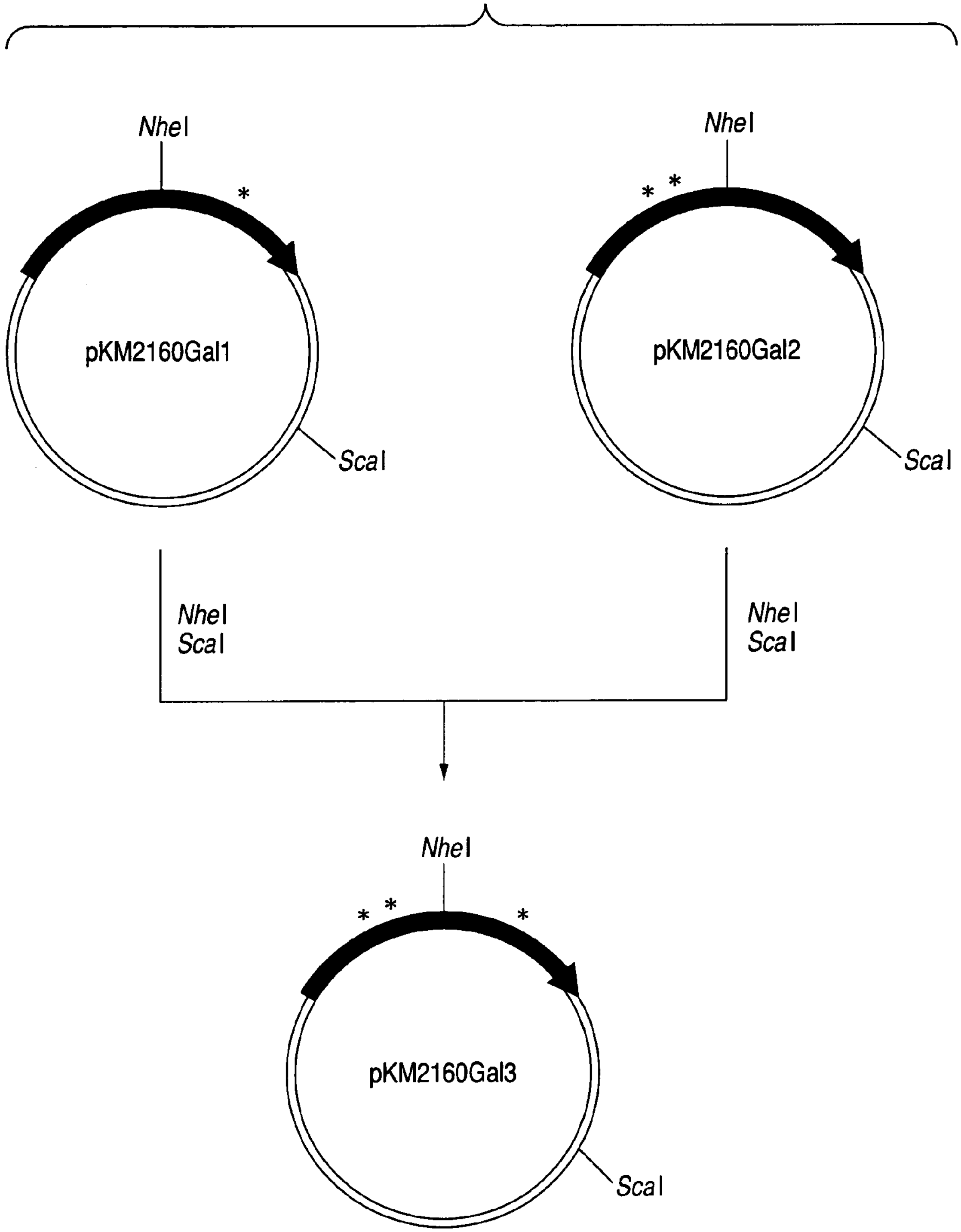
FIG. 3 shows construction steps of a plasmid pKM2160Gal3. The symbol * shows the position of mutation genetic codon modifying an amino acid residue.

Also, modification of all of the above three residues was constructed as follows. About 0.5 μg of each of the pKM2160Gal1 and pKM2160Gal2 obtained in the above was allowed to react at 37° C. for 1 hour using 10 units of NheI (manufactured by Takara Shuzo) and then allowed to react at 37° C. for 1 hour using ScaI (manufactured by Takara Shuzo). The reaction solution was fractionated by agarose gel electrophoresis, and a NheI-ScaI fragnent of about 1.3 kb derived from pKM2160Gal1 and a fragment of about 2.0 kb derived from pKM2160Gal2 were recovered. The resulting two fragments were ligated using Solution I of DNA Ligation Kit Ver. 2 (manufactured by Takara Shuzo) according to the manufacture's instructions *Escherichia coli* DH5α (manufactured by TOYOBO) was transformed using the recombinant plasmid DNA solution obtained in this manner, each plasmid DNA was prepared from the transformant clones and nucleotide sequences were analyzed using Big Dye Terminator Kit ver. 2 (manufactured by Applied Biosystems) As a result of the nucleotide sequence analysis, a plasmid pKM2160Gal3 shown in FIG. 3 having the objective nucleotide sequence was obtained. *Escherichia coli* transformed with the plasmid pKM2160Gal3, *Escherichia coli* DH5α/pKM2160Gal3, has been deposited on Aug. 22, 2001, as FERM BP-7712 in International Patent Organism Depositary, National Institute of Advanced Industrial Science and Technology (AIST Tsukuba Central 6, 1-1, Higashi 1-Chome Tsukuba-shi, Ibaraki-ken 305-8566 Japan).

Next, a cDNA encoding the amino acid sequence HV0 of VH of the anti-CCR4 CDR-grafted antibody designed in 1(1) of Example1 was constructed using PCR as follows.

First, a complete antibody amino acid sequence by ligating the designed amino acid sequence with the H chain secretory signal sequence of anti-CCR4 mouse antibody KM2160 represented by SEQ ID NO:15. Next, the amino acid sequence was converted into genetic codons When two or more genetic codons are present for one amino acid residue, a corresponding genetic codon was determined by taking into consideration the codon usage found in nucleotide sequences of antibody genes (*Sequences of Proteins of Immunological Interest*, US Dep. Health and Human Services, 1991). The determined genetic codons were ligated so that a nucleotide sequence of cDNA encoding the amino acid sequence of complete antibody V region was designed, and adding nucleotide sequences of primers for PCR amplification (including restriction enzyme recognition sequences for cloning into a vector for humanized antibody expression use) were added to its 5'-terminal and 3'-terminal The designed nucleotide sequence was divided into a total of 6 nucleotide sequences each having about 100 nucleotides counting from the 5'-terminal (adjoining nucleotide sequences are designed such that they have a duplication sequence of about 20 nucleotides on their termini) and 6 synthetic oligonucleotides of SEQ ID NOs:16, 42, 43, 44, 45 and 21 were synthesized in reciprocal orders of a sense chain and an antisense chain (manufactured by GENSET), and then pKM2160HV0 was obtained by the method similar to pKM2160Gal0 described in this item. *Escherichia coli* transformed with the plasmid pKM2160HV0, *Escherichia coli* DH5α/pKM2160HV0, has been deposited on Aug. 27, 2001, as FERM BP-7718 in International Patent Organism Depositary, National Institute of Advanced Industrial Science and Technology (AIST Tsukuba Central 6, 1-1, Higashi 1-Chome Tsukuba-shi, lbaraki-ken 305-8566 Japan).

In modification of Thr at position 28 to lie, pKM2160HV1 having the objective nucleotide sequence was obtained by carrying out the reaction similar to the construction of the above plasmid pKM2160HV0, using an oligonucleotide having the nucleotide sequence represented by SEQ ID NO:69 instead of the oligonucleotide having the nucleotide sequence represented by SEQ ID NO:42, and using an oligonucleotide having the nucleotide sequence represented by SEQ ID NO:46 instead of the oligonucleotide having the nucleotide sequence represented by SEQ ID NO:43 *Escherichia coli* transformed with the plasmid pKM2160HV1, Escherichia coli DHR5αpKM2160HV1, has been deposited on Aug. 27, 2001, as FERM BP-7719 in International Patent Organism Depositary, National Institute of Advanced Industrial Science and Technology (AIST Tsukuba Central 6, 1-1, Higashi 1 -Chome Tsukuba-shi, Ibaraki-ken 305-8566 Japan).

In modification of Thr at position 28 to Ile and Ala at position 97 to Gly, pKM2160HV3 having the objective nucleotide sequence was obtained by the reaction similar to the construction of the above plasmid pKM2160HV0,using an oligonucleotide having the nucleotide sequence represented by SEQ ID NO:69 instead of the oligonucleotide having the nucleotide sequence represented by SEQ ID NO:42, using an oligonucleotide having the nucleotide sequence represented by SEQ ID NO:46 instead of the oligonucleotide having the nucleotide sequence represented by SEQ ID NO:43 and using an oligonucleotide having the nucleotide sequence represented by SEQ ID NO:47 instead of the oligonucleotide having the nucleotide sequence represented by SEQ ID NO:45. *Escherichia coli* transformed with the plasmid pKM2160HV3, *Escherichia coli* DH5α/pKM2160HV3, has been deposited on Aug. 27, 2001, as FERM BP-7721 in International Patent Organism Depositary, National Institute of Advanced Industrial Science and Technology (AIST Tsukuba Central 6, 1 -1, Higashi 1-Chome Tsukuba-shi, Ibaraki-ken 305-8566 Japan).

In modification of Ala at position 97 to Gly, the plasmid was constructed as follows. About 0.5 μg of each of the obtained pKM2160HV0 and pKM2160HV3 was allowed to react at 37° C. for 1 hour using 10 units of a restriction enzyme NheI (manufactured by Takara Shuzo) and then allowed to react at 37° C. for 1 hour using ScaI (manufactured by Takara Shuzo). The reaction solution was fractionated by agarose gel electrophoresis, and a NheI-ScaI fragment of about 1.3 kb derived from pKM 2160HV3 and a fragment of about 2.0 kb derived from pKM 2160HV0 were recovered. The resulting two fragments were ligated using Solution I of DNA Ligation Kit Ver. 2 (manufactured by Takara Shuzo) according to the manufacture's instructions. *Escherichia coli* DH5α (manufactured by TOYOBO) was transformed using the recombinant plasmid DNA solution obtained in this manner, each plasmid DNA was prepared from the transformant clones and nucleotide sequences were analyzed using Big Dye Terminator Kit ver. 2 (manufactured by Applied Biosystems). As a result of the nucleotide sequence analysis, a plasmid pKM2160HV2 having the objective nucleotide sequence was obtained. *Escherichia coli* transformed with the plasmid pKM2160HV2, *Escherichia coli* DH5α/pKM2160HV2, has been deposited on Aug. 27, 2001, as FERM BP-7720 in International Patent Organism Depositary, National Institute of Advanced Industrial Science and Technology (AIST Tsukuba Central 6, 1-1, Higashi 1-Chome Tsukuba-shi, Ibaraki-ken 305-8566 Japan).

(2) Construction of cDNA Encoding VL of Anti-CCR4 CDR-grafted Antibody

A cDNA encoding the amino acid sequence LV0 of VL of the anti-CCR4 CDR-grafted antibody designed in 1(2) of Example 1 was constructed using PCR similar to the case of VH as follows. In this case, the L chain sequence of anti-CCR4 mouse antibody KM2160 having the amino acid sequence represented by SEQ ID NO:25 was used as the secretory signal sequence.

First, 6 synthetic oligonucleotides having the nucleotide sequences described in SEQ ID NOs:26, 27, 28, 29, 30 and 31 were synthesized (manufactured by GENSET). PCR was carried out by adding each oligonucleotide to 50 μl of a reaction solution to give a final concentration of 0.1 μM, and using 0.4 μM of M13 primer RV (manufactured by Takara Shuzo) and 0.4 μM of M13 primer M4 (manufactured by Takara Shuzo) or M 13 primer M3 (manufactured by GENSET) represented by SEQ ID NO:32 and 2.5 units of KOD polymerase (manufactured by TOYOBO). The reaction was carried out by 30 cycles, each cycle consisting of 94° C. for 30 seconds, 55° C. for 30 seconds and 74° C. for 60 seconds, and subsequent 1 cycle at 72° C. for 10 minutes. The reaction solution was purified using QIA quick PCR purification kit (manufactured by QIAGEN) and finally dissolved in sterile water. The reaction solution was allowed to react using 10 units of a restriction enzyme EcoRI (manufactured by Takara Shuzo) and 10 units of a restriction enzyme XhoI (manufactured by Takara Shuzo) at 37° C. for 1 hour. The reaction solution was fractionated by agarose gel electrophoresis, and an EcoRI-XhoI fragment of about 0.44 kb was recovered.

Next, 3 μg of the plasmid pBluescript II SK(−) (manufactured by Stratagene) was allowed to react using 15 units of a restriction enzyme EcoRI (manufactured by Takara Shuzo) and 15 units of a restriction enzyme XhoI of (manufactured by Takara Shuzo) at 37° C. for 1 hour. The reaction solution was fractionated by agarose gel electrophoresis, and an EcoRI-XhoI fragment of about 2.95 kb was recovered.

Figure 4:
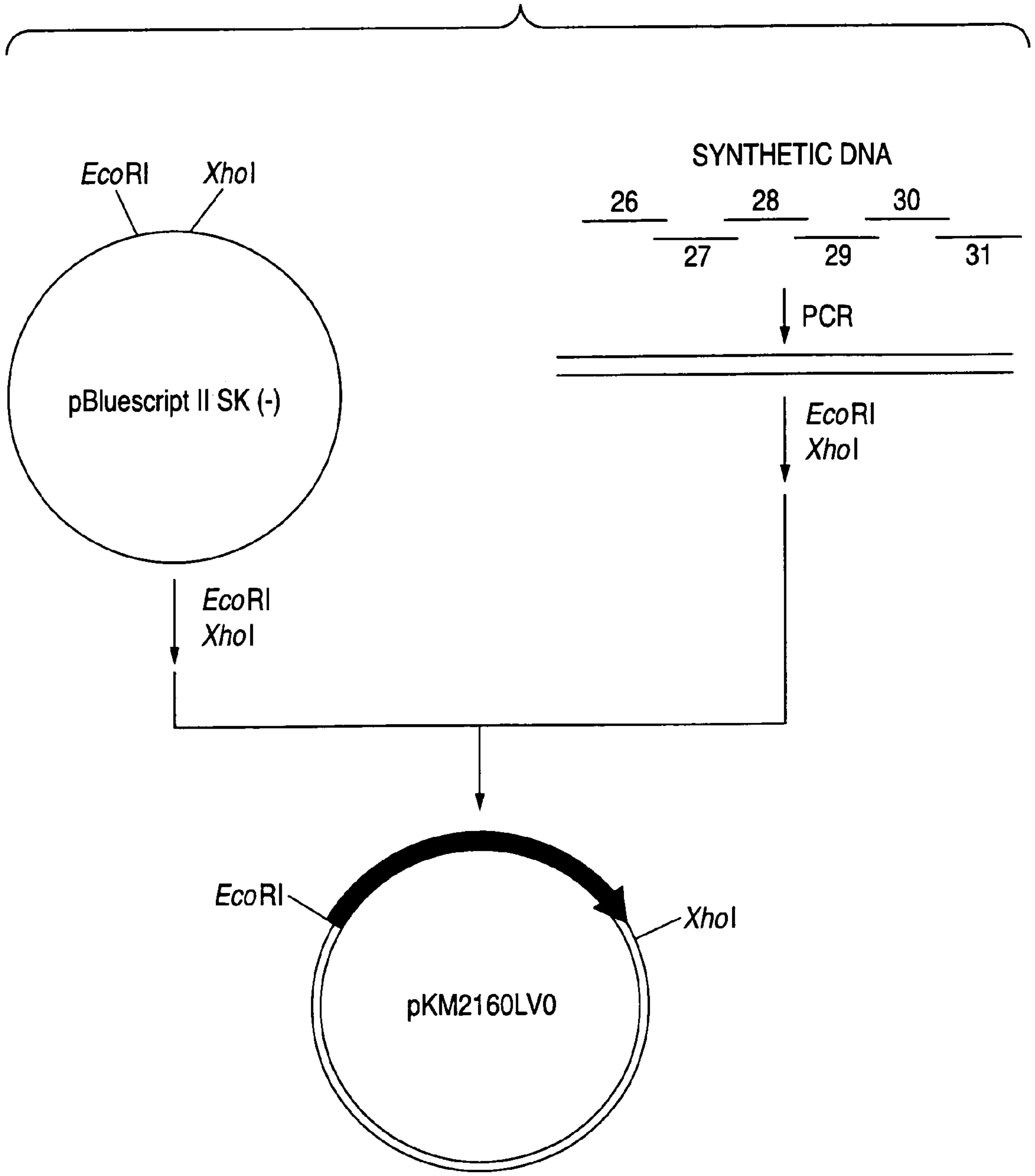
FIG. 4 shows construction steps of a plasmid pKM2160LV0.

Next, the resulting EcoRI-XhoI fragment of the PCR product of VL of the anti-CCR4 CDR-grafted antibody and the EcoRI-XhoI fragment of plasmid pBluescript II SK(−) were ligated using Solution1 of DNA Ligation Kit Ver. 2 (manufactured by Takara Shuzo) according to the manufacture's instructions. *Escherichia coli* DH5α (manufactured by TOYOBO) was transformed using the recombinant plasmid DNA solution obtained in this manner, each plasmid DNA was prepared from the transformant clones and nucleotide sequences were analyzed using Big Dye Terminator Kit ver. 2 (manufactured by Applied Biosystems). As a result of the nucleotide sequence analysis, a plasmid pKM2160LV4 shown in FIG. 4 having the objective nucleotide sequence was obtained. *Escherichia coli* transformed with pKM2160LV0, *Escherichia coli* DH5α/pKM2160LV0, has been deposited on Aug. 22, 2001, as FERM BP-7713 in International Patent Organism Depositary, National Institute of Advanced Industrial Science and Technology (AIST Tsukuba Central 6, 1 -1, Higashi 1-Chome Tsukuba-shi, Ibaraki-ken 305-8566 Japan).

Next, the FR amino acid residues designed in 1(3) of Example1 were modified as follows The genetic codons for amino acid residues after the modification were modified to have genetic codons found in the mouse antibody KM2160.

Figure 5:
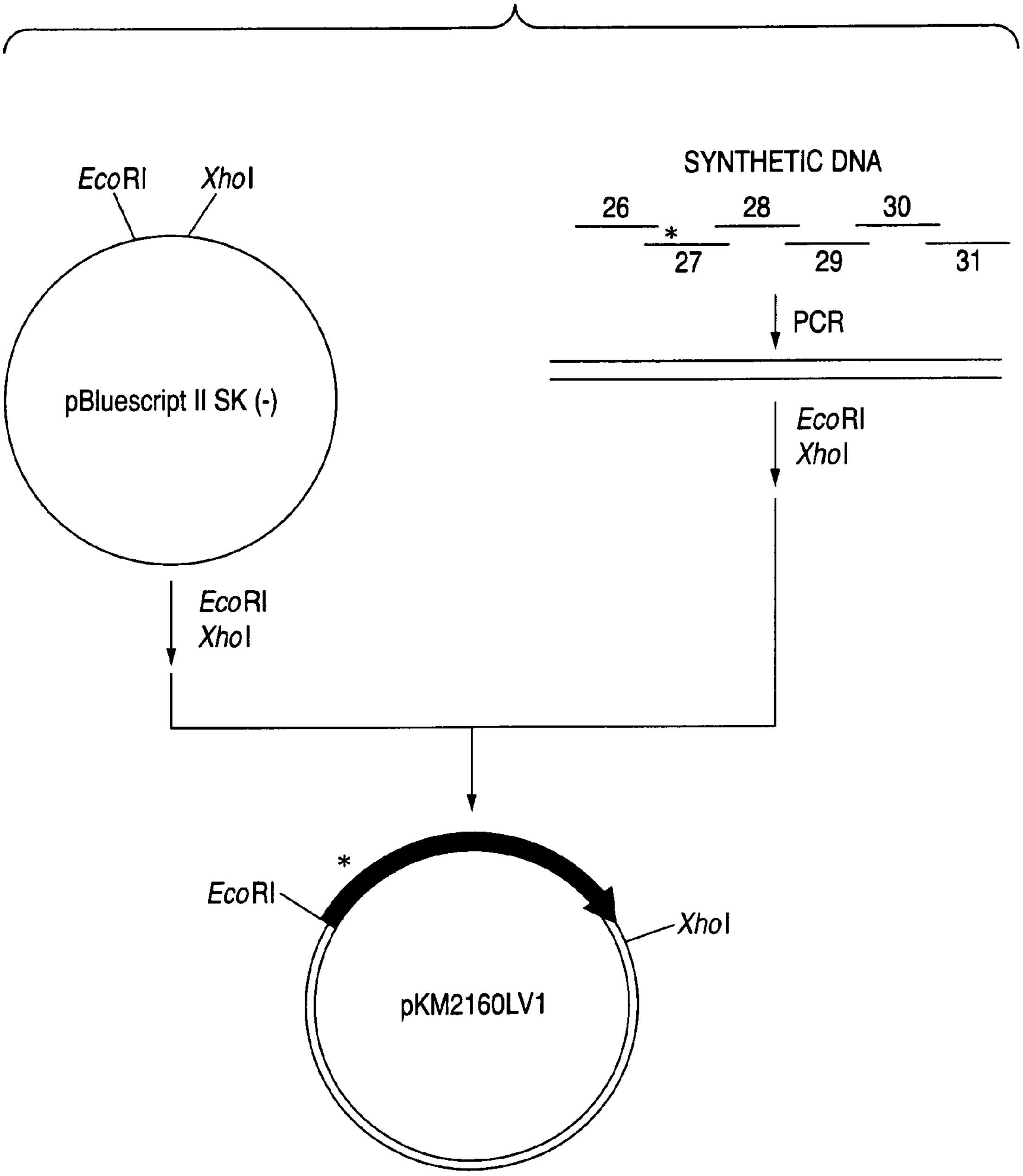
FIG. 5 shows construction steps of a plasmid pKM2160LV1. The symbol * shows the position of mutation genetic codon modifing an amino acid residue.

In modification of Ile at position 2 to Val , a plasmid pKM2160LV1 shown in FIG. 5 having the objective nucleotide sequence was obtained by carrying out the reaction similar to the construction of the above plasmid pKM 2160LV0, using an oligonucleotide having the nucleotide sequence represented by SEQ ID NO:33 instead of the oligonucleotide having the nucleotide sequence represented by SEQ ID NO:27. *Escherichia coli* transformed with the plasmid pKM2160LV1, *Escherichia coli* DH5αpKM2160LV1, has been deposited on Aug. 22, 2001, as FERM BP-7714 in International Patent Organism Depositary, National Institute of Advanced Industrial Science and Technology (AIST Tsukuba Central 6, 1-1, Higashi 1-Chome Tsukuba-shi, Ibaraki-ken 305-8566 Japan), In the same manner, each of the objective plasmids pKM2160LV2 and pKM2160LV3 was obtained by using an oligonucleotide having the nucleotide sequence represented by SEQ ID NO:34 instead of the oligonucleotide having the nucleotide sequence represented by SEQ ID NO.27 when Va1 at position 3 was modified into Leu, and using an oligonucleotide having the nucleotide sequence represented by SEQ ID NO:35 instead of the oligonucleotide having the nucleotide sequence represented by SEQ ID NO:27 when both of the above two residues were modified. *Escherichia coli* transformed with the plasmid pKM2160LV2, *Escherichia coli* DH5α/pKM2160LV2, and *Escherichia coli* transformed with the plasmid pKM2160LV3, *Escherichia coli* DH5α/pKM2160LV3, have been deposited on Aug. 22, 2001, as FERM BP-7715 and FERM BP-7716, respectively, in International Patent Organism Depositary, National Institute of Advanced Industrial Science and Technology (AIST Tsukuba Central 6, 1-1, Higashi 1-Chome Tsukuba-shi, Ibaraki-ken 305-8566 Japan).

(3) Construction of Anti-CCR4 CDR-grafted Antibody Expression Vector

An anti-CCR4 CDR-grafted antibody expression vector pKANTEX2160Gal0LV0 was constructed using a vector for humanized antibody expression pKANTEX93 (*Mol. Immu-*

*nol.*, 37, 1035 (2000)) and the plasmids pKM2160Gal0 and pKM2160LV0 obtained in 2(1) and (2) of Example 1 as follows.

The plasmid pKM2160LV0 (3 μg) obtained in 2(2) of Example 1 was allowed to react with 10 units of a restriction enzyme BsiWI (manufactured by New England Biolabs) at 55° C. for 1 hour and then with 10 units of a restriction enzyme EcoRI (manufactured by Takara Shuzo) at 37° C. for 1 hour The reaction solution was fractionated by agarose gel electrophoresis, and a BsiWI-EcoRI fragment of about 0.44 kb was recovered.

Next, 3 μg of the vector for humanized antibody expression pKANTEX93 was allowed to react with 10 units of a restriction enzyme BsiWI (manufactured by New England Biolabs) at 55° C. for 1 hour and then with 10 units of a restriction enzyme EcoRI (manufactured by Takara Shuzo) at 37° C. for 1 hour. The reaction solution was fractionated by agarose gel electrophoresis, and a BsiWI-EcoRI fragment of about 12.75 kb was recovered.

Figure 6:
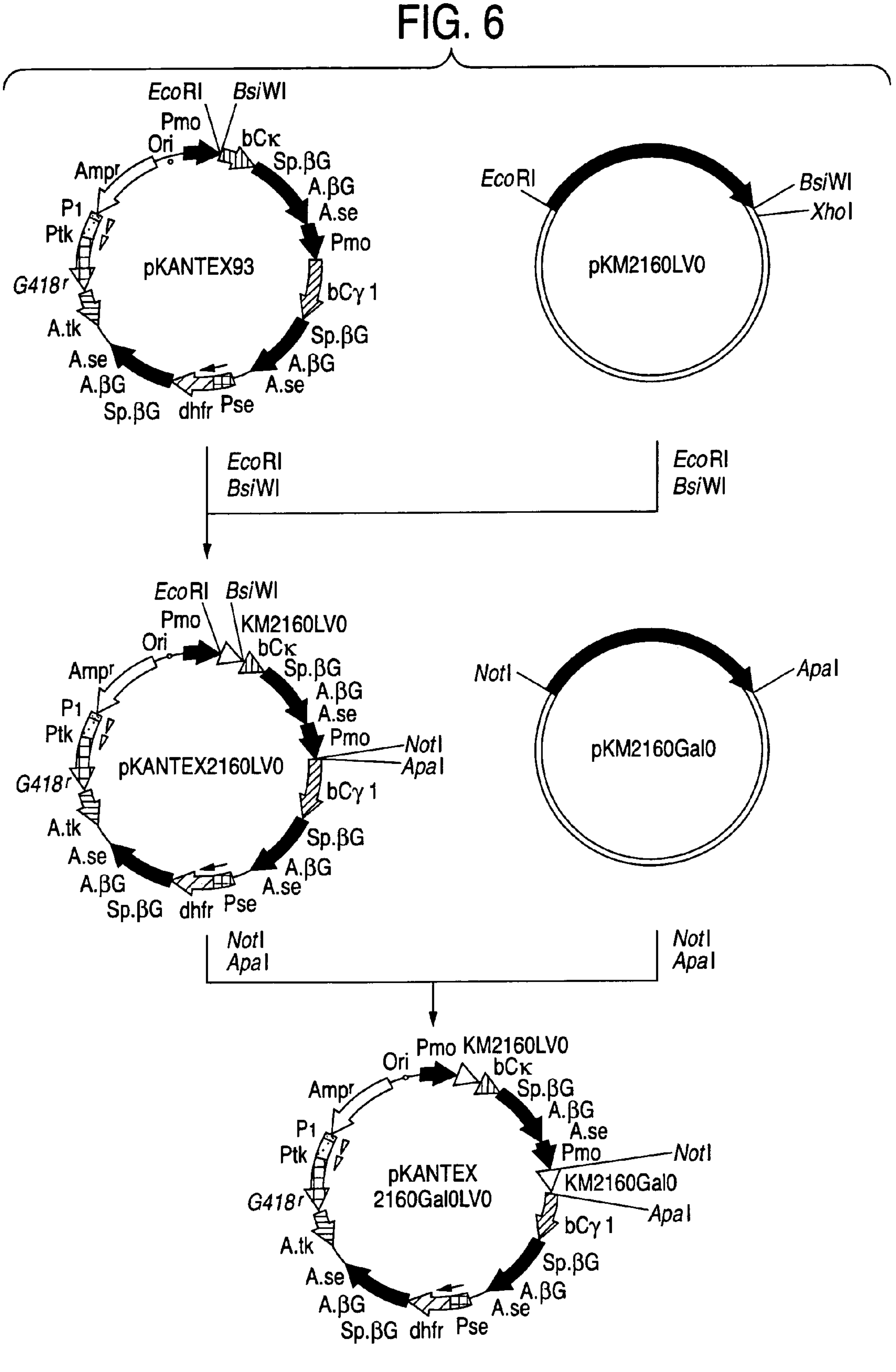
FIG. 6 shows construction steps of a plasmid pKANTEX2160LV0 and plasmid pKANTEX2160Gal0LV0.

Next, the resulting BsiWI-EcoRI fragment derived from pKM2160LV0 and the BsiWI-EcoRI fragment derived from pKANTEX93 were ligated using Solution I of DNA Ligation Kit Ver. 2 (manufactured by Takara Shuzo) according to the manufacture's instructions, *Escherichia coli* DH15α (manufactured by TOYOBO) was transformed using the recombinant plasmid DNA solution obtained in this manner to thereby obtain a plasmid pKANTEX2160LV0 shown in FIG. 6.

Next, 3 μig of the plasmid pKM2160Gal0 obtained in 2(1) of Example1 was allowed to react with 10 units of a restriction enzyme ApaI (manufactured by Takara Shuzo) at 37° C. for 1 hour and then with 10 units of a restriction enzyme NotI (manufactured by Takara Shuzo) at 37° C. for 1 hour. The reaction solution was fractionated by agarose gel electrophoresis, and an ApoI-NotI fragment of about 0.47 kb was recovered.

Next, 3 μg of the plasmid pKANTEX 2160LV0 obtained in the above was allowed to react with 10 units of a restriction enzyme ApaI (manufactured by Takara Shuzo) at 37° C. for 1 hour and then with 10 units of a restriction enzyme NotI (manufactured by Takara Shuzo) at 37° C. for 1 hour. The reaction solution was fractionated by agarose gel electrophoresis, and an ApaI-NotI fragment of about 0.45 kb was recovered.

Next, the resulting ApaI-NotI fragment derived from the pKM 2160Gal0 and the ApaI-NotI fragment derived from the plasmid pKANTEX2160LV0 were ligated using Solution I of DNA Ligation Kit Ver. 2 (manufactured by Takara Shuzo) according to the manufacture's instructions. *Escherichia coli* DH5α (manufactured by TOYOBO) was transformed using the recombinant plasmid DNA solution obtained in this manner, and each plasmid DNA was prepared from the transformant clones.

As a result that the nucleotide sequences of the thus obtained plasmids were analyzed using Big Dye Terminator Kit ver. 2 (manufactured by Applied Biosystems), it was confirmed that an expression vector pKANTEX2160Gal0LV0 shown in FIG. 6 into which the objective DNA had been cloned was obtained.

In addition, expression vectors were prepared using the same method on the VH and VL in which amino acid residues of other FR were modified, including HV0.

Specifically, 22 expression vectors pKM2160Gal0LV0, pKM2160Gal0LV1, pKM2160Gal0LV2, pKM2160Gal0LV3, pKM2160Gal1 LV1, pKM2160Gal1 LV3, pKM2160Gal2LV1, pKM2160Gal2LV3, pKM2160Gal3LV 1, pKM2160Gal3LV3, pKM2160HV0LV0, pKM2160HV0LV1, pKM2160HV0LV2, pKM2160HV0LV3, pKM2160HV1LV0, pKM2160HV1LV1, pKM2160HV1LV2, pKM2160HV1LV3, pKM2160HV2LV0, pKM2160HV2LV3, pKM2160HV3LV0and pKM2160HV3LV 3 were constructed by respectively combining pKM2160Gal0, pKM2160Gal1, pKM2160Gal2, pKM2160Gal3, pKM2160HV0, pKM2160HV1, pKM2160HV2 and pKM2160HV3 constructed in 2(1) of Example1 with the pKM2160LV0, pKM2160LV1, pKM2160LV2 and pKM2160LV3 constructed in 2(2) of Example 1.

EXAMPLE 2

Expression of Anti-CCR4 CDR-grafted Antibody in Animal Cells:

1. Transient Expression of Anti-CCR4 CDR-grafted Antibody using COS-7 Cell (ATCC CRL 1651)

(1) Transient Expression at COS-7 Cell

Into a 6 well plate (manufactured by Iwaki Glass), $1\times10^5$ cells/ml of COS-7 cell was dispensed at 2 ml/well using DMEM medium (manufactured by Bibco) containing 10% FCS and cultured overnight at 37° C. Per 100 μl of OPTI-MEM medium (manufactured by Bibco), 3 μl of Fu-GENETM 6 Transfer Reagent (manufactured by Roche) was added and 1 μg of each of the 22 anti-CCR4 CDR-grafted antibody expression vectors obtained in the article 2(3) of Example1 was further added thereto, and the mixture was allowed to stand at room temperature for 15 minutes to form a DNA-liposome complex. Each of the reaction solutions was added dropwise to the above COS-7 cell and thoroughly mixed, followed by culturing at 37° C. After the culturing for 72 hours, the culture supernatants were recovered and the activity of the anti-CCR4 CDR-grafted antibody activity in the culture supernatants was evaluated.

(2) Reactivity Evaluation of anti-CCR4 CDR-grafted Antibody for Human CCR4

The activity of the resulting culture supernatants of 22 antibodies was evaluated as follows.

Compound1 (SEQ ID NO:37) was selected as a human CCR4 extracellular region peptide which can react with the anti-CCR4 chimeric antibody KM2760 produced by the transformant KM2760 (FERM BP-7054) prepared in Reference Example 2. In order to use Compound1 in the activity measurement by ELISA, its conjugate with BSA (bovine serum albumin) (manufactured by NakalaW Tesque) was prepared and used as the antigen. That is, 100 ml of 25 mg/ml SMCC (4-(N-maleimidomethyl)cyclohexane-1 -carboxylic acid N-hydroxysuccinimide ester) (manufactured by Sigma)-DMSO solution was added dropwise to 900 ml of PBS solution containing 10 mg BSA under vortex and gently stirred for 30 minutes. To a gel filtration column, such as NAP-10 column or the like, equilibrated with 25 ml of PBS, 1 ml of the reaction solution was applied, and the eluate eluted with 1.5 ml of PBS was used as a BSA-SMCC solution (BSA concentration was calculated by $A_{280}$ measurement). Next, 250 ml of PBS was added to 0.5 mg of Compound 1 which was then completely dissolved by adding 250 ml of DMF, and then the above BSA-SMCC solution (BSA content:1.25 mg) was added under vortex and gently stirred for 3 hours. The reaction solution was dialyzed overnight at 4° C. against PBS, sodium azide was added thereto to give a final concentration of 0.05% and then the resulting mixture was filtered using a 0.22 mm filter to give a BSA-Compound1 solution.

Into a 96 well ELISA plate (manufactured by Greiner), 0.05 μg/ml of the prepared conjugate was dispensed in at 50 μl/well and allowed to stand at 4° C. overnight for adsorption. After washing with PBS, PBS containing 1% BSA (hereinafter referred to as "1% BSA-PBS") was added thereto at 100 μl/well and allowed to react at room temperature for 1 hour to block the remaining active groups. After washing each well with PBS containing 0.05% Tween 20 (hereinafter referred to as "Tween-PBS"), a culture supernatant of the transformant was added at 50 μl/well and allowed to react at room temperature for 1 hour. After the reaction and subsequent washing of each well with Tween-PBS, a peroxidase-labeled goat anti-human IgG(γ) antibody solution (manufactured by American Qualex) diluted 6,000 folds with 1% BSA-PBS was added as a secondary antibody solution in 50 μl/well portions and allowed to react at room temperature for 1 hour After the reaction and subsequent washing with Tween-PBS, an ABTS substrate solution (a solution prepared by dissolving 0.55 g of 2,2'-amino-bis(3-ethylbenzothiazoline-6-sulfonic acid) ammonium in 1 liter of 0.1 M citrate buffer (pH 4.2) and adding 1 μl/ml hydrogen peroxide just before use) was added at 50 μl/well to develop color, and the reaction was stopped 20 minutes thereafter by adding 5% SDS solution at 50 μl/well. Thereafter, absorbance at 415 nm was measured.

Also, in order to compare concentrations of a produced human IgG antibody in the culture supernatants, a goat anti-human IgG(γ) antibody (manufactured by American Qualex) diluted 2,000 folds with PBS was used as the antigen.

Figure 7:
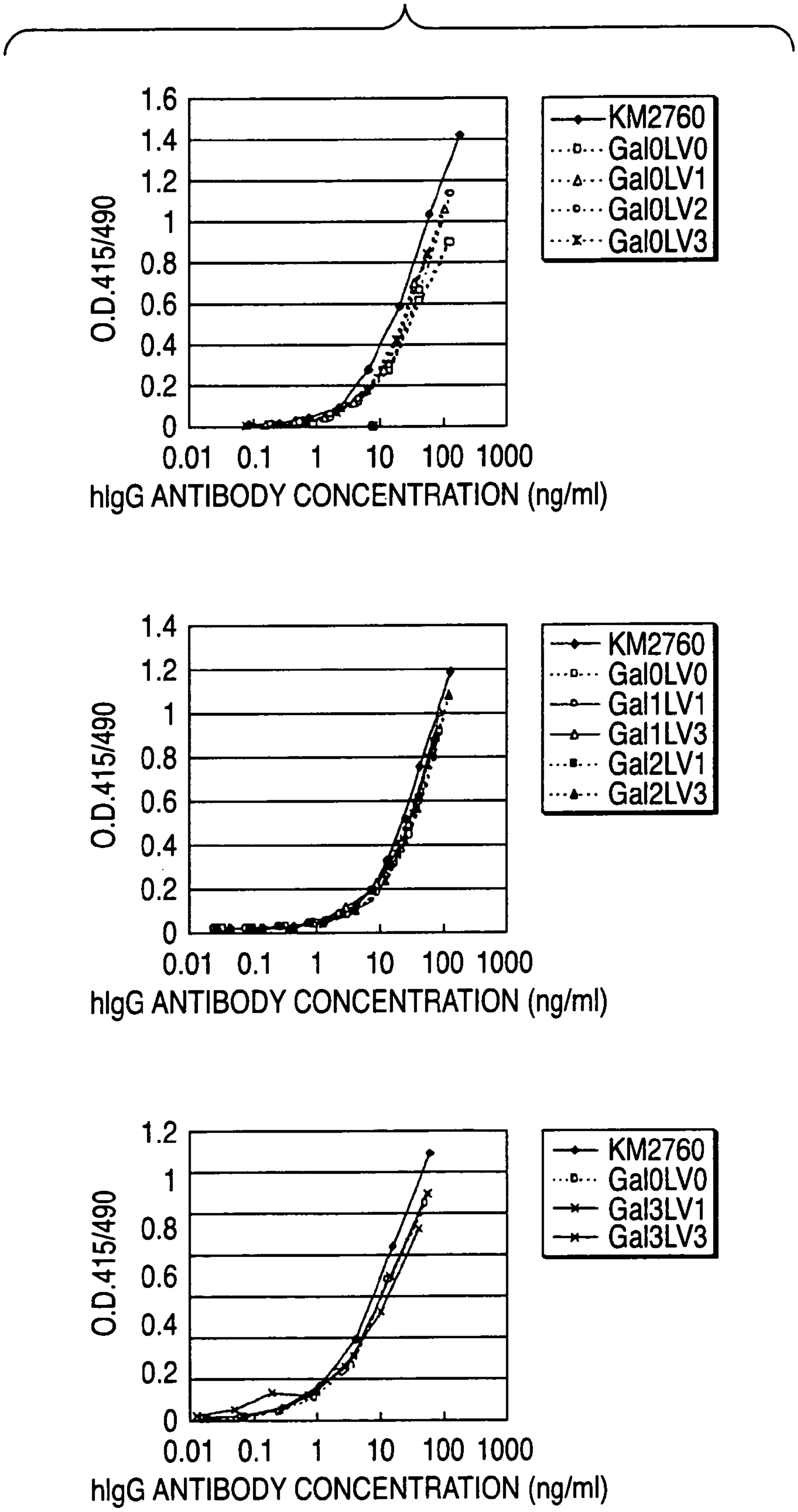
FIG. 7 shows reactivity of a culture supernatant obtained by transiently expressing an expression vector of each anti-CCR4 CDR-grafted antibody in COS-7 cell, with a CCR4 partial peptide according to ELISA.
Figure 8:
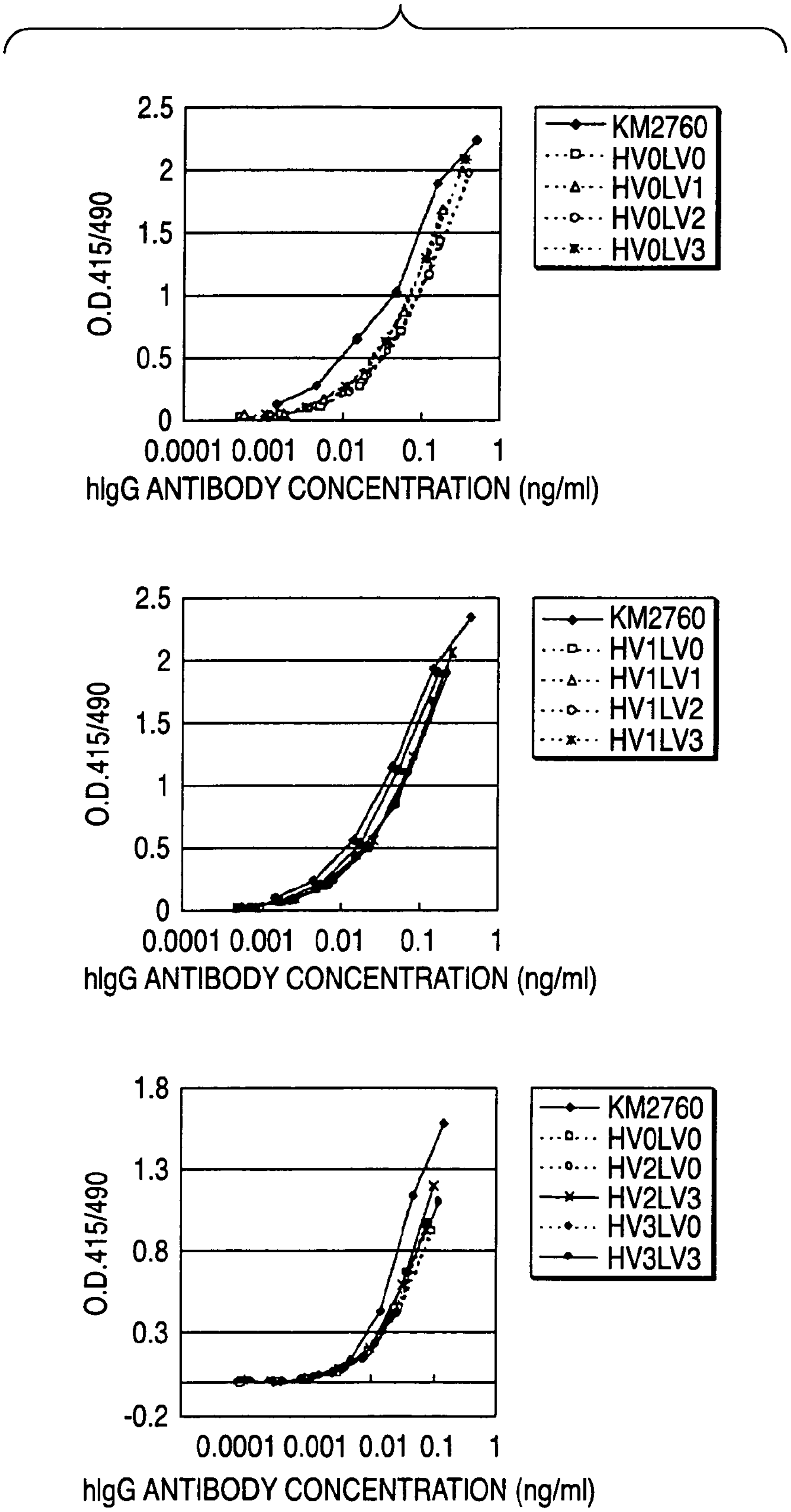
FIG. 8 shows reactivity of a culture supernatant obtained by transiently expressing an expression vector of each anti-CCR4 CDR-grafted antibody prepared by using other FRs in COS-7 cell, with CCR4 partial peptide according to ELISA.

The results are shown in FIG. 7 and FIG. 8. Each human CCR4 CDR-grafted antibody showed almost the same activity of the human chimeric antibody KM2760.

2. Stable Expression of Anti-CCR4 CDR-grafted Antibody using Animal Cells An anti-CCR4 CDR-grafted antibody was expressed in animal cells using the anti-CCR4 CDR-grafted antibody expression vector obtained in 2(3) of Example 1 as follows.

1) Stable Expression in Rat Myeloma Cell Line YB2/0 Cell (ATCC CRL 1581)

Each human CDR-grafted antibody expression plasmid was made into a linear state by digesting it with a restriction enzyme AatII (manufactured by TOYOBO), 10 μg of the digested product was introduced into $4\times10^6$ cells of the rat myeloma cell line YB2/0 cell (ATCC CRL 1581) by electroporation (*Cytotechnology,* 3, 133 (1990)), and then the cells were suspended in 40 ml of H-SFM (manufactured by GIBCO-BRL) medium (supplemented with 5% of fetal bovine serum (FBS)) and dispensed at 200 μl/well into a 96 well microtiter plate (manufactured by Sumitomo Bakelite). After culturing at 37° C. for 1 to 3 days in a 5% $CO_2$ incubator, G418 (manufactured by Nakalai Tesque) was added thereto to give a concentration of1 mg/ml and the culturing was continued for 1 to 2 weeks to obtain G418-resistant transformants.

Culture supernatants were recovered from wells in which colonies of the transformants showing G418 resistance became confluent, and antigen-binding activities of anti-CCR4 human CDR-grafted antibodies in the culture supernatants were measured by the ELISA shown in 1(2) of Example 2.

In order to increase the antibody expression amount using a dhfr gene amplification system, the transformants in wells in which expression of an anti-CCR4 chimeric antibody was found in the culture supernatants was suspended to give a density of1 to $2\times10^5$ cells/ml in H-SFM medium containing 1 mg/ml G418 and 50 nM methotrexate (hereinafter referred to as "MTX") which is an inhibitor of a dhfr gene product dihydrofolate reductase and dispensed in 1 ml portions into a 24 well plate (manufactured by Greiner) Transformants showing 50 nM MTX resistance were induced by culturing at 37° C. for 1 to 2 weeks in a 5% $CO_2$ incubator. When the transformants became confluent in the wells, antigen-binding activities of anti-CCR4 human CDR-grafted antibodies in the culture supernatants were measured by the ELISA shown in 1(2) of Example 2. Regarding transformants of wells where expression of anti-CCR4 human CDR-grafted antibodies was found in the culture supernatants, the MTX concentration was increased to 100 nM and then to 200 nM by the above method, and a transformant capable of growing in H-SFM medium containing 1 mg/ml G418 and 200 nM MTX and also capable of highly expressing the anti-CCR4 human CDR-grafted antibody was finally obtained. For the thus obtained transformant, single cell isolation (cloning) was carried out by limiting dilution analysis to obtain a transformant cell clone showing the highest expression of the anti-CCR4 human CDR-grafted antibody. An antibody producing cell KM8760 obtained by the gene transfer of an expression vector pKANTEX2160Gal1LV3 and an antibody producing cell KM8759 obtained by the gene transfer of an expression vector pKANTEX2160Gal2LV3 have been deposited on Jul. 30, 2002, as FERM BP-8130 and FERM BP-8129, respectively, in the International Depositary Authority at International Patent Organism Depositary, National Institute of Advanced Industrial Science and Technology (AIST Tsukuba Central 6, 1-1, Higashi 1-Chome Tsukuba-shi, Ibaraki-ken 305-8566 Japan).

(2) Purification of Anti-CCR4 CDR-grafted Antibody from Culture Supernatant

When a transformant showing G418 resistance appeared and became confluent, the medium was changed to 300 to 1,100 ml of H-SFM medium containing Daigo's GF21 (manufactured by Wako Pure Chemical Industries) at a concentration of 5%, followed by culturing for 3 to 5 days. When it became confluent, the culture supernatant was recovered. A purified protein was obtained by purifying the anti-CCR4 CDR-grafted antibody from about 300 to 1,100 ml of the culture supernatant using Prosep-A column (manufactured by Millipore) in accordance with the attached instructions.

3Activity Evaluation of Purified Anti-CCR4 CDR-grafted Antibody

The activity was evaluated using anti-CCR4 CDR-grafted antibodies derived from antibody-producing cells obtained by introducing expression vectors of Gal0LV0, Gal0LV1, Gal0LV3, Gal1LV1, Gal1LV3, Gal2LV1, Gal2LV3, Gal3LV1and Gal3LV3 into YB2/0 (hereinafter referred simply to as "Gal0LV0", "Gal0LV1", "Gal0LV3", "Gal1LV1", "Gal1LV3", "Gal2LV1", "Gal2LV3", "Gal3LV1"and "Gal3LV3", respectively).

(1) Measurement of Binding Activity of Anti-CCR4 CDR-grafted Antibody for Human CCR4 (ELISA Method)

Figure 9:
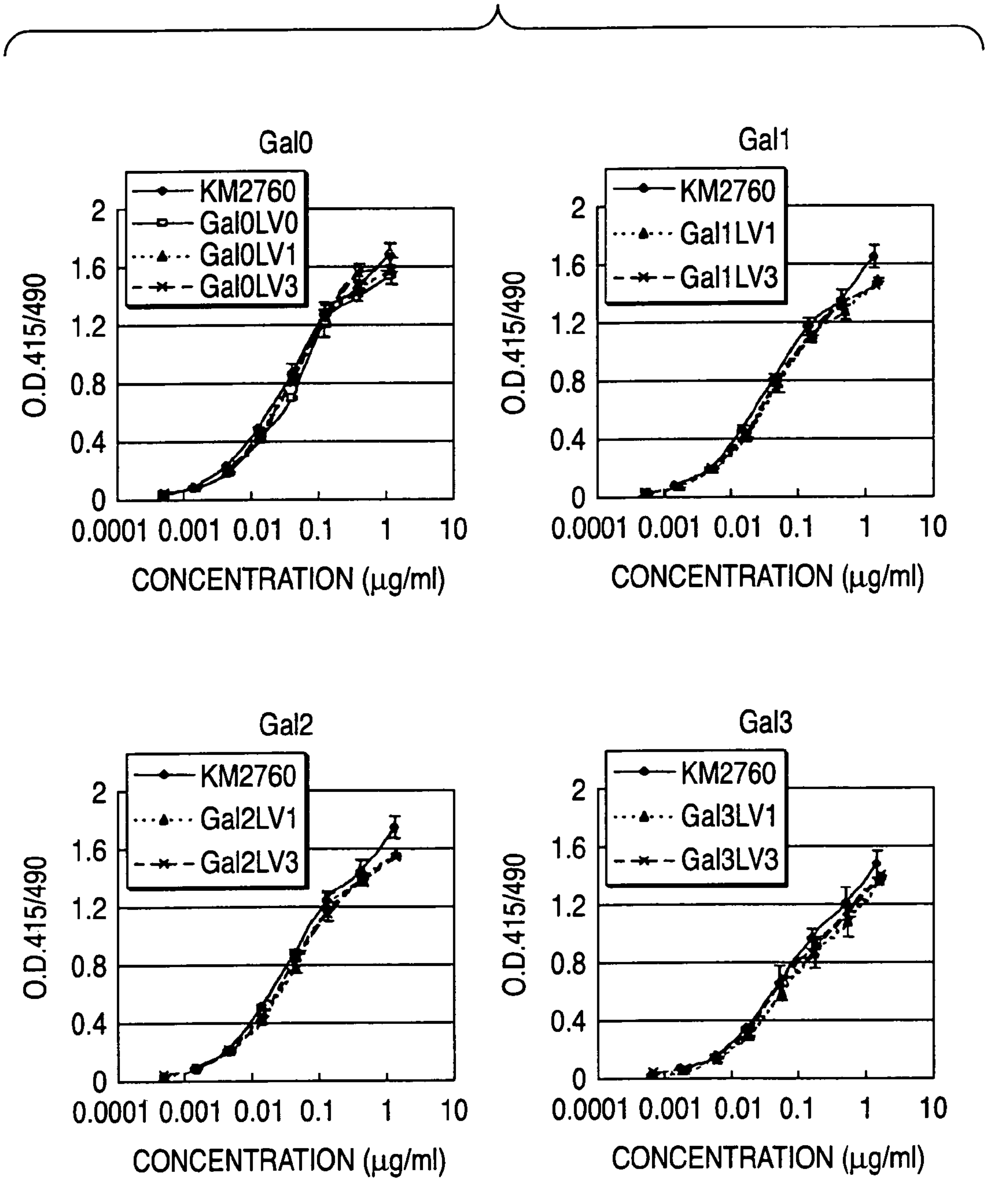
FIG. 9 shows reactivity of a purified anti-CCR4 CDR-grafted antibody with a CCR4 partial peptide.

The measurement was carried out in the same manner as the method described in the article 1(2) of Example 2. The results are shown in FIG. 9. Each anti-CCR4 CDR-grafted antibody showed almost the same activity of that of the human chimeric antibody KM2760.

(2) Reactivity of Anti-CCR4 CDR-grafted Antibody with Human CCR4-High-Expressing Cell (Fluorescent Antibody Technique)

Figure 10:
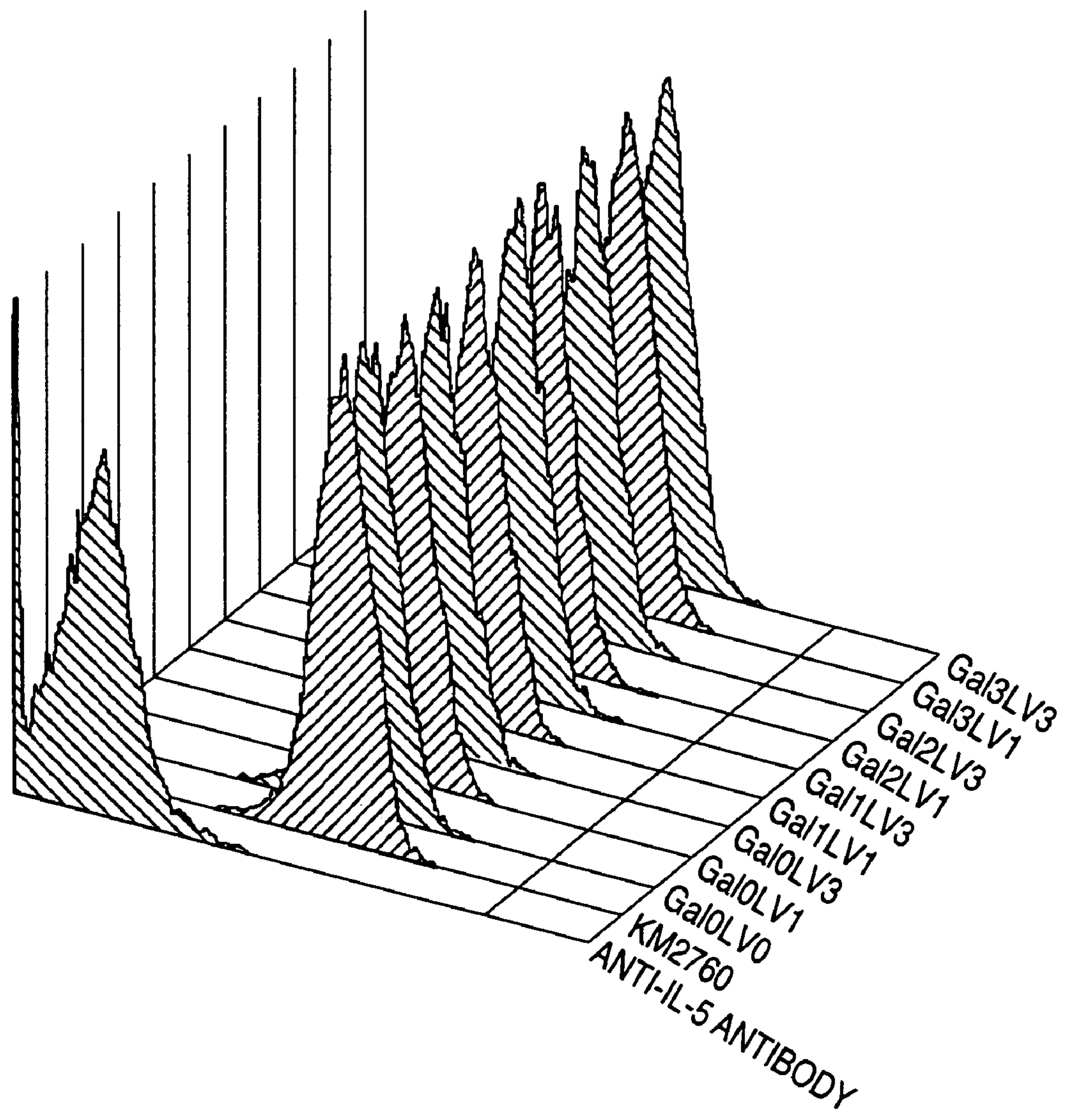
FIG. 10 shows reactivity of a purified anti-CCR4 CDR-grafed antibody with a CCR4 high expression cell (CCR4/EL-4)

Into a 96 well plate, $2\times10^5$ or more of CCR4/EL-4 cells, CCR4-high-expressing cells obtained in Reference Example 3, were dispensed. An antibody solution was prepared by diluting each of the purified antibodies and a human immunoglobulin (manufactured by Welfide) for preventing nonspecific staining to give concentrations of 10 μg/ml and 3.75 mg/ml, respectively, with a buffer for FACS, and the antibody solution was added at 100 μl/well and allowed to react for 30 minutes in ice. As a negative control, 10 μg/ml of an anti-human IL-5 receptor a chain antibody (WO 97/10354) was used. After washing twice with 200 μl/well of the buffer for FACS, a PE-labeled anti-human IgG antibody (manufactured by Coulter) diluted 100 times was added at 50 μl/well. After the reaction in ice under shading and subsequent washing three times with 200 μl/well of the buffer for FACS, the reaction product was suspended in 500 μl of the buffer for FACS and the fluorescence intensity was measured using a flow cytometer. The results are shown in FIG. 10. All of the anti-CCR4 CDR-grafted antibodies showed almost the same activity as the human chimeric antibody KM2760.

(3) Measurement of Activity of Anti-CCR4 CDR-grafted Antibody to Bind to Human CCR4 (BIAcore Method)

In order to measure the binding activity in more detail, the binding activity of various purified antibodies was measured using BIAcore 2000 (manufactured by BIACORE) as follows. In this case, HBS-EP (manufactured by BIACORE) was used as the buffer for diluting samples and for the measurement. First, 5 μl of 0.05 μg/ml solution of Compound 1 as a biotinylated CCR4 partial peptide was added to a sensor tip SA (manufactured by BIACORE) at a flow rate of 5 μl/minute and immobilized on the sensor tip.

To the prepared biotinylated compound 1 -immobilized sensor tip, 20 μl of 4 μg/ml solution of each of the purified antibodies was added at a flow rate of 5 μl/minute, and after completion of the addition, the dissociation reaction was monitored for 4 minutes and then the sensor tip surface was regenerated by adding 5 μl of 10 mM HCl twice. In this way, a binding reaction curve (sensorgram) for Compound 1 was obtained.

Figure 11:
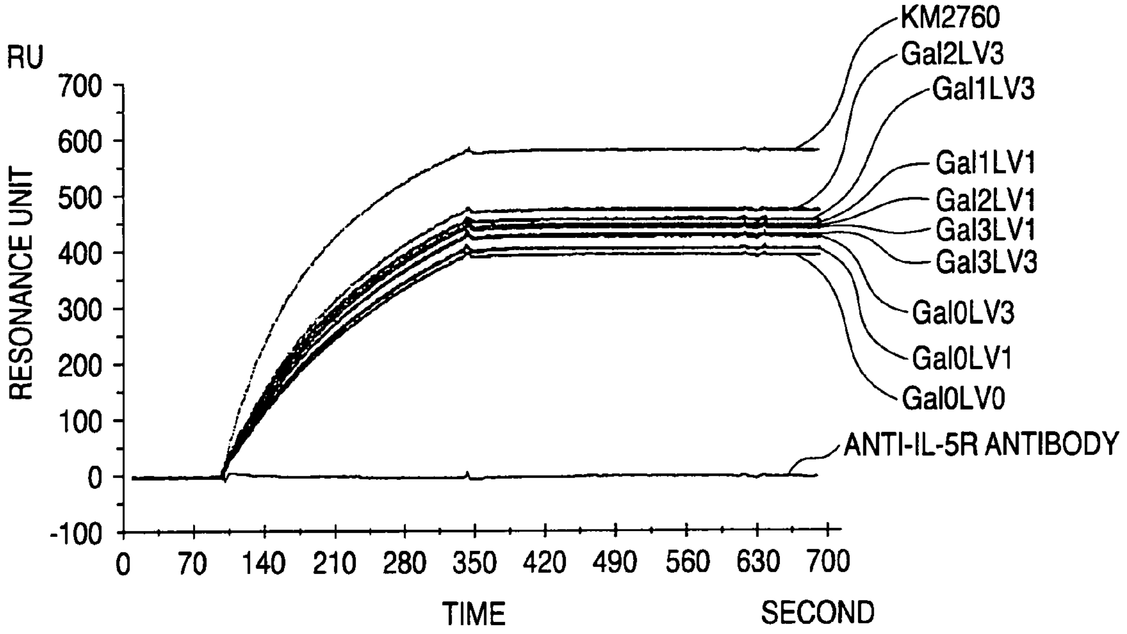
FIG. 11 shows affinity of a purified anti-CCR4 CDR-grafted antibody with a CCR4 partial peptide measured using a surface plasmon resonance sensor.

The results are shown in FIG. 11. The ordinate represents a resonance unit (RU) which means a mass change on the sensor tip For example, 1,000 RU corresponds to a mass change of about 1 $\mu g/mm^2$ protein. It was shown that KM 2760 has a markedly stable and high binding activity, because it showed a time-dependent binding activity for Compound 1 and dissociation of its binding was hardly found by the dissociation reaction. On the other hand, each of the anti-CCR4 CDR-grafted antibodies showed almost the same dissociation reaction as the human chimeric antibody KM2760, but a slight decrease in the activity was found in the binding reaction to the CCR4 partial peptide, Compound 1. The anti-CCR4 CDR-grafted antibody Gal0LV0 in which CDR alone was grafted showed the lowest binding activity, and the binding activity was increased by the amino acid residue modification of FR. The results show that an anti-CCR4 CDR-grafted antibody which maintains the antigen binding activity and binding specificity of a mouse antibody can be prepared by grafting CDR of the mouse antibody KM2160 to an appropriate human antibody FR, and that an anti-CCR4 CDR-grafted antibody having higher binding activity can be prepared by identifying FR amino acid residues important for the binding activity based on the three-dimensional structure and the like of antibody V regions and grafting them together with the CDR. It is expected that the anti-CCR4 CDR-grafted antibodies prepared in this Example have high binding activity to CCR4, have decreased immunogenicity in human in comparison with that of mouse antibodies and also that human chimeric antibodies, and have high safety and high therapeutic effects 2 In Vitro Cytotoxic Activity of Anti-CCR4 CDR-grafted Antibody (ADCC Activity)

In order to evaluate in vitro cytotoxic activity of the purified anti-CCR4 CDR-grafted antibody obtained in 2(2) of Example 2, its ADCC activity was measured as follows.

(1) Preparation of Target Cell Suspension

The human CCR4-high-expressing cell CCR4/EL-4 obtained in Reference Example 3 was cultured in 10% FCS-containing RPMI 1640 medium (manufactured by GIBCO) containing 0.5 mg/ml G418 to give a density of $1\times10^6$ cells/0.5 ml, 1.85 MBq equivalent of radioactive sodium chromate ($Na_2{}^{51}CrO_4$) (manufactured by Daiichi Pure Chemicals) was added thereto and the mixture was allowed to react at 37° C. for 1.5 hours to isotope-label the cells. After the reaction, the cells were washed three times by their suspension in RPMI 1640 medium and centrifugation, re-suspended in the medium and then incubated in ice at 4° C. for 30 minutes to spontaneously release the radioactive substance. After centrifugation, 5 ml of 10% FCS-containing RPMI 1640 medium was added thereto to give a density of $2\times10^5$ cells/ml as the target cell suspension.

(2) Preparation of Effector Cell Suspension

Healthy human peripheral blood (60 ml) was collected using a syringe containing 200 units (200 μl) of a heparin sodium injection (manufactured by Takeda Pharmaceutical). The entire amount was filled up to 120 ml by diluting it two folds with the same volume of physiological saline (manufactured by Otsuka Pharmaceutical). Lymphoprep (manufactured by NYCOMED) was dispensed at 5 ml into 12 tubes of 15 ml capacity centrifugation tubes (manufactured by Sumitomo Bakelite), the diluted peripheral blood was over-layered thereon at 10 ml, and the mixture was centrifuged at 800×g for 20 minutes at room temperature PBMC fractions between the blood plasma layer and the Lymphoprep layer were collected from all centrifugation tubes, suspended in 1% FCS-containing RPMI 1640 medium (hereinafter referred to as "1% FCS-RPMI"), washed twice by centrifugation at 400×g and 4° C. for 5 minutes and then re-suspended to give a density of $5\times10^6$ cells/ml to be used as the effector cells (3) Measurement of ADCC Activity The target cell suspension prepared in (1) was dispensed at 50 μl ($1\times10^4$ cells/well) into wells of a 96 well U bottom plate (manufactured by Falcon). Next, the effector cell suspension prepared in (2) was dispensed at 100 μl ($5\times10^5$ cells/well, the ratio of effector cells to target cells becomes 50: 1). Next, each anti-CCR4 chimeric antibody was added to give a final concentration of 0.1 ng/ml to 10 μg/ml and the mixture was allowed to react at 37° C. for 4 hours. After the reaction, the plate was centnfilged and the amount of $^{51}Cr$ in 100 μl of the supernatant in each well was measured by a γ-counter. The amount of the spontaneously dissociated $^{51}Cr$ was calculated in the same manner as the above using the medium alone instead of the effector cell suspension and antibody solution and measuring the amount of $^{51}Cr$ in the supernatant. The amount of the total dissociated $^{51}Cr$ was calculated in the same manner as the above by adding the medium alone instead of the antibody solution, and 1 N hydrochloric acid instead of the effector cell suspension, and measuring the amount of $^{51}Cr$ in the supernatant. The ADCC activity was calculated by the following equation:

$$ADCC\ \text{activity}\ (\%) = \frac{(\text{amount of } ^{51}\text{Cr in sample supernatant}) - (\text{amount of spontaneously released } ^{51}\text{Cr})}{(\text{amount of total } ^{51}\text{Cr}) - (\text{amount of spontaneously released } ^{51}\text{Cr})} \times 100$$

Figure 12:
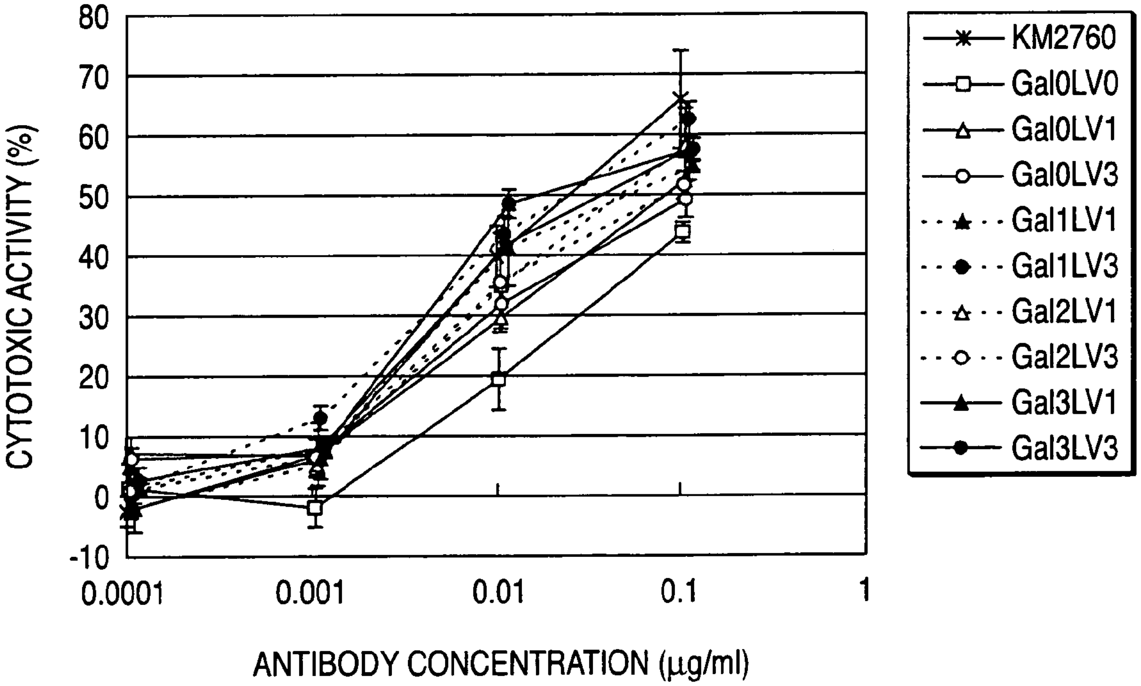
FIG. 12 shows cytotoxicity according to ADCC activity against CCR4/EL-4 cell.

The results are shown in FIG. 12. As shown in FIG. 12, the anti-CCR4 CDR-grafted antibody had strong cytotoxic activity antibody-concentration-dependently.

5. Effect of Inhibiting Production of Cytokine from Human PBMC

An effect of inhibiting cytokine production was examined using an anti-CCR4 CDR-grafted antibody Gal1LV3 and a chimeric antibody KM2760. An anti-IL-5R antibody was used as a negative control.

Figure 13:
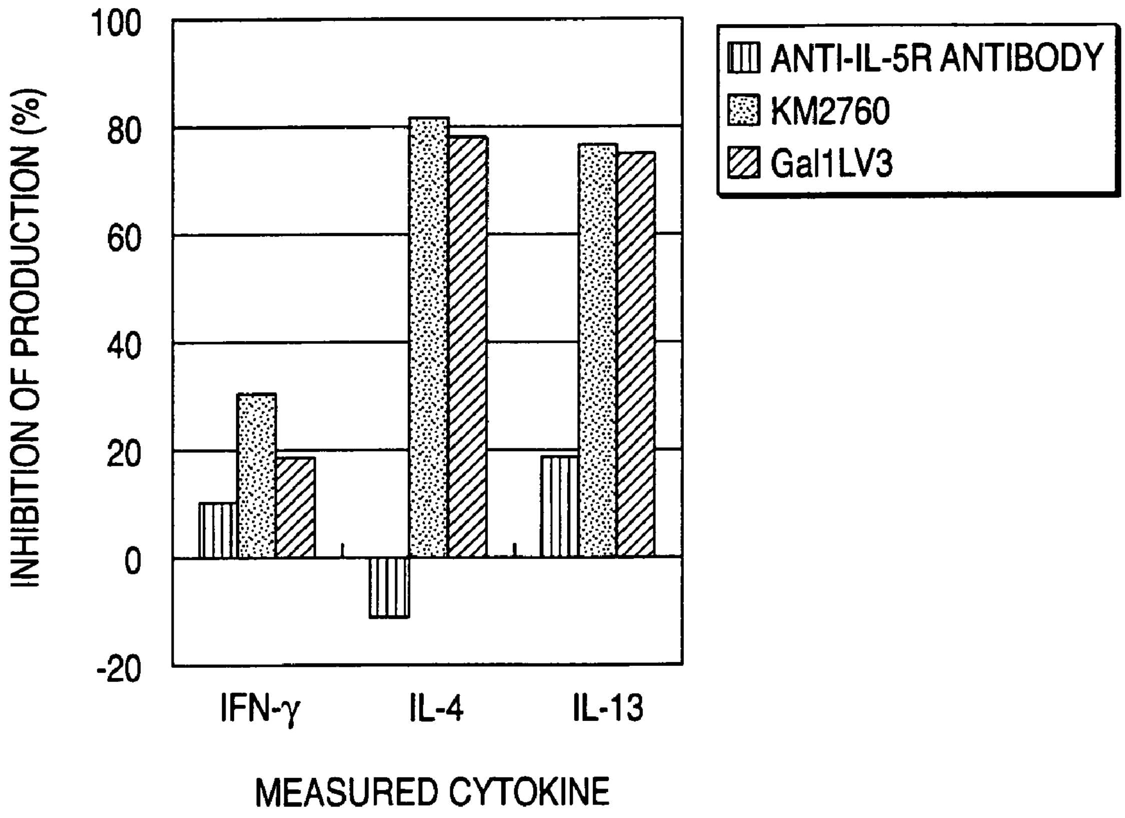
FIG. 13 shows effect on inhibition of production of IL-4, IL-13 and IFN-γ from human PBMC.

PBMC was separated in the same manner as in 4(2) of Example 2 and dispensed at $1\times10^6$ cells/well into a 96 well U-bottom plate, an evaluation antibody was added thereto to give a final concentration of 1 μg/ml, and the total volume was adjusted to 200 μl/well. The ADCC activity was induced by co-culturing at 37° C. for 24 hours in a stream of 5% $CO_2$. After the culturing, 100 μl of the supernatant was removed, 100 μl of a medium containing 100 ng/ml PMA (phorbol myristate acetate) and 2 μg/ml ionomycin (manufactured by SIGMA) was added thereto to give final concentrations of 50 ng/ml PMA and1 μg/ml ionomycin, and the cells were stimulated to induce the cytokine production. After introduction of each stimulant, culturing was carried out for 24 hours, culture supernatants were recovered and IL-4, IL-13 and interferon (IFN)-γ were measured using a cytokine assay kit (manufactured by Biosource). The production inhibition ratio was calculated by defining each cytokine production in the absence of antibody as 0% inhibition ratio, and the results are shown in FIG. 13. As shown in FIG. 13, similar to the chimeric antibody KM2760, the anti-CCR4 CDR-grafted antibody Gal1LV3-added group significantly inhibited production of the Th2 cytokine IL-4 and IL-13 but had little influence on the Th1 cytokine IFN-γ.

The results show that each anti-CCR4 CDR-grafted antibody can deplete or eliminate CCR4-expressed Th2 cells by activating human effector cells efficiently and, as a result, has an effect of inhibiting production of Th2 cytokine from the Th2 cells and therefore is useful in diagnosing or treating human Th2-mediated immune diseases such as bronchial asthma, atopic dermatitis and the like.

6. Analysis of Reactivity for Human Platelet (1) Separation of Human Platelet

A 1/10 volume of 3.2% sodium citrate was added to a blood sample collected from a healthy parson and thoroughly mixed. The blood was dispensed at 5 ml into 15 ml capacity tubes (manufactured by Greiner) and centrifuged at 90×g for 10 minutes at room temperature. The supernatants were collected and further centrifuged at 1,950×g for 10 minutes at room temperature. After discarding the supernatant, the pellets were suspended in the buffer for FACS and centrifuged at 1,190×g for 5 minutes at room temperature to wash the pellets. The pellets were again suspended in the buffer for FACS and centrifuged in the same manner, and then platelets in the pellet form were adjusted to give a density of about $1\times10^7$ pellets/ml using the buffer for FACS.

(2) Staining of Platelet

Each of the purified anti-CCR4 human CDR-grafted antibodies obtained in 3 in Example 2 was added to 100 μl of the platelet suspension obtained in the item 6(1) to give a concentration of 10 μg/100 μl and allowed to react at room temperature for 30 minutes in the dark. As comparative controls, each of an anti-CCR4 human chimeric antibody KM2760 and an anti-mouse antibody 1G1 antibody (manufactured by Pharmingen) was allowed to react with 100 ml of the platelet suspension at the same concentration After the reaction, 2 ml of the buffer for FACS was added to each of 15 ml capacity tubes, and the mixture was stirred and then washed by centrifugation at 840×g for 5 minutes at 4° C. After discarding the supernatant, the same operation was carried out again. A PE-labeled anti-mouse IgG antibody (manufactured by Coulter) diluted 50 folds with the buffer for FACS was added at 20 μl the tube containing a sample reacted with each of the human CDR-grafted antibodies and KM2760 and allowed to react at room temperature for 30 minutes in the dark. Regarding the tube containing the sample reacted with the 1G1 antibody, 20 μl of a 50 times-diluted PE-labeled anti-mouse IgG antibody (manufactured by DAKO) was further added and allowed to react at room temperature for 30 minutes in the dark.

After the reaction, 2 ml of the buffer for FACS was added to each tube, followed by stirring, and the mixture was washed by centrifugation at 840×g for 5 minutes at 4° C. After discarding the supernatant, the same operation was carried out again. After suspending the residue in 500 μl of the buffer for FACS, the fluorescence intensity was measured using a flow cytometer EPICS XL-MCL (manufactured by Beckman Coulter).

Figure 14:
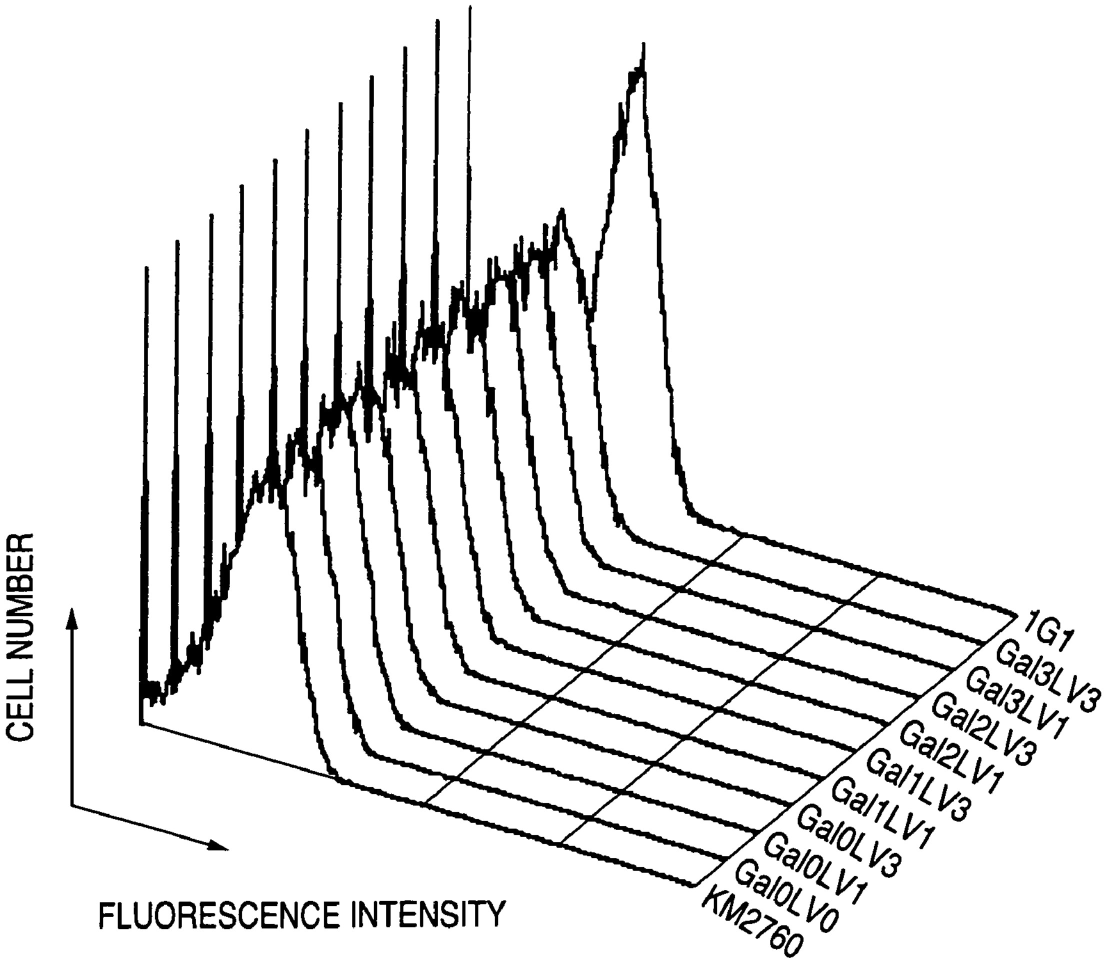
FIG. 14 shows binding activity of each antibody to a human platelet.

The results are shown in FIG. 14. The 1G1 antibody as a comparative control showed reactivity with platelets, but all of the anti-CCR4 human CDR-grafted antibodies did not show specific reactivity with human platelets similar to the anti-CCR4 human chimeric antibody KM2760.

REFERENCE EXAMPLE 1

Preparation of hybridoma cell which produces mouse anti-CCR4 monoclonal antibody:

Hybridoma cells which produce mouse anti-CCR4 monoclonal antibody KM2160 (*Int. Immunol*., 11, 81 (1999)) were produced according to the following procedure.

(1) Preparation of Antigen

The amino acid sequence (SEQ ID NO:48) of human CCR4 (hereinafter referred to as "hCCR4") protein was analyzed by using Genetyx Mac, and Compound 2 (SEQ ID NO:36) was selected as a partial sequence considered to be appropriate as the antigen among parts having high hydrophilicity, N-terminal and C-terminal.

(2) Preparation of Immunogen

The hCCR4 partial peptide obtained in (1) of Reference Example 1 was used as the immunogen after preparing its conjugate with KLH (Calbiochem) by the following method in order to increase its immunogenicity. Specifically, KLH was dissolved in PBS to give a concentration of 10 mg/ml, 1/10 volume of 25 mg/ml MBS (manufactured by Nakalai Tesque) was added dropwise thereto, and the mixture was allowed to react by stirring for 30 minutes. Free MBS was removed by a gel filtration column such as Sephadex G-25 column which had been equilibrated in advance with PBS or the like, and 2.5 mg of the resulting KLH-MB was mixed with1 mg of the peptide dissolved in 0.1 M sodium phosphate buffer (pH 7.0), followed by stirring at room temperature for 3 hours After the reaction, the mixture was dialyzed against PBS.

(3) Immunization of Animal and Production of Antibody-producing Cells

To 5-weeks-old female mice (Balb/c), 100 μg of the peptide-KLH conjugate prepared in (2) of Reference Example1 was administered together with 2 mg of aluminum gel and $1\times10^9$ cells of pertussis vaccine (manufactured by Chiba Serum Institute), and 2 weeks thereafter, 100 μg of the conjugate was administered once a week at a total of 4 times. A blood sample was taken from each animal from the venous plexus of the fundus of the eye, its serum titer was examined by an enzyme immunoassay described below, and the spleen was excised 3 days after the final immunization from a mouse which showed a sufficient antibody titer. The spleen was excised from a mouse on the 3rd day after the final administration and cut to pieces in MEM (manufactured by Nissui Pharmaceutical), and cells were unbound using a pair of forceps and centrifuged (1,200 rpm, 5 minutes), the supernatant was removed, followed by treatment with 3 ml of a Tris-ammonium chloride buffer (pH 7,65) for 1 to 2 minutes to eliminate erythrocytes. The remaining cells were further washed three times with MEM and used for cell fusion.

(4) Preparation of Mouse Myeloma Cell

An 8-azaguanine-resistant mouse myeloma cell line, P3X63Ag8U. 1 (ATCC CRL-1597, hereinafter referred to as "P3-U 1"), was cultured and used as the parent line in cell fusion.

(5) Preparation of Hybridoma Cell

The spleen cells and myeloma cells obtained in (3) and (4) in Reference Example1 were mixed to a ratio of 10:1, followed by centrifuging (1,200 rpm, 5 minutes) to remove the supernatant, 0.5 ml of a polyethylene glycol solution (a solution containing 2 g of polyethylene glycol-1000, 2 ml of MEM and 0.7 ml of DMSO) was added to the thus precipitated cells per $10^8$ of spleen cells at 37° C., followed by thoroughly suspending Thereafter, 1 to 2 ml of MEM was added several times at 1 to 2 minute intervals, and the final volume was adjusted to 50 ml with MEM. After removing the supernatant by centrifugation (900 rpm, 5 minutes), the precipitate was suspended in 100 ml of HAT medium, dispensed in 100 μl/well into a 96 well microtiter plate (manufactured by Sumitomo Bakelite), followed by culturing in a 5% $CO_2$ incubator at 37° C. for 10 to 14 days. Using wells in which propagation of the fused cell was observed, binding activity to the hCCR4 partial peptide (Compound 2) in the culture supernatant was measured by ELISA (*Antibodies: A Laboratory Manual*, Cold Spring Harbor Laboratory, Chapter 14 (1988), *Monoclonal Antibodies: Principles and Practice*, Academic Press Limited (1966), etc.). Each well in which the activity was confirmed was cloned by a total of 2 times of limiting dilution, once by changing the medium to the HT medium and then changing the medium to the normal medium, In this way, a hybridoma cell KM2160 which produces the mouse antibody KM2160 was obtained. KM2160 specifically reacted with the hCCR4 partial peptide (Compound 2).

REFERENCE EXAMPLE 2

Preparation of Anti-CCR4 Chimeric Antibody.

1. Isolation and Analysis of cDNA Encoding V Region of Anti-CCR4 mouse antibody:

(1) Preparation of mRNA from Hybridoma Cell which Produces Anti-CCR4 Mouse Antibody A mRNA was prepared from the hybridoma cell KM2160 described in Reference Example 1. About 48 μg of mRNA was prepared from $8\times10^7$ cells of the hybridoma cell KM2160 using a mRNA preparation kit, Fast Track mRNA Isolation Kit (manufactured by Invitrogen) according to the manufacture's instructions, (2) Preparation of H Chain and L Chain cDNA Library of Anti-CCR4 Mouse Antibody cDNA having EcoRI-NotI adapters on both termini was synthesized from 5 μg of the KM2160 mRNA obtained in 1(1) of Reference Example 2 using cDNA Synthesis kit (manufactured by Amersham Pharmacia Biotech) according to the manufacture's instructions, The thus prepared cDNA was dissolved in 20 μl of sterile water and fractionated by agarose gel electrophoresis, and about 1.5 kb cDNA fragments corresponding to the H chain of IgG type antibody and about 1.0 kb cDNA fragments corresponding to the L chain of K type were respectively recovered using QIAquick Gel Extraction Kit (manufactured by QIAGEN). Next, using γZAPII Predigested EcoRI/CIAP-Treated Vector Kit (manufactured by Stratagene), each of 0.1 μg of the about 1.5 kb cDNA fragments and 0.1 μg of the about 1.0 kb cDNA fragments was linked to 1 μg of the λZAPII vector which had been digested with a restriction enzyme EcoRI and terminus-dephosphorylated with Calf Intestine Alkaline Phosphatase according to the manufacture's instructions. Into λ phage, 2.5 μl of each reaction solution after the ligation was packaged using GigapackIII Gold Packaging Extract (manufactured by Stratagene) according to the manufacture's instructions, and then *Escherichia coli* XL1-Blue (*Biotechniques*, 5, 376 (1987)) was infected with an appropriate amount of the phage to obtain $9.3\times10^4$ of phage clones as the H chain cDNA library of KM2160 and $7.4\times10^4$ of phage clones as the L chain cDNA library Thereafter, each phage was fixed on a nylon membrane filter Hybond-N+ (manufactured by Amersham Pharmacia Biotech) according to the manufacture's instructions.

(3) Cloning of H Chain and L Chain cDNAs of Anti-CCR4 Mouse Antibody

Using ECL Direct Nucleic Acid Labeling and Detection System (manufactured by Arnershani Pharrnacia Biotech), according to the manufacture's instructions, clones on the nylon membrane filters of the KM2160 H chain cDNA library and L chain cDNA library prepared in 1(2) of Reference Example 2 were detected using cDNA of the C region of a mouse antibody (H chain is a BamHI-EcoRI fragment of mouse Cγ1 cDNA (*EMBO J.*, 3, 2047 (1984)), L chain is a Hpal-EcoRI fragment of CK cDNA (*Cell*, 22, 197 (1980)) as the probe, and phage clones strongly bound to the probe were obtained as 10 clones for each of the H chain and the L chain. Next, each phage clone was converted into plasmid by the in vivo excision method using )λZAPII Cloning Kit according to the manufacture's instructions (manufactured by Stratagene). Using BigDye Terminator Cycle Sequencing FS Ready Reaction Kit (manufactured by PE Biosystems), the nucleotide sequence of cDNA contained in each plasmid obtained in this manner was analyzed by a DNA sequencer ABI PRISM 377 of the same manufacturer according to the manufacture's instructions. As a result, a plasmid pKM2160H4 containing a full length functional H chain cDNA and a plasmid pKM2160L6 containing a full length L chain cDNA, in which an ATG sequence considered to be the initiation codon is present in the 5'-terminal of cDNA, were obtained.

(4) Analysis of Amino Acid Sequence of V Region of Anti-CCR4 Mouse Antibody

A full nucleotide sequence of the H chain V region contained in the plasmid pKM2160H4, a full amino acid sequence of the H chain V region deduced therefrom, a full nucleotide sequence of the L chain V region contained in the plasmid pKM2160L6 and a full amino acid sequence of the L chain V region deduced therefrom are represented by SEQ ID NOs:61, 62, 63 and 64, respectively. Based on the comparison with sequence data of known mouse antibodies (*Sequences of Proteins of Immunological Interest*, US Dept Health and Human Services (1991)) and the comparison with the results of analysis of the H chain and L chain N-terminal amino acid sequences of the purified anti-CCR4 mouse antibody KM2160 carried out using a protein sequencer (PPSQ-10, manufactured by Shimadzu), it was found that each cDNA thus isolated is a fill length cDNA which encodes the anti-CCR4 mouse antibody KM2160 containing secretory signal sequences which are amino acids of positions 1-19 in the amino acid sequence represented by SEQ ID NO:15 in the H chain and amino acids of positions 1-19 in the amino acid sequence represented by SEQ ID NO:25 in the L chain.

Next, novelty of the amino acid sequences of the V regions of H chain and L chain of the anti-CCR4 mouse antibody KM2160 was examined. Using GCG Package (version 9.1, manufactured by Genetics Computer Group) as the sequence analyzing system, amino acid sequence data base of known proteins were searched by BLAST method (*Nucleic Acids Res*., 25, 3389 (1997)). As a result, completely coincided sequences were not found for both of the H chain and L chain, so that it was confirmed that the H chain V region and L chain V region of the anti-CCR4 mouse antibody KM2160 are novel amino acid sequences.

Also, CDRs of the H chain V region and L chain V region of the anti-CCR4 mouse antibody KM2160 were identified by comparing with amino acid sequences of known antibodies. Amino acid sequences of CDR1, CDR2 and CDR3 in the H chain V region of the anti-CCR4 mouse antibody KM2160 are represented by SEQ ID NOs:1, 2 and 3, respectively, and amino acid sequences of CDR1, CDR2 and CDR3 in the L chain Y region in SEQ ID NOs:.5, 6 and 7, respectively.

2. Stable Expression of Anti-CCR4 Chimeric Antibody using Animal Cell (1) Construction of Anti-CCR4 Chimeric Antibody Expression Vector pKANTEX2160

An anti-CCR4 chimeric antibody expression vector pKANTEX2160 was constructed as follows, using a humanized antibody expression vector pKANTEX93 which expresses a human IgG1 and k type antibody and the plasmids pKM2160H4 and pKM2160L6 obtained in 1(3) of Reference Example 2.

A synthetic DNA having the nucleotide sequences represented by SEQ ID NOs:65 and 66 was designed in order to obtain the H chain V region cDNA of KM2160 by PCR, and another synthetic DNA having the nucleotide sequences represented by SEQ ID NOs:67 and 68 for obtaining the L chain V region cDNA. Each synthetic DNA contains a restriction enzyme recognizing sequence in its 5'-terminal for its cloning into pKANTEX93, and synthesis of the DNA was entrusted to Genset Inc. The plasmid pKM2160H4 (20 ng) obtained in 1(3) of Reference Example 2 was added to a buffer containing 50 μl of PCR Buffer #1 attached to KOD DNA Polymerase (manufactured by TOYOBO), 0.2 mM dNTPs, 1 mM magnesium chloride and 0.5 μM of the synthetic DNA having the nucleotide sequences represented by SEQ ID NOs:11 and 12, and the mixture was heated at 94° C. for 3 minutes. After 2.5 units of KOD DNA Polymerase (manufactured by TOYOBO) were added, the mixture was subjected to 25 cycles of the reaction each cycle consisting of heating at 94° C. for 30 seconds, at 580C for 30 seconds and at 74° C. for 1 minute, using a DNA thermal cycler GeneAmp PCR System 9600 (manufactured by PERKIN ELMER). In the same manner, 20 ng of the plasmid pKM2160L6 obtained in 1(3) of Reference Example 2 was added to a buffer containing 50 μl of PCR Buffer #1 attached to KOD DNA Polymerase (manufactured by TOYOBO), 0.2 mM dNTPs,1 mM magnesium chloride and 0.5 μM of the synthetic DNA having the nucleotide sequences represented by SEQ ID NOs:67 and 68, and PCR was carried out in the same manner as described above, The reaction solution (10 μl) was subjected to agarose gel electrophoresis, and then an H chain V region PCR product of about 0.46 kb and an L chain V region PCR product of about 0.43 kb were each recovered using QIAquick Gel Extraction Kit (manufactured by QIAGEN).

Figure 15:
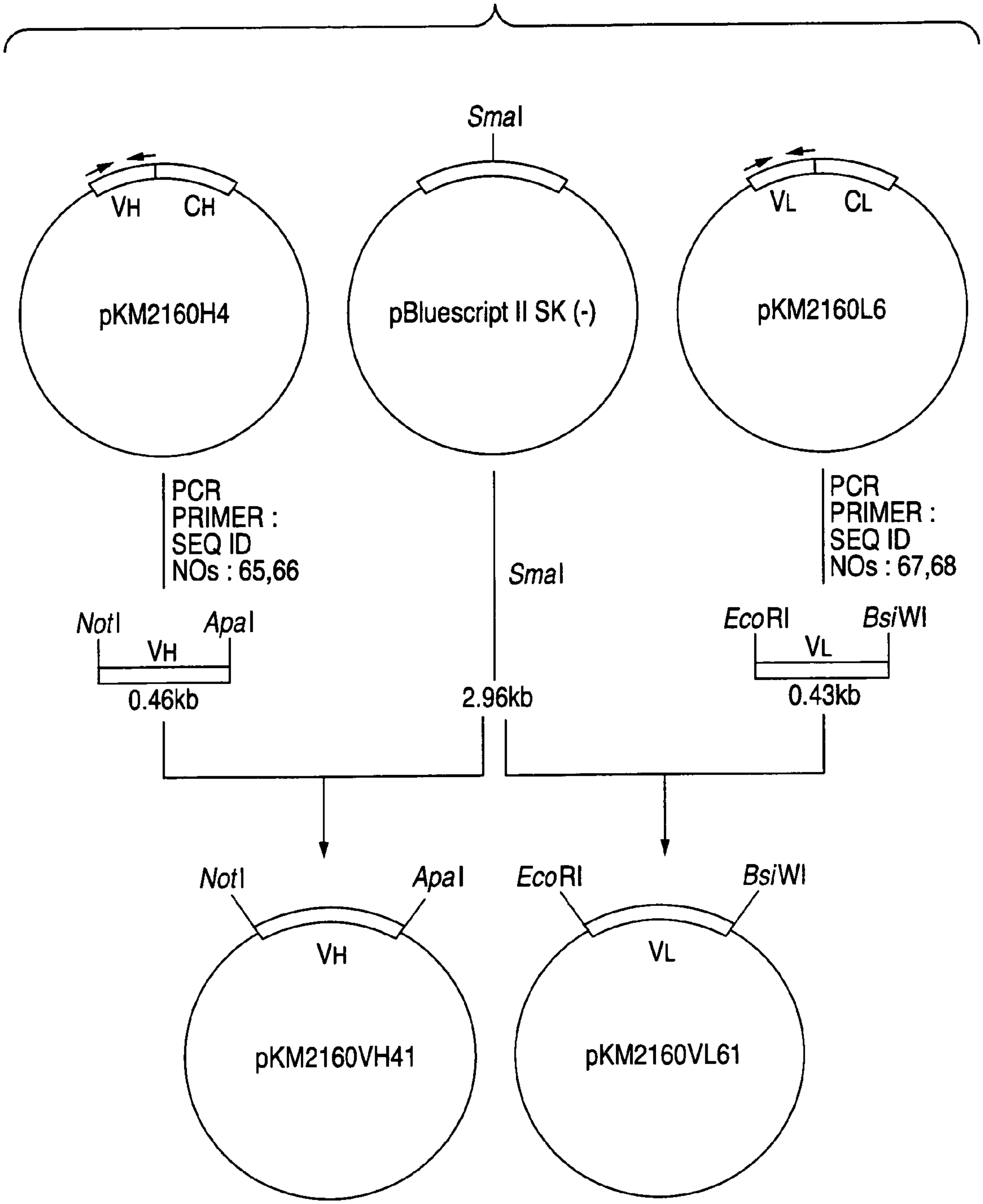
FIG. 15 shows construction steps of plasmids pKM2160VH41 and pKM2160VL61.

Next, 0.1 μg of DNA obtained by digesting a plasmid pBluescript SK(−) (manufactured by Stratagene) with a restriction enzyme SmaI (manufactured by Takara Shuzo) and about 0.1 μg of each of the PCR products obtained above were added to sterile water to give a final volume of 7.5 μl, and 7.5 μl of the solution I of TAKARA DNA Ligation Kit Ver. 2 (manufactured by Takara Shuzo) and 0.3 μl of a restriction enzyme SmaI were added thereto, and the mixture was allowed to react at 22° C. overnight. Using the resulting recombinant plasmid DNA solution, *E. coli* DH5α (manufactured by TOYOBO) was transformed. Each plasmid DNA was prepared from the transformant clones and subjected to the reaction using BigDye Terminator Cycle Sequencing FS Ready Reaction Kit (manufactured by PE Biosystems) according to the manufacture's instructions, and the nucleotide sequence was analyzed by a DNA sequencer ABI PRISM 377 of the same manufacturer. Thus, the plasmids pKM2160VH41 and pKM2160VL61 shown in FIG. 15 having the desired nucleotide sequences were obtained.

Figure 16:
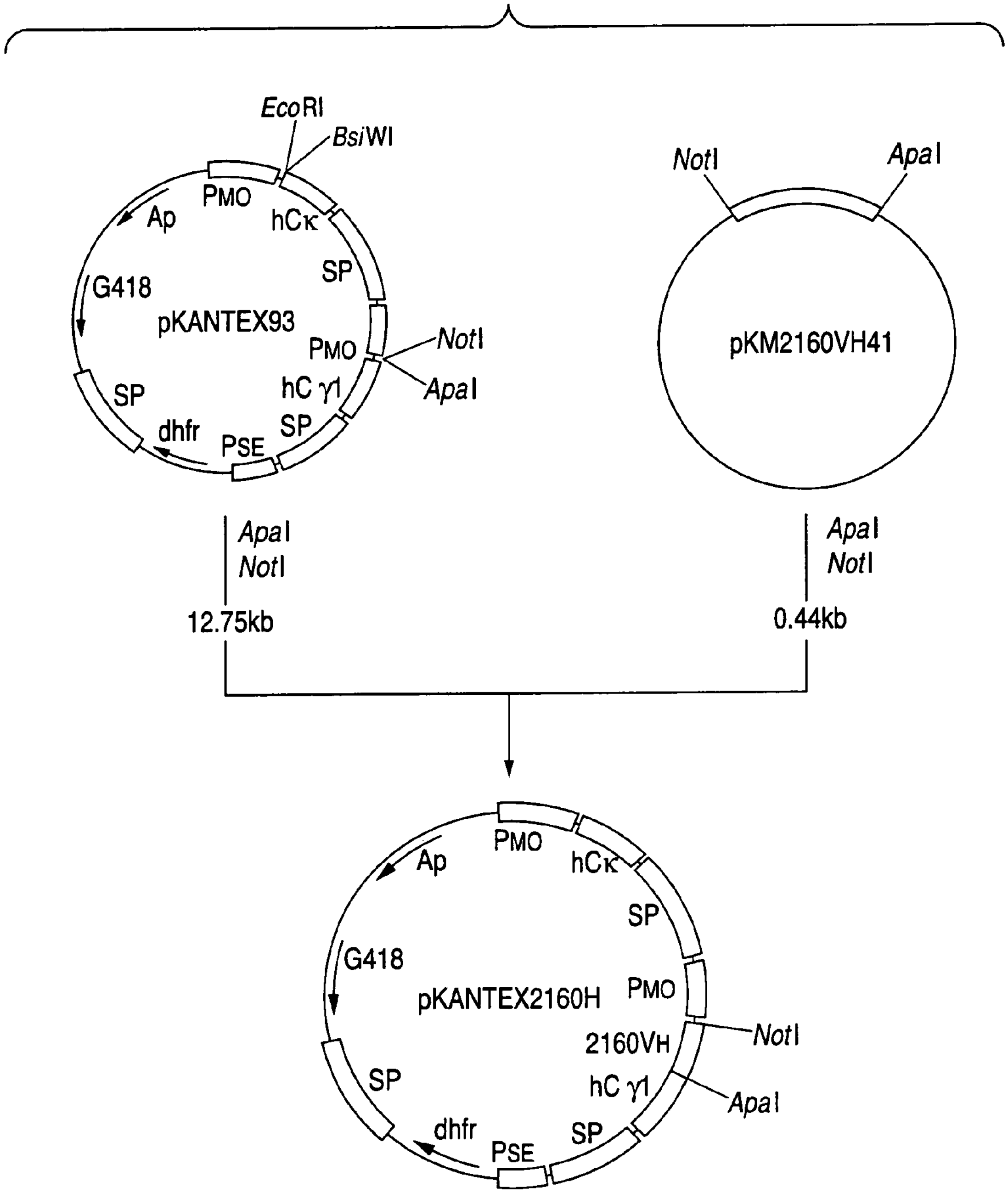
FIG. 16 shows construction step of a plasmid pKANTEX2160H.

Next, 3 μg of the humanized antibody expression vector pKANTEX93 and 3 μg of the pKM2160VH41 obtained above were added to a buffer containing 30 1 of 10 mM Tris-HCl (pH 7.5), 10 mM magnesium chloride and1 mM DFT, 10 units of a restriction enzyme ApaI (manufactured by Takara Shuzo) were added thereto, and the mixture was allowed to react at 37° C. for 1 hour. The reaction solution was subjected to ethanol precipitation, and the resulting precipitate was added to a buffer containing 10 μl of 50 mM Tris-HCl (pH 7.5), 100 mM sodium chloride, 10 mM magnesium chloride, 1 mM DTT, 100 μg/ml BSA and 0.01% Triton X-100, 10 units of a restriction enzyme NotI (manufactured by Takara Shuzo) were added thereto, and the mixture was allowed to react at $_{37}$° C. for 1 hour. The reaction mixture was fractionated by agarose gel electrophoresis, and about 12.75 kb and about 0.44 kb ApaI-NotI fragments of pKANTEX93 and pKM2160VH41, respectively, were recovered The thus obtained two fragments were linked using TAKARA DNA Ligation Kit Ver. 2 according to the manufacture's instructions, and *E. coli* DH5α (manufactured by TOYOBO) was transformed using the resulting recombinant plasmid DNA solution. Each plasmid DNA was prepared from the transformant clones and confirmed by a restriction enzyme treatment to thereby obtain a plasmid pKANTEX2160H shown in FIG. 16, in which about 0.44 kb of the desired ApaI-NotI fragment had been inserted.

Figure 17:
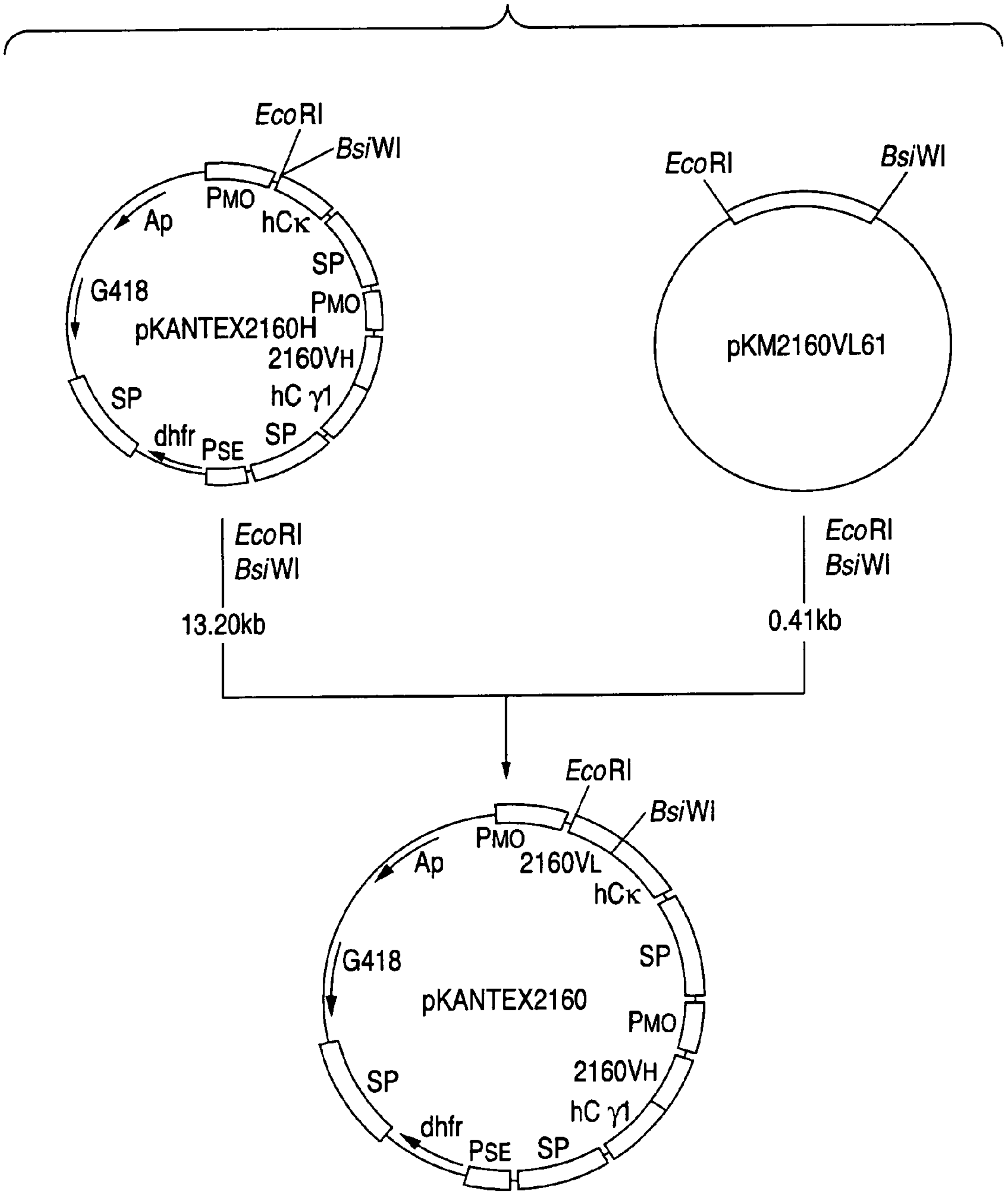
FIG. 17 shows construction step of a plasmid pKANTEX2160.

Next, 3 μg of the pKANTEX2160H and 3 μg of the pKM2160VL61 obtained above were added to a buffer containing 50 mM Tris-HCl (pH 7.5), 100 mM sodium chloride, 10 mM magnesium chloride, 1 mM DTT and 100 μμg/ml of BSA, the solution was adjusted to give a total volume of 30 μl, 10 units of a restriction enzyme BsiWI (manufactured by New England Biolabs) was added thereto, and the mixture was allowed to react at 55° C. for 1 hour. Then, a restriction enzyme EcoRI (manufactured by Takara Shuzo) was added thereto, and the mixture was allowed to react at 37° C. for 1 hour. The reaction mixture was fractionated by agarose gel electrophoresis, and about 13.20 kb and about 0.41 kb EcoRI-BsiWI fragments of pKANTEX2160H and pKM2160VL61, respectively, were recovered. The thus obtained two fragments were linked using TAKARA DNA Ligation Kit Ver. 2 according to the manufacture's instructions, and *E. coli* DH5α (manufactured by TOYOBO) was transformed using the resulting recombinant plasmid DNA solution. Each plasmid DNA was prepared from the transformant clones and confirmed by a restriction enzyme treatment to thereby obtain a plasmid pKANTEX2160 shown in FIG. 17, in which about 0.41 kb of the desired EcoRI-BsiWI fragment had been inserted. When the plasmid was subjected to the reaction using BigDye Terminator Cycle Sequencing FS Ready Reaction Kit (manufactured by PE Biosystems) according to the manufacture's instructions, and the nucleotide sequence was analyzed by a DNA sequencer ABI PRISM 377 of the same manufacturer, it was confirmed that the desired plasmid into which cDNA encoding the KM2160 H chain and L chain V regions had been cloned was obtained.

(2) Stable Expression of Anti-CCR4 Chimeric Antibody using Animal Cell

The anti-CCR4 chimeric antibody was expressed in animal cells as described below using the anti-CCR4 chimeric antibody expression vector pKANTEX2160 obtained in 2(1) of Reference Example 2

The plasmid pKANTEX2160 was converted into a linear form by digesting with a restriction enzyme AatII (manufactured by TOYOBO) and 10 μg thereof was introduced into $4\times10^6$ cells of rat myeloma cell line YB2/0 (ATCC CRL1662) by electroporation (*Cytotechnology*, 3, 133 (1990)), and the cells were suspended in 40 ml of H-SFM (manufactured by GIBCO-BRL) medium (supplemented with 5% FCS) and dispensed in 200 μl/well into a 96 well microtiter plate (manufactured by Sumitomo Bakelite). Twenty-four hours after incubation at 37° C. in a 5% $CO_2$ incubator, G418 was added to give a concentration of 1 mg/ml, followed by culturing for 1 to 2 weeks. A culture supernatant was recovered from a well in which a colony of G418-resistant transformant appeared and became confluent, and antigen-binding activity of the anti-CCR4 chimeric antibody in the supernatant was measured by ELISA shown in 2(3) of Reference Example 2 (a peroxidase-labeled goat anti-human IgG(γ) antibody was used as the secondary antibody).

In order to increase the expressed amount of the antibody using a dhfr gene amplification system, the transformant in a well where expression of the anti-CCR4 chimeric antibody was found in the culture supernatant was suspended to give a density of1 to $2\times10^5$ cells/ml in H-SFM medium containing 1 mg/ml G418 and 50 nM methotrexate (hereinafter referred to as "MTX": manufactured by Sigma) which is the inhibitor of a dhfr gene product dihydrofolate reductase, and the suspension was dispensed in1 ml into wells of a 24 well plate (manufactured by Greiner) The mixture was cultured at 37° C. for 1 to 2 weeks in a 5% $CO_2$ incubator, so that a transformant showing resistance to 50 nM MTX was induced. When the transformant became confluent in a well, antigen-binding activity of the anti-CCR4 chimeric antibody in the culture supernatant was measured by ELISA shown in 2(3) of Reference Example 2Regarding the transformants in wells where expression of the anti-CCR4 chimeric antibody was found in culture supernatants, the MTX concentration was increased to 100 nM and then to 200 nM in the same manner to finally obtain a transformant which can grow in H-SFM medium containing1 mg/ml of G418 and 200 nM of MTX and can also highly express the anti-CCR4 chimeric antibody. The thus obtained transformant was subjected to single cell isolation (cloning) by two times of limited dilution assay, and a transformant clone having the highest anti-CCR4 chimeric antibody expression was named KM2760. The expressed amount of the anti-CCR4 chimeric antibody by KM2760 was about 5 $\mu g/10^6$(*cells*24 hours. In addition, the antibody H chain C region of KM2760 belongs to human IgG1 subclass. KM2760 has been internationally deposited as FERM BP-7054 on Feb. 24, 2000, in National Institute of Bioscience and Human Technology, Agency of Industrial Science and Technology, the Ministry of International Trade and Industry (present name: International Patent Organism Depositary, National Institute of Advanced Industrial Science and Technology) (Higashi 1-1-3, Tsukuba-shi, Ibaraki Prefecture, Japan (present address: AIST Tsukuba Central 6, 1-1, Higashi 1-Chome Tsulcuba-shi, Ibaraki-ken 305-8566 Japan)).

REFERENCE EXAMPLE 3

Establishment of hCCR4-High-expressing Cell:

(1) Construction of Expression Vector CAG-pcDNA3 for Animal Cell

An expression vector was constructed as descried below by producing an expression vector (CAG-pcDNA3) in which the promoter region of an expression vector for animal cell, pcDNA3 (manufactured by FNVITROGEN), was changed from cytomegalovirus (CMV) promoter to CAG (AG (modified chicken β actin) promoter with CMV-IE enhancer), and inserting the CCR4 gene into the vector.

pcDNA3 (5 μg) was allowed to react with a restriction enzyme NruI (manufactured by Takara Shuzo) at 37° C. for 1 hour, and then DNA fragments were recovered by ethanol precipitation. Next, they were allowed to react with a restriction enzyme HindIII (manufactured by Takara Shuzo) at 37° C. for 1 hour and then fractionated by agarose gel electrophoresis to recover a DNA fragment of about 5.8 kb containing no CMV promoter region. Plasmid CAG-pBluescript IIKS(+) (3 μg) having CAG promoter (*Nuc. Acid Res.*, 23 3816 (1995)) region was allowed to react with a restriction enzyme SalI (manufactured by Takara Shuzo) at 37° C. for 1 hour and then DNA fragments were recovered by ethanol precipitation. They were blunt-ended with DNA Blunting Kit (manufactured by Takara Shuzo), further allowed to react with HindIII at 37° C. for 1 hour, and then fractionated by agarose gel electrophoresis to recover a DNA fragment of about 1.8 kb containing the CAG promoter region. The thus recovered respective DNA fragments were ligated using DNA Ligation Kit (manufactured by Takara Shuzo), and *E. coli* DH5α was transformed using the resulting recombinant plasmid DNA to obtain plasmid CAG-pcDNA3.

(2) Construction of hCCR4 Expression Vector

An hCCR4 expression vector was constructed as described below by using the CAG-pcDNA3 obtained in 3(1) of Reference Example 2 and hCCR4 DNA-inserted pcDNA3 (CCR4/pcDNA3). Both of the CAG-pcDNA3 and CCR4/pcDNA3 were allowed to react with HindIII at 37° C. for 1 hour and DNA fragments were recovered by ethanol precipitation. Next, they were allowed to react with BglII (manufactured by Takara Shuzo) at 37° C. for 1 hour and then fractionated by agarose gel electrophoresis to recover a DNA fragment of about 2.0 kb containing the CAG promoter region and a DNA fragment of about 5.5 kb containing the hCCR4 gene region Thereafter, plasmid CAG-CCR4/pcDNA3 was obtained using both of the DNA fragments in the same manner as in 3(1) of Reference Example 2.

(3) Expression of hCCR4 in Animal Cell

The plasmid was introduced into animal cells by electroporation in the same manner as described in 2(2) of Reference Example 2 EL-4 cells (ATCC TIB-39) were suspended in PBS(−) (manufactured by GIBCO-BRL) to give a density of $1\times10^7$ cells/500 μl, 10 μg of the CAG-CCR4/pcDNA3 obtained in 3(2) of Reference Example 2 was added thereto, and the mixture was incubated in ice for 10 minutes and then put into a cuvette for exclusive use (manufactured by Bio-Rad) to carry out gene introduction at 260 V and 500 μFD. After the mixture was further incubated in ice for 10 minutes, the cells were suspended in 200 ml of 10% FCS-RPMI medium and dispensed at 200 μl/well into a 96 well plate for cell culturing. Twenty-four hours after culturing, 100 μl of the culture supernatant was removed from each well, and 10% FCS-RPMI medium containing 1 mg/ml of G418 was dispensed at 100 μl/well to give a final concentration of 0.5 mg/ml. Two weeks thereafter, single clones of between 10 and 100 were selected and cultured again.

(4) Selection of hCCR4-High-Expressing Cell

They were selected by an immunofluorescent method using KM2160 prepared in (5) of Reference Example 1. Into a 96 well U shape plate, $2\times10^5$ cells of each of selected several tens of the gene-introduced clones was dispensed. KM2160 labeled with biotin by a known method (*Enzyme Antibody Method*, published by Gakusai Kikaku) was diluted to 5 μg/ml with a buffer for FACS (1% BSA-PBS, 0.02% EDTA, 0.05% $NaN_3$, pH 7.4), human IgG (manufactured by Welfide) was diluted to 3.75 mg/ml to prevent nonspecific staining, each of the thus diluted antibody solution was dispensed at 200 μl/well, and the mixture was allowed to react in ice for 30 minutes. As a negative control, biotinylated anti-IL-5R antibody (WO 97/10354) was used at the same concentration. After washing twice with 200 μl/well of the buffer, streptoavidin-PE (manufactured by Becton Dickinson Japan) was dispensed at 20 μl/well. Thirty minutes after the reaction in ice in the dark, the cells were washed three times with 200 μl/well and finally suspended to 500 μl, and the fluorescence intensity was measured by a flow cytometer to select one cell line having the highest fluorescence intensity The cell line having the highest fluorescence intensity was used as CCR4/EL-4.

While the invention has been described in detail and with reference to specific embodiments thereof, it will be apparent to one of skill in the art that various changes and modifications can be made therein without departing from the spirit and scope thereof. All references cited herein are incorporated in their entirety.

This application is based on Japanese application No. 2001-265144 filed on Aug. 31, 2001, the entire content of which is incorporated hereinto by reference.

What is claimed is:

1. A human CDR-grafted antibody or antibody fragment thereof which reacts with an extracellular region of human CC chemokine receptor 4 (CCR4) but does not specifically react with a human platelet, wherein said extracellular region is an epitope present in SEQ ID NO: 37, and wherein the human CDR-grafted antibody or antibody fragment thereof comprises an antibody heavy chain (H chain) variable region (V region) comprising SEQ ID NO:4, 9, 10, 11, 38, 39, 40 or 41.

2. The human CDR-grafted antibody or antibody fragment thereof according to claim 1, which further specifically reacts with a cell expressing said extracellular region of human CC chemokine receptor 4 (CCR4).

3. The human CDR-grafted antibody or antibody fragment according to claim 1 or 2, which comprises an antibody heavy chain (H chain) variable region (V region) comprising SEQ ID NO:9 or 10; and an antibody light chain (L chain) V region comprising SEQ ID NO:14.

4. A process for producing a human CDR-grafted antibody or antibody fragment, comprising the steps of:

culturing a transformant which produces the human CDR-grafted antibody or antibody fragment thereof according to claim 3 in a medium to form and accumulate the human CDR-grafted antibody or antibody fragment in the culture; and recovering the antibody or antibody fragment from the culture.

5. The human CDR-grafted antibody or the antibody fragment according to claim 3 and which has a cytotoxic activity against a cell expressing said extracellular region of human CC chemokine receptor 4 (CCR4).

6. A human CDR-grafted antibody or antibody fragment thereof in which the human CDR-grafted antibody or antibody fragment according to claim 3 is chemically conjugated to a radioisotope, protein or agent, or fused to a protein in the form of a fusion antibody.

7. A composition comprising at least one human CDR-grafted antibody or antibody fragment according to claim 3 as an active ingredient, together with a pharmaceutically acceptable carrier.

8. The human CDR-grafted antibody or antibody fragment according to claim 1 or 2, further comprising an antibody light chain (L chain) V region comprising SEQ ID NO:8, 12, 13 or 14.

9. A process for producing a human CDR-grafted antibody or antibody fragment, comprising the steps of:

culturing a transformant which produces the human CDR-grafted antibody or antibody fragment thereof according to claim 8 in a medium to form and accumulate the human CDR-grafted antibody or antibody fragment in the culture; and recovering the antibody or antibody fragment from the culture.

10. The human CDR-grafted antibody or the antibody fragment according to claim 8 and which has a cytotoxic activity against a cell expressing said extracellular region of human CC chemokine receptor 4 (CCR4).

11. A human CDR-grafted antibody or antibody fragment thereof in which the human CDR-grafted antibody or antibody fragment according to claim 8 is chemically conjugated to a radioisotope, protein or agent, or fused to a protein in the form of a fusion antibody.

12. A composition comprising at least one human CDR-grafted antibody or antibody fragment according to claim 8 as an active ingredient, together with a pharmaceutically acceptable carrier.

13. A human CDR-grafted antibody or antibody fragment thereof which reacts with an extracellular region of human CC chemokine receptor 4 (CCR4) but does not specifically react with a human platelet, wherein said extracellular region is an epitope present in SEQ ID NO: 37, and wherein the human CDR-grafted antibody or antibody fragment thereof comprises an antibody light chain (L chain) variable region (V region) comprising SEQ ID NO:8, 12, 13 or 14.

14. The human CDR-grafted antibody or antibody fragment thereof according to claim 13, which further specifically reacts with a cell expressing said extracellular region of human CC chemokine receptor 4 (CCR4).

15. A human CDR-grafted antibody or antibody fragment thereof, which is produced by a transformant KM8759 (FERM BP-8129) or KM8760 (FERM BP-8130).

16. A process for producing a human CDR-grafted antibody or antibody fragment, comprising the steps of:

culturing a transformant which produces the human CDR-grafted antibody or antibody fragment thereof according to any one of claims 1, 13 or 15, or KM8759 (FERM BP-8129) or KM8760 (FERM BP-8130) in a medium to form and accumulate the human CDR-grafted antibody or antibody fragment in the culture; and recovering the antibody or antibody fragment from the culture.

17. A human CDR-grafted antibody or antibody fragment thereof in which the human CDR-grafted antibody or antibody fragment according to any one of claims 1, 13 or 15 is chemically conjugated to a radioisotope, protein or agent, or fused to a protein in the form of a fusion antibody.

18. A composition comprising at least one human CDR-grafted antibody or antibody fragment according to any one of claims 1, 13 or 15 as an active ingredient, together with a pharmaceutically acceptable carrier.

19. The human CDR-grafted antibody or the antibody fragment according to any one of claims 1, 13 or 15 and which has a cytotoxic activity against a cell expressing said extracellular region of human CC chemokine receptor 4 (CCR4).

* * * * *